US012509468B2

(12) United States Patent
Hurley et al.

(10) Patent No.: US 12,509,468 B2
(45) **Date of Patent: *Dec. 30, 2025**

(54) QUINDOLINE COMPOUNDS AND USES THEREOF

(71) Applicant: Arizona Board of Regents on Behalf of the University of Arizona, Tucson, AZ (US)

(72) Inventors: Laurence Hurley, Tucson, AZ (US); Biswanath De, Tucson, AZ (US); Venkateshwar R. Chappeta, Tucson, AZ (US); Tracy A. Brooks, Tucson, AZ (US); Vijay Gokhale, Tucson, AZ (US); Cynthia Miranti, Tucson, AZ (US); Elsa Reyes Reyes, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 1061 days.

This patent is subject to a terminal disclaimer.

(21) Appl. No.: 17/426,932

(22) PCT Filed: Jan. 29, 2020

(86) PCT No.: PCT/US2020/015717

§ 371 (c)(1),
(2) Date: Jul. 29, 2021

(87) PCT Pub. No.: WO2020/160175

PCT Pub. Date: Aug. 6, 2020

(65) Prior Publication Data

US 2022/0098210 A1 Mar. 31, 2022

Related U.S. Application Data

(60) Provisional application No. 62/798,293, filed on Jan. 29, 2019.

(51) Int. Cl.
*C07D 487/14* (2006.01)
*A61K 31/47* (2006.01)
(Continued)

(52) U.S. Cl.
CPC ........ *C07D 487/14* (2013.01); *A61K 31/4709* (2013.01); *A61K 31/4738* (2013.01);
(Continued)

(58) Field of Classification Search
CPC ... C07D 487/14; A61P 35/00; A61K 31/4709; A61K 45/06
See application file for complete search history.

(56) References Cited

U.S. PATENT DOCUMENTS 3,989,816 A 11/1976 Rajadhyaksha
4,444,762 A 4/1984 Rajadhyaksha
(Continued)

FOREIGN PATENT DOCUMENTS

WO WO 2007/062998 6/2007

OTHER PUBLICATIONS

Johnson et al. British Journal of Cancer 2001 84 10 1424 (Year: 2001).*

(Continued)

*Primary Examiner* — Kortney L. Klinkel
*Assistant Examiner* — Sophia Reilly
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having a quindoline (or similar) structure which function as stabilizers of G-quadruplex (G4) formation, and their use as therapeutics for the treatment of cancer (e.g.,
(Continued)

castration-resistant prostate cancer), and other conditions mediated by G4 stabilization.

8 Claims, 3 Drawing Sheets

(51) Int. Cl.

| | |
|---|---|
| ***A61K 31/4709*** | (2006.01) |
| ***A61K 31/4738*** | (2006.01) |
| ***A61K 45/06*** | (2006.01) |
| ***A61P 35/00*** | (2006.01) |

(52) U.S. Cl.

CPC .............. *A61K 45/06* (2013.01); *A61P 35/00* (2018.01); *A61K 31/47* (2013.01)

(56) References Cited

U.S. PATENT DOCUMENTS

| | | | |
|---|---|---|---|
| 5,770,581 A | 6/1998 | Weichselbaum et al. | |
| 8,158,646 B2 | 4/2012 | Ablordeppy | |
| 2007/0249564 A1 | 10/2007 | Erion et al. | |
| 2022/0098210 A1* | 3/2022 | Hurley ................. | C07D 487/14 |

OTHER PUBLICATIONS

J. Figueiredo et al. Life Sciences, 340 (2024) 1222481 (Year: 2024).*
Y. H. Wang et. al. Nucleic Acids Research 2022 50 (Year: 2022).*
Gura et al. Science 278 5430 1997 1041 (Year: 1997).*
Kunnumakkara Experimental Biology and Medicine 2019 244 663 (Year: 2019).*
Cannon et. al. Burgers Medicinal Chemistry and Drug Discovery 5th ed. 1995 (Year: 1995).*
Frasson et. al. "Quindoline-derivatives display potent G-quadruplex-mediated antiviral activity against herpes simplex virus 1" Antiviral Research 2022, 208, 105432, 1-9 DOI: 10.1016/j.antiviral.2022.105432 (Year: 2022).*
Haider et. al. "Intramolecular [4+2] cycloaddition reactions of indolylalkylpyridazines: synthesis of annulated carbazoles" Tetrahedron, 2004, 60, 31, 6495-6507. DOI: 10.1016/j.tet.2004.06.008 (Year: 2004).*
Indumathi et. al. "Novel synthesis of benzo[b]carbazoles" Tetrahedron Letters, 2014, 55, 5361-5364. DOI: 10.1016/j.tetlet.2014.07.070 (Year: 2014).*
Yamamoto, M., Mine, H., Akazawa, K., Maehara, Y., & Sugimachi, K. "Gastrointestinal cancer and herpes zoster in adults." Hepatogastroenterology, 2003, 50, 52, abstract only. PMID: 12845977. Accessed Jan. 23, 2025. (Year: 2003).*
International Search Report and Written Opinion for PCT/US20/15717. Mailed Jun. 11, 2020. 12 pages.
Artusi et al., The Herpes Simplex Virus-1 genome contains multiple clusters of repeated G-quadruplex: Implications for the antiviral activity of a G-quadruplex ligand. Antiviral Res. Jun. 2015;118:123-31.
Bierer et al., Antihyperglycemic activities of cryptolepine analogues: an ethnobotanical lead structure isolated from Cryptolepis sanguinolenta. J Med Chem. Jul. 16, 1998;41(15):2754-64.
Bundgard, Design of Prodrugs. Elsevier, Amsterdam 1985. TOC only. 2 pages.
Burger's Medicinal Chemistry and Drug Discovery, 5th Ed., M. Wolff (ed.), John Wiley & Sons, 1995. pp. 949-982.
Burger's Medicinal Chemistry and Drug Discovery, 5th Ed., M. Wolff (ed.), John Wiley & Sons, 1995. pp. 172-178.
Callegaro et al., A core extended naphtalene diimide G-quadruplex ligand potently inhibits herpes simplex virus 1 replication. Sci Rep. May 24, 2017;7(1):2341. 9 pages.
Che et al., Discovery of Novel Schizocommunin Derivatives as Telomeric G-Quadruplex Ligands That Trigger Telomere Dysfunction and the Deoxyribonucleic Acid (DNA) Damage Response. J Med Chem. Apr. 26, 2018;61(8):3436-3453.
Daelemans et al., A time-of-drug addition approach to target identification of antiviral compounds. Nat Protoc. Jun. 2011;6(6):925-33.
De Armond et al., Evidence for the presence of a guanine quadruplex forming region within a polypurine tract of the hypoxia inducible factor 1alpha promoter. Biochemistry. Dec. 13, 2005;44(49):16341-50.
De Feo et al., Rat carotid arteriotomy: c-myc is involved in negative remodelling and apoptosis. J Cardiovasc Med (Hagerstown). Jan. 2006;7(1):61-7.
Dexheimer et al., Deconvoluting the structural and drug-recognition complexity of the G-quadruplex-forming region upstream of the bcl-2 P1 promoter. J Am Chem Soc. Apr. 26, 2006;128(16):5404-15.
Elion. Acyclovir: discovery, mechanism of action, and selectivity. J Med Virol. 1993;Suppl 1:2-6.
Hahn et al., Modulation of gene expression by high and low density lipoproteins in human vascular smooth muscle cells. Biochem Biophys Res Commun. Aug. 15, 1991;178(3):1465-71.
Hardin et al., Monovalent cation induced structural transitions in telomeric DNAs: G-DNA folding intermediates. Biochemistry. May 7, 1991;30(18):4460-72.
He et al., New quinazoline derivatives for telomeric G-quadruplex DNA: effects of an added phenyl group on quadruplex binding ability. Eur J Med Chem. May 2013;63:1-13.
Higuchi ed et al., Pro-Drugs as Novel Delivery Systems. Am. Chem. Soc., 1975. TOC only. 13 pages.
Hurley et al., Modulating the functional contributions of c-Myc to the human endothelial cell cyclic strain response. J Vasc Res. 2010;47(1):80-90.
Johnston et al., Synthesis of potential anticancer agents. 38. N-Nitrosoureas. 4. Further synthesis and evaluation of haloethyl derivatives. J Med Chem. Jul. 1971;14(17):600-14.
Kipshidze et al., Antisense therapy for restenosis following percutaneous coronary intervention. Expert Opin Biol Ther. Jan. 2005;5(1):79-89.
Komuro et al., Endothelin stimulates c-fos and c-myc expression and proliferation of vascular smooth muscle cells. FEBS Lett. Oct. 10, 1988;238(2):249-52.
Le Sann et al., Synthesis and preliminary evaluation of novel analogues of quindolines as potential stabilisers of telomeric G-quadruplex DNA. Tetrahedron 2007, vol. 63, Iss 52. 12903-12911.
Marin et al., Distribution of c-myc oncoprotein in healthy and atherosclerotic human carotid arteries. J Vasc Surg. Aug. 1993;18(2):170-6.
Meyer et al., Reflecting on 25 years with MYC. Nat Rev Cancer. Dec. 2008;8(12):976-90.
Miyazaki et al., Rational design of 4-amino-5,6-diaryl-furo[2,3-d] pyrimidines as potent glycogen synthase kinase-3 inhibitors. Bioorg Med Chem Lett. Mar. 15, 2008;18(6):1967-71.
Naftilan et al., Angiotensin II induces c-fos expression in smooth muscle via transcriptional control. Hypertension. Jun. 1989;13(6 Pt 2):706-11.
Ou et al., Stabilization of G-quadruplex DNA and down-regulation of oncogene c-myc by quindoline derivatives. J Med Chem. Apr. 5, 2007;50(7):1465-74.
Palumbo et al., Formation of a Unique End-to-End Stacked Pair of G-Quadruplexes in the hTERT Core Promoter with Implications for Inhibition of Telomerase by G-Quadruplex-Interactive Ligands. J. Am. Chem. Soc. 2009, 131, 31, 10878-10891.
Qin et al., Characterization of the G-quadruplexes in the duplex nuclease hypersensitive element of the PDGF-A promoter and modulation of PDGF-A promoter activity by TMPyP4. Nucleic Acids Res. 2007;35(22):7698-713.
Qin et al., Structures, folding patterns, and functions of intramolecular DNA G-quadruplexes found in eukaryotic promoter regions. Biochimie. Aug. 2008;90(8):1149-71.
Ragazzon et al., Competition dialysis: a method for the study of structural selective nucleic acid binding. Methods. Jun. 2007;42(2):173-82.

(56) References Cited

OTHER PUBLICATIONS

Shachaf et al., Genomic and proteomic analysis reveals a threshold level of MYC required for tumor maintenance. Cancer Res. Jul. 1, 2008;68(13):5132-42.
Shi et al., Downregulation of c-myc expression by antisense oligonucleotides inhibits proliferation of human smooth muscle cells. Circulation. Sep. 1993;88(3):1190-5.
Siddiqui-Jain et al., Direct evidence for a G-quadruplex in a promoter region and its targeting with a small molecule to repress c-MYC transcription. Proc Natl Acad Sci U S A. Sep. 3, 2002;99(18):11593-8.
Silverman, The Organic Chemistry of Drug Design and Drug Action, Academic Press, San Diego, CA 1992. pp. 352-401.
Sun et al., Facilitation of a structural transition in the polypurine/polypyrimidine tract within the proximal promoter region of the human VEGF gene by the presence of potassium and G-quadruplex-interactive agents. Nucleic Acids Res. Oct. 20, 2005;33(18):6070-80.
Takeuchi et al., Synthesis and antitumor activity of fused quinoline derivatives. V. Methylindolo[3,2-b] quinolines. Chem Pharm Bull (Tokyo). Dec. 1997;45(12):2096-9.
Van Oeveren et al., Discovery of an androgen receptor modulator pharmacophore based on 2-quinolinones. Bioorg Med Chem Lett. Mar. 15, 2007;17(6):1523-6.
Verma et al., Genome-wide computational and expression analyses reveal G-quadruplex DNA motifs as conserved cis-regulatory elements in human and related species. J Med Chem. Sep. 25, 2008;51(18):5641-9.
Von Rahden et al., c-myc amplification is frequent in esophageal adenocarcinoma and correlated with the upregulation of VEGF-A expression. Neoplasia. Sep. 2006;8(9):702-7.
Weiss et al., Dissociation between activation of growth-related genes and mitogenic responses of neonatal vascular smooth muscle cells. Biochem Biophys Res Commun. Dec. 16, 1991;181(2):617-22.
Xiang et al., Piperazine sulfonamides as potent, selective, and orally available 11beta-hydroxysteroid dehydrogenase type 1 inhibitors with efficacy in the rat cortisone-induced hyperinsulinemia model. J Med Chem. Jul. 24, 2008;51(14):4068-71.
Yuan et al., Mass spectrometry of G-quadruplex DNA: formation, recognition, property, conversion, and conformation. Mass Spectrom Rev. Nov.-Dec. 2011;30(6):1121-42.

* cited by examiner

QUINDOLINE COMPOUNDS AND USES THEREOF

CROSS REFERENCE TO RELATED APPLICATIONS

This application is a U.S. 371 national phase entry of International Patent Application No. PCT/US2020/015717, filed Jan. 29, 2020, which claims priority to and the benefit of U.S. Provisional Application No. 62/798,293, filed Jan. 29, 2019, which are hereby incorporated by reference in their entireties.

STATEMENT REGARDING FEDERALLY SPONSORED RESEARCH OR DEVELOPMENT

This invention was made with government support under Grant No. P50 CA095060 awarded by National Institutes of Health. The government has certain rights in the invention.

FIELD OF THE INVENTION

This invention is in the field of medicinal chemistry. In particular, the invention relates to a new class of small-molecules having a quindoline (or similar) structure which function as stabilizers of G-quadruplex (G4) formation, and their use as therapeutics for the treatment of cancer (e.g., castration-resistant prostate cancer), and other conditions mediated by G4 stabilization.

INTRODUCTION

G-quadruplexes are regarded as attractive molecular targets of anticancer therapy of the future (see, Neidle S. (2011), Therapeutic Applications of Quadruplex Nucleic Acids, Academic Press, 1st edition). Indeed, influencing the stability of DNA G-quadruplexes was identified as one of the regulatory mechanisms for key processes on cellular level.

Original compounds useful in influencing the stability of G-quadruplexes are thus of interest for the industry and many academic laboratories.

The present invention addresses this need.

SUMMARY OF THE INVENTION

G-quadruplexes that form in the regulatory region of genes, including oncogenes, have recently emerged as promising targets for the development of anticancer drugs. It has been reported that the G-rich DNA sequences derived from the polypurine/polypyrimidine regions of the c-Myc, VEGF, HIF-1a, Ret, Bcl-2, c-Kit, hTERT, PDGF-Rβ, KDR, and KRAS promoters form three-tetrad G-quadruplex structures in vitro, while PDGF-A and c-Myb form different types of G-quadruplex structures. These polypurine/polypyrimidine motifs are located in the GC-rich regions of promoters and contain four or more runs of two or more contiguous guanines in the G-rich strand. The GC-rich region in the proximal region of these promoters is usually hypersensitive to nucleases and may form an altered structure with a single-stranded character, which is often a feature of transcriptionally active genes. Compelling data show that intramolecular G-quadruplexes form within the promoter regions of some genes and play a critical role in transcriptional regulation (see, for example, Qin, Y. and Hurley, L. H., (2008) Biochemie, 90, 1149-1171). G-quadruplexes have been found in a wide range of organisms including eukaryotes, bacteria, fungi and viruses.

c-Myc, in particular, is an essential transcription factor that plays an important role in cell proliferation, differentiation, and maintenance of other cell-cycle functions. Under pathologic conditions, the expression level of c-Myc is highly elevated, contributing to the development of malignancy in the many human cancers, including colon, pancreatic, breast, small-cell lung, myeloid leukemia, lymphoma, osteosarcomas, and glioblastomas. Thus, considering its importance as a key oncogenic protein, attempts are currently being made to attenuate its expression as a novel therapy for cancer (see, Shachaf et al. (2008) Cancer Research, 68, 5132-5142; Meyer and Penn (2008) Nature, 8, 976-989).

c-Myc has also been found to have applications in the cardiovascular area (see, Haider et al. (2008) J. Med. Chem., 51, 5641-5649). Specific to the development of obstructive vascular disease, c-Myc is quickly induced in vascular smooth muscle cells after arterial injury (see, De Feo et al. (2006) J. Cardiovasc. Med., 7, 61-67) and activated by proliferative signals, including a number of mediators of vascular endothelial cell biology, such as LDL (see, Hahn et al. (1991) Biochem. Biophys. Res Commun., 178, 1465-1471), thrombin (see, Weiss and Ives (1991) Biochem. Biophys. Res Commun., 181, 617-622), endothelin (see, Komuro et al. (1988) FEBS Lett., 238, 249-252), and angiotensin 11 (see, Naftilan et al. (1989) Hypertension, 13, 706-711). Inhibition of c-Myc has been shown to inhibit smooth muscle cell proliferation in vitro and in several animal models (see, Kipshidze et al. (2005) Expert Opin. Biol. Ther., 5, 79-89). Several studies suggest that c-Myc may be involved in the regulation of angiogenesis (see, von Randen et al. (2006) Neoplasia, 8, 702-707). c-Myc also regulates the downstream genes causing cell migration and adhesion, collagen formation, secretion of extracellular matrix, and cell proliferation (see, Shi et al. (1993) Circulation, 88, 1190-1195). When compared with healthy conditions, there is increased c-Myc expression in atherosclerotic plaques, after carotid injury, and in hypertensive rats (see, Mann et al. (1993) J. Vasc. Surg., 18, 170-176). Most importantly, inhibition of c-Myc by a mechanism involving targeting of the G-quadruplex has been shown to modulate the human endothelial cell cyclic strain response (see, Hurley, N. E. Journal of Vascular Research, 2010, 47(1), 80-90).

Early work with known G-quadruplex-interactive agents (TMPy4, telomestatin, etc.) has helped validate the hypothesis that such an approach is viable in terms of controlling gene expression. However, these first-generation leads lacked the drug-like properties for them to be useful as therapeutic tools for cancer.

Experiments conducted during the course of developing embodiments for the present invention synthesized a new class of small-molecules having a quindoline (or similar) structure which can target DNA secondary structures, such as G-quadruplex structures. Such compounds were shown to be capable of differentially binding to a variety of different G-quadruplex structures. Through stabilization of such G-quadruplexes, the instant compounds can act to attenuate gene expression, and in particular, can be useful in treating or inhibiting diseases and conditions where the overexpression of genes has been implicated, such as, but not limited to, diseases associated with abnormal cell proliferation. Such experiments further demonstrated that such compounds having a quindoline (or similar) structure are effective in treating cancers wherein overexpression of c-Myc has been identified as a significant factor for pathogenesis, either directly or via secondary pathways. The instant compounds were also shown to be useful in applications for other conditions related to cell migration and adhesion, collagen formation, secretion of extracellular matrix and cardiovascular-related conditions, such as arterial injury, angiogenesis, atherosclerotic plaques.

As such, the present invention provides a new class of small-molecules having a quindoline (or similar) structure which function as inhibitors of c-Myc activity and/or expression through stabilization of G-quadruplex structures related to c-Myc activity and/or expression, and their use as therapeutics for the treatment of any type of condition or cancer characterized with c-Myc activity.

Androgen receptor (AR) activity drives the development and progression of prostate cancer (PCa). Men who develop regionally advanced or metastatic prostate cancer often have long-term cancer control when treated with androgen-deprivation therapies (ADT), but their disease inevitably becomes resistant to ADT and progresses to castration-resistant prostate cancer (CRPC). ADT involves the use of potent competitive AR antagonists and androgen synthesis inhibitors. Resistance to these treatments often emerges through maintenance of AR signaling via ligand-independent activation mechanisms. As such, there is a need to identify the molecular mechanisms and drugs that interfere with AR expression to overcome this serious drug resistance to ADT.

Additional experiments identified nucleolin as a repressor of androgen receptor (AR) expression, through its ability to stabilize a G-quadruplex structure (G4) in the AR promoter. Over expression of nucleolin in AR-expressing prostate cancer cell lines suppressed, while loss of nucleolin, increased AR mRNA and protein expression. It was found that nucleolin binds to the G4 region within the AR promoter. A dual reporter assay revealed that the G4 sequence in the AR promoter is required for nucleolin to suppress transcription. Moreover, commercially available compounds that stabilize G4 structures increase NCL association with the G4 in the AR promoter and decrease AR expression. Such compounds were shown to effectively reduce AR expression and induce cell death specifically in cells that express AR. These results indicate that nucleolin functions as a transcriptional repressor of the AR gene, and raises the important possibility that G4-stabilizing drugs can increase nucleolin transcriptional repressor activity to block AR expression. Such small-molecules having a quindoline (or similar) structure were shown to effectively stabilize the G4 structure and thereby inhibit AR activity and expression.

As such, the present invention provides a new class of small-molecules having a quindoline (or similar) structure which function as inhibitors of AR activity and/or expression through stabilization of G-quadruplex structures related to AR activity and/or expression, and their use as therapeutics for the treatment of any type of condition or cancer characterized with AR activity and/or AR expression (e.g., cancer (e.g., CRPC).

Accordingly, the present invention contemplates that exposure of animals (e.g., humans) suffering from any type of condition characterized with activity related to unstable G-quadruplex structures to the compounds having a quindoline (or similar) structure will result in an effective treatment of such conditions outright and/or render such conditions more susceptible to additional therapies (e.g., the cell death-inducing activity of cancer therapeutic drugs or radiation therapies).

For example, in some embodiments, the inhibition of AR activity and/or expression occurs through, for example, stabilization of G-quadruplex structures related to AR activity and/or expression (e.g., within the AR promoter). The present invention contemplates that such AR antagonists satisfy an unmet need for the treatment of multiple cancer types, either when administered as monotherapy to induce cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone. In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The quindoline (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within Formula I are provided:

(Formula I)

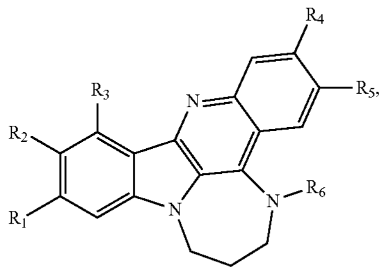

including pharmaceutically acceptable salts, solvates, and/or prodrugs thereof.

Formula I is not limited to a particular chemical moiety for R1, R2, R3, R4, R5 and R6. In some embodiments, the particular chemical moiety for R1, R2, R3, R4, R5 and R6 independently include any chemical moiety that permits the resulting compound to stabilize G-quadruplex structures.

In some embodiments, the particular chemical moiety for R1, R2, R3, R4, R5 and R6 independently include any chemical moiety that permits the resulting compound to inhibit c-Myc activity and/or expression. In some embodiments, the particular chemical moiety for R1, R2, R3, R4, R5 and R6 independently include any chemical moiety that permits the resulting compound to inhibit c-Myc activity and/or expression through stabilization of G-quadruplex structures related to c-Myc activity and/or expression.

In some embodiments, the particular chemical moiety for R1, R2, R3, R4, R5 and R6 independently include any chemical moiety that permits the resulting compound to inhibit AR activity and/or expression. In some embodiments, the particular chemical moiety for R1, R2, R3, R4, R5 and R6 independently include any chemical moiety that permits the resulting compound to inhibit AR activity and/or expression through stabilization of G-quadruplex structures related to AR activity and/or expression. In some embodiments, the particular chemical moiety for R1, R2, R3, R4, R5 and R6 independently include any chemical moiety that permits the resulting compound to inhibit AR activity and/or expression through stabilization of AR promoter related G-quadruplex structures.

In a particular embodiment, compounds encompassed within Formula II are provided:

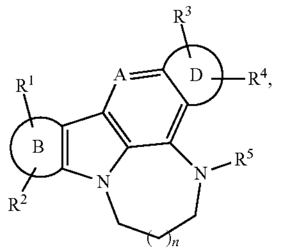

or a pharmaceutically acceptable salt thereof.

Formula II is not limited to a particular chemical structure. In some embodiments, the compound encompassed by Formula II is capable of stabilizing G-quadruplex structures.

In some embodiments, the compound encompassed by Formula II is capable of inhibiting c-Myc activity and/or expression. In some embodiments, the compound encompassed by Formula II is capable of inhibiting c-Myc activity and/or expression through stabilization of G-quadruplex structures related to c-Myc activity and/or expression.

In some embodiments, the compound encompassed by Formula II is capable of inhibiting AR activity and/or expression. In some embodiments, the compound encompassed by Formula II is capable of inhibiting AR activity and/or expression through stabilization of G-quadruplex structures related to AR activity and/or expression. In some embodiments, the compound encompassed by Formula II is capable of inhibiting AR activity and/or expression through stabilization of AR promoter related G-quadruplex structures.

In certain embodiments, the present invention provides compounds shown in Table I.

The invention further provides processes for preparing any of the compounds of the present invention through following at least a portion of the techniques recited in the experimental section.

The compounds of the invention are useful for the treatment, amelioration, or prevention of any type of condition characterized with activity related to unstable G-quadruplex structures disorders (e.g., cancer (e.g., CRPC) (e.g., cancer related to c-Myc activity)).

The compounds of the invention are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In certain embodiments, the cancer is any type of cancer characterized with AR activity and/or AR expression (e.g., cancer (e.g., CRPC)). In certain embodiments, the cancer is any type of cancer characterized with c-Myc activity and/or c-Myc expression.

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents (e.g., anticancer agents or apoptosis-modulating agents, e.g., therapeutic agents useful in treating any type of cancer characterized with AR activity and/or AR expression (e.g., cancer (e.g., CRPC)).

DEFINITIONS

Figure 1:
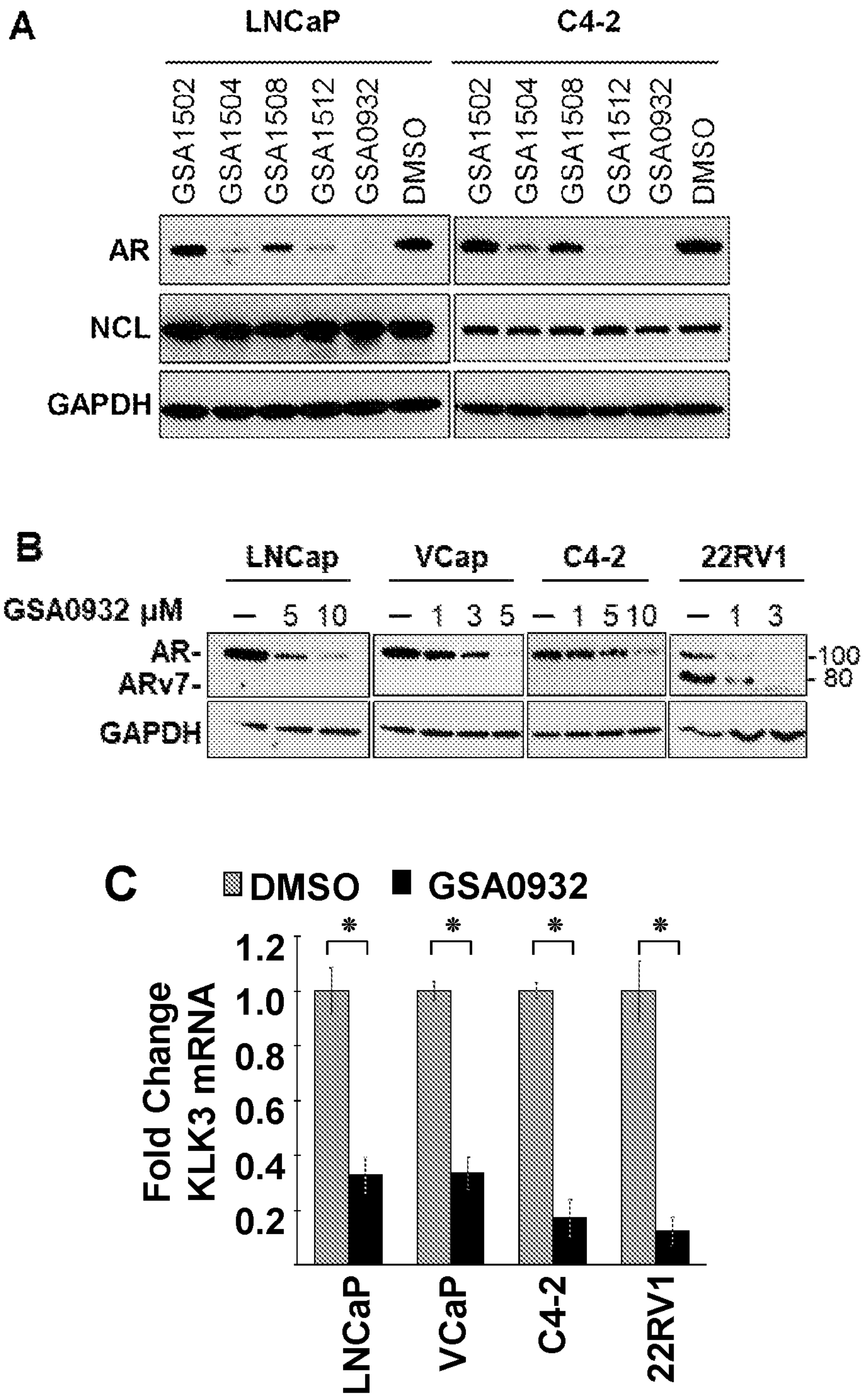
FIG. 1A-H: Specific compounds of the present invention suppress AR protein expression in androgen-dependent (LNCaP) and CRPC tumor cells (C2-4) after a 24 h treatment at 10 μM (A) (Cell lysates from LNCaP and C4-2 cells treated with GSA compounds at a concentration of 10 μM for 24 hours were analyzed for expression of AR, NCL, and GAPDH by immunoblotting). GSA0932 suppress AR expression in 22RV1 and VCaP tumor cells, after 24 h of treatment reaching its maximal inhibitory activity at a concentration of 3 and 5 μM respectively (B) (Cell lysates from indicated prostate cancer cell lines treated with increasing concentrations GSA0932 for 24 hours were analyzed for AR, NCL, and GAPDH by immunoblotting). GSA0932 also inhibits the expression of the clinically relevant ARv7 splice variant in 22RV1 (B) and suppressed mRNA expression of the classical AR target gene, KLK3, also known as PSA (C) (Extracted RNA from indicated prostate cancer cell lines treated for 12 hours with DMSO or GSA0932 (10 μM (LNCaP and C4-2), 5 μM (VCaP), or 3 μM (22RV1) was analyzed for expression of KLK2 (AR target) by RT-qPCR. Values are means±s.e.m; $p<0.05$ (*); n=3). GSA0932 also significantly decreased AR mRNA in LNCaP and C4-2 cells after 12 and 24 hours of treatment at 10 μM (D) (Extracted RNA from LCaP or C4-2 cells treated for 12 or 24 hours with DMSO, 10 μM GSA0932, or 10 μM GSA1502 was analyzed for AR expression by RT-qPCR. Values are means±s.e.m; $p<0.05$ (*); n=3). GSA1502 does not affect AR mRNA and protein expression (A and D), and was used as negative control Quindoline-derived compound. To measure the dependency of GSA0932-mediated AR suppression on the AR G4-element, we generated a stable LNCaP cell lines expressing a dual reporter in which *Gaussia* luciferase is driven by either a wild type or a mutant AR promoter lacking the G4 element, and secreted alkaline phosphatase (SEAP) is driven by a constitutive promoter. GSA0932, but not GSA1502, significantly decreases luciferase activity of a wild type reporter (FIG. 1E) (Relative luciferase in LNCaP cells stably expressing the AR G4 (Wild) or deleted G4 (ΔG4) reporter, treated with DMSO, 10 μM GSA0932, or 10 μM GSA1502 for 12 hours). However, GSA0932 had no effect on the G4-deleted AR reporter (FIG. 1E). GSA0932, but not GSA1502, increases the amount of NCL bound to the G4-element of the AR promoter in both LNCaP and C4-2 cells (FIG. 1F) (ChIP of NCL on AR G4 in the absence or presence of 10 μM GSA0932. Negative (IgG) control. Plotted as fold enrichment relative to IgG). Knocking down NCL expression alleviated the GSA0932 inhibitory activity against AR mRNA expression compared with control cells (FIG. 1G) (LNCaP cells were transfected with scrambled (Scr) or NCL siRNAs and 72 h post-transfection, cells were treated with DMSO, 10 μM GSA0932, or 10 μM GSA1502 for 12 hours. Extracted RNA was analyzed for AR expression by RT-qPCR). GSA0932 has stronger cytotoxic activity against AR-positive tumor cells than non-AR expressing cells (H) (Indicated prostate cancer cell lines, or non-malignant prostate cells (RPWE), treated with different concentrations of GSA0932 for 48 h and cell viability measured by MTT).
Figure 1:
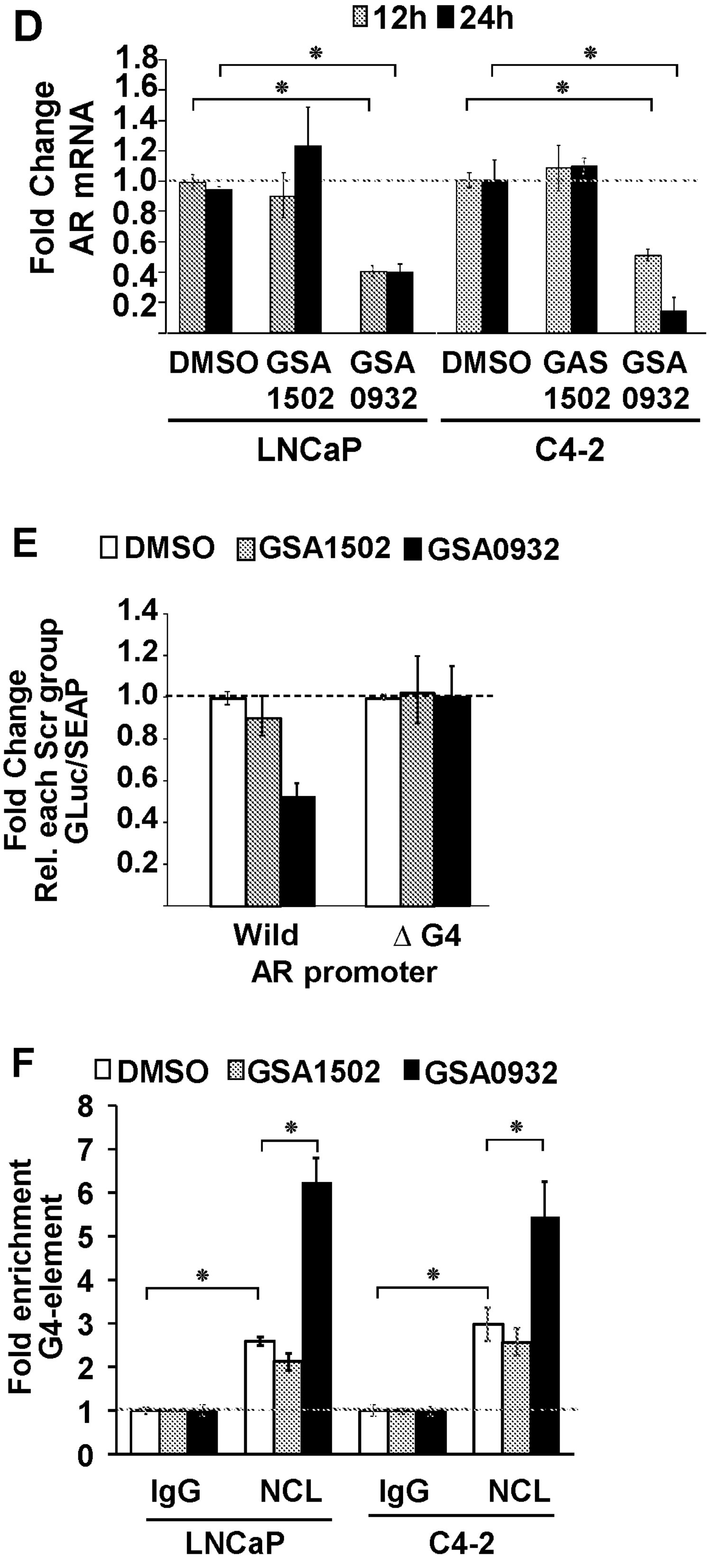
Figure 1:
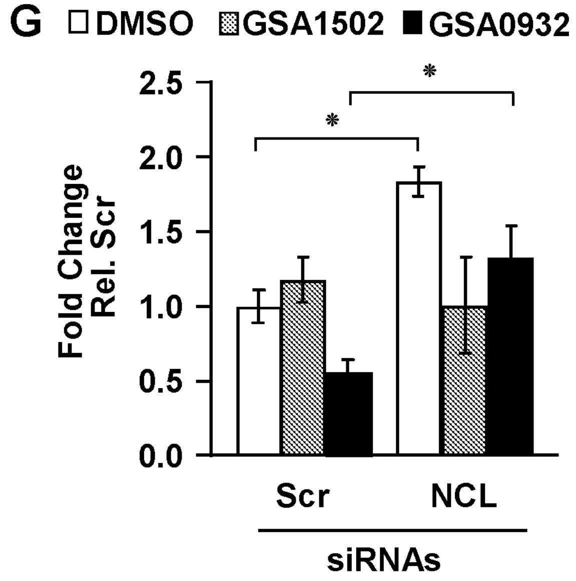
Figure 1:
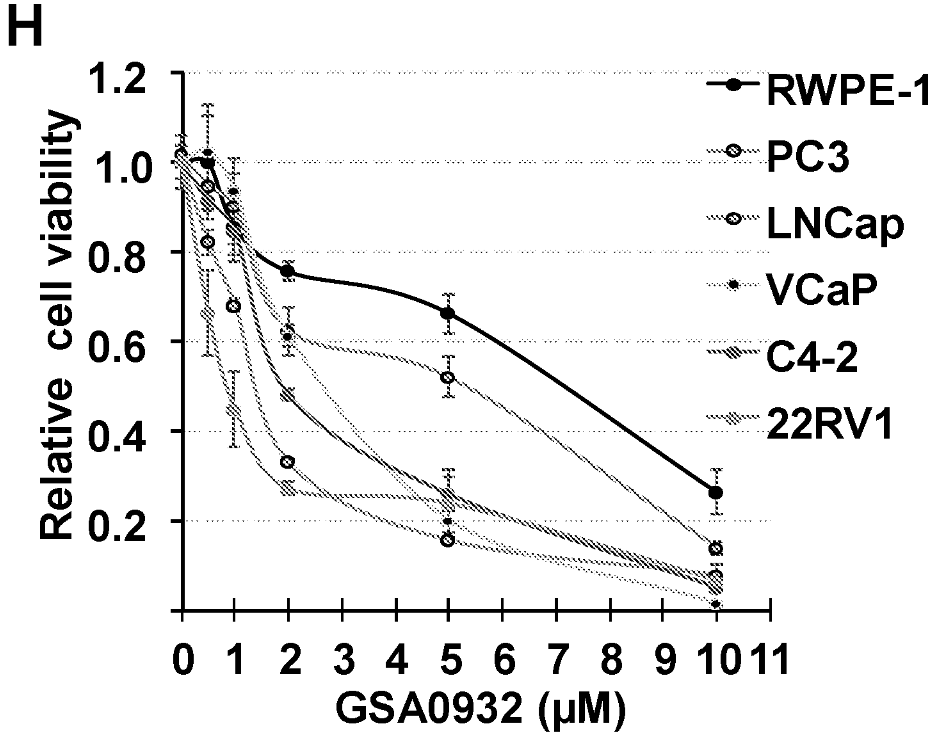

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to $—CH_2—$, $—CH_2CH_2—$, $—CH_2CH_2CHC(CH_3)—$, $—CH_2CH(CH_2CH_3)CH_2—$.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl," as used herein, means a phenyl (i.e., monocyclic aryl), a bicyclic ring system containing at least one phenyl ring or an aromatic bicyclic ring containing only carbon atoms in the aromatic bicyclic ring system or a multicyclic aryl ring system, provided that the bicyclic or multicyclic aryl ring system does not contain a heteroaryl ring when fully aromatic. The bicyclic aryl can be azulenyl, naphthyl, or a phenyl (base ring) fused to a monocyclic cycloalkyl, a monocyclic cycloalkenyl, or a monocyclic heterocyclyl. The bicyclic aryl is attached to the parent molecular moiety through any carbon atom contained within the base ring, or any carbon atom with the napthyl or azulenyl ring. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2,3-dihydrobenzo[b][1,4]dioxan-5-yl, and 2,3-dihydrobenzo[b][1,4]dioxan-6-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl. Multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic cycloalkyl, a monocyclic or bicyclic cycloalkenyl, and a monocyclic or bicyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. The multicyclic aryl is attached to the parent molecular moiety through any carbon atom contained within the base ring. In certain embodiments, multicyclic aryl groups are a phenyl ring (base ring) fused to either (i) one ring system selected from the group consisting of a bicyclic aryl, a bicyclic cycloalkyl, a bicyclic cycloalkenyl, and a bicyclic heterocyclyl; or (ii) two other ring systems independently selected from the group consisting of a phenyl, a monocyclic cycloalkyl, a monocyclic cycloalkenyl, and a monocyclic heterocyclyl, provided that when the base ring is fused to a bicyclic cycloalkyl, bicyclic cycloalkenyl, or bicyclic heterocyclyl, then the base ring is fused to the base ring of the a bicyclic cycloalkyl, bicyclic cycloalkenyl, or bicyclic heterocyclyl. Examples of multicyclic aryl groups include but are not limited to anthracen-9-yl, phenanthren-9-yl, 1,2,3,4,5,6,7,8-octahydroanthracen-9-yl, 1,2,3,4-tetrahydroanthracen-5-yl, and 2,3-dihydronaphtho[2,3-b][1,4]dioxin-7-yl.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryl-aryl," as used herein, means an aryl group, as defined here, appended to the parent molecular moiety through an aryl group, as defined herein. Representative examples of aryl-aryl include, but are not limited to, biphenylyl.

The term "aryl-heteroaryl," as used herein, means an aryl group, as defined here, appended to the parent molecular moiety through a heteroaryl group, as defined herein. Representative examples of aryl-heteroaryl include, but are not limited to, 4-phenyl-pyridin-2-yl and 2-phenyl-imidazol-1-yl.

The term "aryl-heterocyclyl," as used herein, means an aryl group, as defined here, appended to the parent molecular moiety through an heterocyclyl group, as defined herein. Representative examples of aryl-heterocyclyl include, but are not limited to, 4-phenyl-piperazin-1-yl and 2-phenyl-pyrrolidin-1-yl.

The term "azido" as used herein means a $—N_3$ group.

The terms "cyano" and "nitrile" as used herein, mean a —CN group.

The term "cycloalkyl" as used herein, means a monocyclic, bicyclic, or a multicyclic cycloalkyl ring system. Monocyclic ring systems are cyclic hydrocarbon groups containing from 3 to 8 carbon atoms, where such groups can be saturated (i.e., cycloalkanyl) or unsaturated (i.e., cycloalkenyl), but not aromatic. Examples of monocyclic cycloalkyls include cyclopropyl, cyclobutyl, cyclopentyl, cyclopentenyl, cyclohexyl, cyclohexenyl, cycloheptyl, and cyclooctyl. In certain embodiments, monocyclic cycloalkyl groups are fully saturated. Bicyclic cycloalkyl groups are a monocyclic cycloalkyl ring (base ring) fused to one ring selected from the group consisting of a phenyl ring, a monocyclic cycloalkyl, a monocyclic cycloalkenyl, a monocyclic heterocyclyl, and a monocyclic heteroaryl. The bicyclic cycloalkyl is attached to the parent molecular moiety through any carbon atom contained within the base ring. In certain embodiments, bicyclic cycloalkyl groups are a monocyclic cycloalkyl ring (base ring) fused to one ring selected from the group consisting of a phenyl ring, a 5 or 6 membered monocyclic cycloalkyl, a 5 or 6 membered monocyclic cycloalkenyl, a 5 or 6 membered monocyclic heterocyclyl, and a 5 or 6 membered monocyclic heteroaryl. Multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkyl is attached to the parent molecular moiety through any carbon atom contained within the base ring. In certain embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

"Cycloalkenyl" as used herein refers to a monocyclic, bicyclic, or a multicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl groups are a monocyclic cycloalkenyl ring (base ring) fused to one ring selected from the group consisting of a phenyl ring, a monocyclic cycloalkyl, a monocyclic cycloalkenyl, a monocyclic heterocyclyl, and monocyclic heteroaryl. The bicyclic cycloalkenyl is attached to the parent molecular moiety through any carbon atom contained within the base ring. In certain embodiments, bicyclic cycloalkenyl groups are a monocyclic cycloalkenyl ring (base ring) fused to one ring selected from the group consisting of a phenyl ring, a 5 or 6 membered monocyclic cycloalkyl, a 5 or 6 membered monocyclic cycloalkenyl, a 5 or 6 membered monocyclic heterocyclyl, and a 5 or 6 membered monocyclic heteroaryl. Multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic cycloalkenyl is attached to the parent molecular moiety through any carbon atom contained within the base ring. IN certain embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two rings systems independently selected from the group consisting of a phenyl, a monocyclic heteroaryl, a monocyclic cycloalkyl, a monocyclic cycloalkenyl, and a monocyclic heterocyclyl.

The term "halo" or "halogen" as used herein, means —Cl, —Br, —I or —F.

The term "heteroaryl," as used herein, means a monocyclic, bicyclic, or a multicyclic heteroaryl ring system. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl ring (base ring) fused to a phenyl, a monocyclic cycloalkyl, a monocyclic cycloalkenyl, a monocyclic heterocyclyl, or a monocyclic heteroaryl. When the bicyclic heteroaryl contains a fused cycloalkyl, cycloalkenyl, or heterocyclyl ring, then the bicyclic heteroaryl group is connected to the parent molecular moiety through any carbon atom or nitrogen atom contained within the base ring. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl, naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, and thienopyridinyl. In certain embodiments, the bicyclic heteroaryl is a 5 or 6 membered monocyclic heteroaryl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl. The multicyclic heteroaryl group is a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a bicyclic aryl, a monocyclic or bicyclic heteroaryl, a monocyclic or bicyclic heterocyclyl, a monocyclic or bicyclic cycloalkenyl, and a monocyclic or bicyclic cycloalkyl. The multicyclic heteroaryl group is connected to the parent molecular moiety through any carbon atom or nitrogen atom contained within the base ring. In certain embodiments, multicyclic heteroaryl groups are a monocyclic heteroaryl ring (base ring) fused to either (i) one ring system selected from the group consisting of a bicyclic aryl, a bicyclic heteroaryl, a bicyclic heterocyclyl, a bicyclic cycloalkenyl, and a bicyclic cycloalkyl; or (ii) two ring systems selected from the group consisting of a phenyl, a monocyclic heteroaryl, a monocyclic heterocyclyl, a monocyclic cycloalkenyl, and a monocyclic cycloalkyl. Examples of multicyclic heteroaryls include, but are not limited to 5H-[1,2,4]triazino[5,6-b]indol-5-yl, 2,3,4,9-tetrahydro-1H-carbazol-9-yl, 9H-pyrido[3,4-b]indol-9-yl, 9H-carbazol-9-yl, acridin-9-yl, The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heteroaryl-aryl," as used herein, means a heteroaryl group, as defined here, appended to the parent molecular moiety through an aryl group, as defined herein. Representative examples of heteroaryl-aryl include, but are not limited to, 4-pyridin-2-ylphenyl and 2-(imidazol-1-yl)phenyl.

The term "aryl-heterocyclyl," as used herein, means an aryl group, as defined here, appended to the parent molecular moiety through an heterocyclyl group, as defined herein. Representative examples of aryl-heterocyclyl include, but are not limited to, 4-phenyl-piperazin-1-yl and 2-phenyl-pyrrolidin-1-yl.

The term "heterocyclyl" as used herein, means a monocyclic, bicyclic, or multicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is a monocyclic heterocycle ring (base ring) fused to a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the base ring. In certain embodiments, bicyclic heterocycles are a monocyclic heterocycle ring (base ring) fused to a phenyl, a 5 or 6 membered monocyclic cycloalkyl, a 5 or 6 membered monocyclic cycloalkenyl, a 5 or 6 membered monocyclic heterocycle, or a 5 or 6 membered monocyclic heteroaryl. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In certain embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other rings systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The term "heterocyclyl-aryl," as used herein, means a heterocyclyl group, as defined here, appended to the parent molecular moiety through an aryl group, as defined herein. Representative examples of heterocyclyl-aryl include, but are not limited to, 4-(piperazin-1-yl)phenyl and 3-(pyrrolidin-1-yl)phenyl.

The term "nitro" as used herein, means a $—NO_2$ group.

The term "nitroso" as used herein, means a —NO group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, an unsaturated cycloalkyl group as defined herein includes cyclohexenyl, cyclopentenyl, cyclohexadienyl, and the like.

As used herein, the term "cell" is meant to refer to a cell that is in vitro, ex vivo, or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" a cell with a compound includes the administration of a compound described herein to an individual or patient, such as a human, as well as, introducing a compound into a sample containing a cellular or purified preparation.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used here, a subject "in need thereof" refers to a subject that has the disorder or disease to be treated or is predisposed to developing the disease or disorder.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) limiting development of the disease; for example, slowing or halting development of a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, fumaric, toluenesulfonic, methanesulfonic, nitric, benzoic, citric, tartaric, maleic, hydroiodic, alkanoic such as acetic, $HOOC—(CH_2)_n—COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

As used herein, the phrase "pharmaceutically acceptable anion" refers to anionic groups which are tolerated in vivo, such as, but not limited to, halides (fluoride, chloride, bromide, iodide), phosphate, sulfate, sulfinate, formate, fumarate, toluenesulfonate, methanesulfonate, nitrate, benzoate, citrate, tartarate, maleate, alkanoates such as acetate.

"Cell proliferative disorders" as used herein, means a condition in which a cell in a subject's body undergoes abnormal, uncontrolled proliferation. Such conditions include, but are not limited to, polycystic kidney disease, rheumatoid arthritis, osteoarthritis, psoriasis, inflammatory bowel disease; cancers including but not limited to cancers of the colorectum, breast, lung (e.g., small cell lung), liver, pancreas, lymph node, colon, prostate, brain (glioblastomas), head and neck, skin, liver, kidney, heart, bone (osteosarcomas), smooth muscle (e.g., leiomyosarcomas), and hematopoietic system (i.e., cancers involving hyperplastic/neoplastic cells of hematopoietic origin such as those arising from myeloid, lymphoid or erythroid lineages, or precursor cells thereof); and pre-transformation proliferative disorders involving abnormal c-Myc expression, such as myelodisplastic syndrome (MDS).

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, CA (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

DETAILED DESCRIPTION OF THE INVENTION

Experiments conducted during the course of developing embodiments for the present invention synthesized a new class of small-molecules having a quindoline (or similar) structure which can target DNA secondary structures, such as G-quadruplex structures. Such compounds were shown to be capable of differentially binding to a variety of different G-quadruplex structures. Through stabilization of such G-quadruplexes, the instant compounds can act to attenuate gene expression, and in particular, can be useful in treating or inhibiting diseases and conditions where the overexpression of genes has been implicated, such as, but not limited to, diseases associated with abnormal cell proliferation.

Such experiments further demonstrated that such compounds having a quindoline (or similar) structure are effective in treating cancers wherein overexpression of c-Myc has been identified as a significant factor for pathogenesis, either directly or via secondary pathways. The instant compounds were also shown to be useful in applications for other conditions related to cell migration and adhesion, collagen formation, secretion of extracellular matrix and cardiovascular-related conditions, such as arterial injury, angiogenesis, atherosclerotic plaques.

Additional experiments identified nucleolin as a repressor of androgen receptor (AR) expression, through its ability to stabilize a G-quadruplex structure (G4) in the AR promoter. Over expression of nucleolin in AR-expressing prostate cancer cell lines suppressed, while loss of nucleolin, increased AR mRNA and protein expression. It was found that nucleolin binds to the G4 region within the AR promoter. A dual reporter assay revealed that the G4 sequence in the AR promoter is required for nucleolin to suppress transcription. Moreover, commercially available compounds that stabilize G4 structures increase NCL association with the G4 in the AR promoter and decrease AR expression. Such compounds were shown to effectively reduce AR expression and induce cell death specifically in cells that express AR. These results indicate that nucleolin functions as a transcriptional repressor of the AR gene, and raises the important possibility that G4-stabilizing drugs can increase nucleolin transcriptional repressor activity to block AR expression. Such small-molecules having a quindoline (or similar) structure were shown to effectively stabilize the G4 structure and thereby inhibit AR activity and expression.

As such, the present invention provides a new class of small-molecules having a quindoline (or similar) structure which function as inhibitors of c-Myc activity and/or expression through stabilization of G-quadruplex structures related to c-Myc activity and/or expression, and their use as therapeutics for the treatment of any type of condition or cancer characterized with c-Myc activity.

As such, the present invention provides a new class of small-molecules having a quindoline (or similar) structure which function as inhibitors of AR activity and/or expression through stabilization of G-quadruplex structures related to AR activity and/or expression, and their use as therapeutics for the treatment of any type of condition or cancer characterized with AR activity and/or AR expression (e.g., cancer (e.g., CRPC).

In a particular embodiment, compounds encompassed within Formula I are provided:

(Formula I)

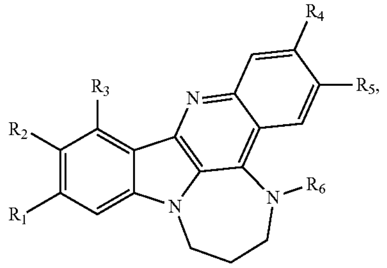

including pharmaceutically acceptable salts, solvates, and/or prodrugs thereof.

Formula I is not limited to a particular chemical moiety for R1, R2, R3, R4, R5 and R6. In some embodiments, the particular chemical moiety for R1, R2, R3, R4, R5 and R6 independently include any chemical moiety that permits the resulting compound to stabilize G-quadruplex structures.

In some embodiments, the particular chemical moiety for R1, R2, R3, R4, R5 and R6 independently include any chemical moiety that permits the resulting compound to inhibit c-Myc activity and/or expression. In some embodiments, the particular chemical moiety for R1, R2, R3, R4, R5 and R6 independently include any chemical moiety that permits the resulting compound to inhibit c-Myc activity and/or expression through stabilization of G-quadruplex structures related to c-Myc activity and/or expression.

In some embodiments, the particular chemical moiety for R1, R2, R3, R4, R5 and R6 independently include any chemical moiety that permits the resulting compound to inhibit AR activity and/or expression. In some embodiments, the particular chemical moiety for R1, R2, R3, R4, R5 and R6 independently include any chemical moiety that permits the resulting compound to inhibit AR activity and/or expression through stabilization of G-quadruplex structures related to AR activity and/or expression. In some embodiments, the particular chemical moiety for R1, R2, R3, R4, R5 and R6 independently include any chemical moiety that permits the resulting compound to inhibit AR activity and/or expression through stabilization of AR promoter related G-quadruplex structures.

In some embodiments, R1 is hydrogen or methyl.

In some embodiments, R2 is hydrogen,

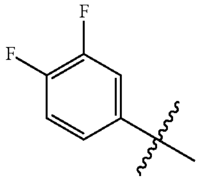
,
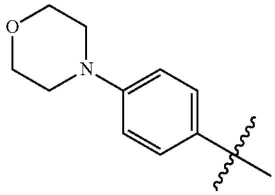
,
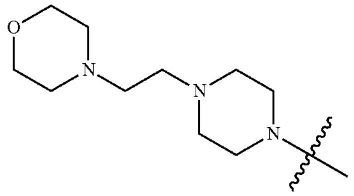
,
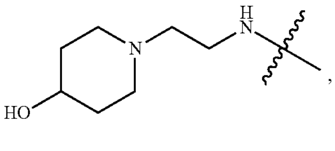
, and

-continued
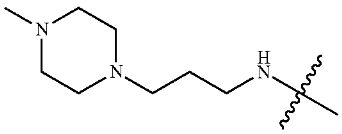
.
In some embodiments, R3 is hydrogen or methyl.
In some embodiments, R4 is selected from hydrogen,
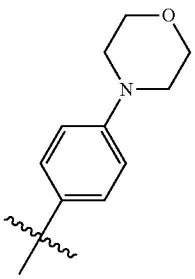
,
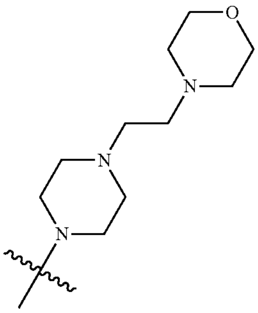
,
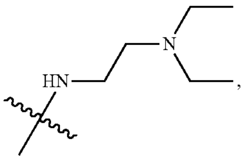
,
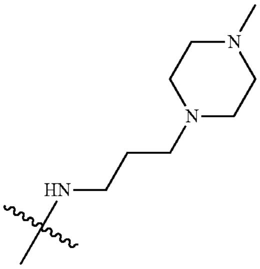
,
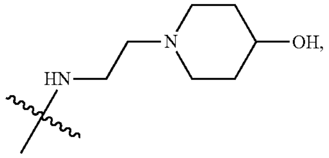
,
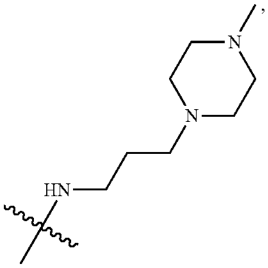
,
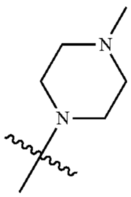
,
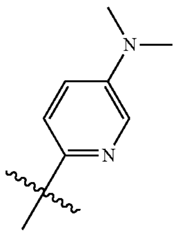
,
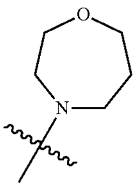
,
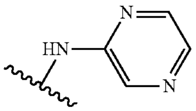
,
-continued
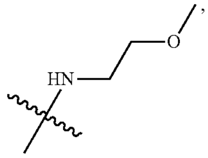
,
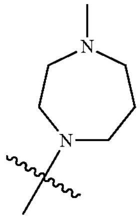
,
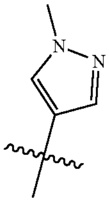
,
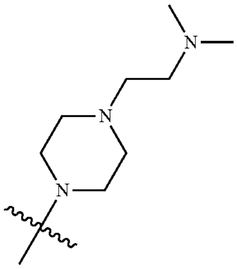
,
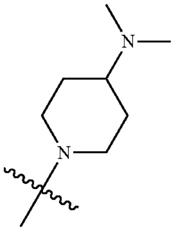
,
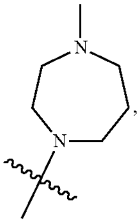
,
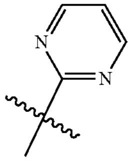
,
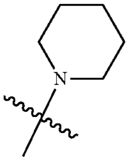
, and
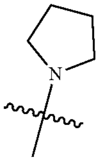
.
In some embodiments, R5 is selected from Hydrogen, halogen (e.g., Chlorine, Bromine),
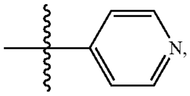
,
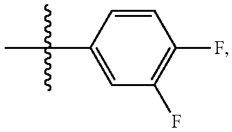
,
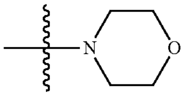
and
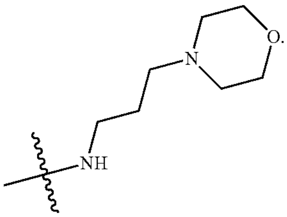
.
In some embodiments, R6 is selected from
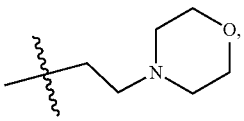
,
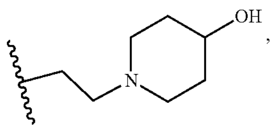
, -continued
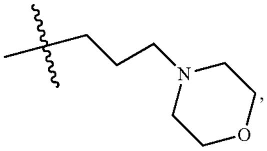
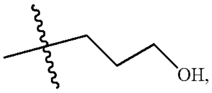
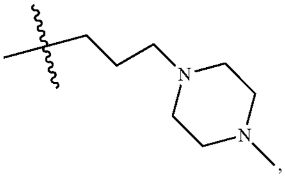
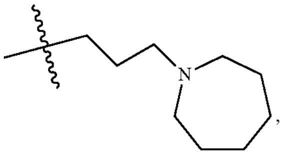
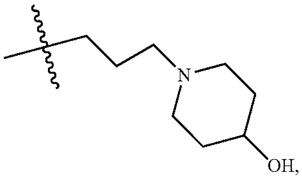
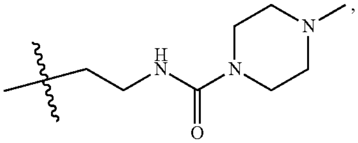
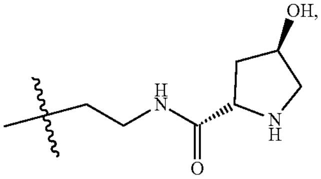
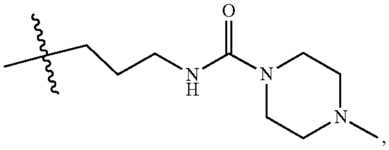
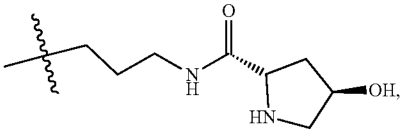
-continued
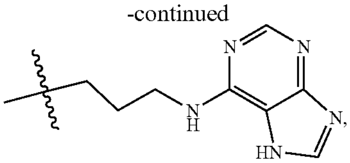
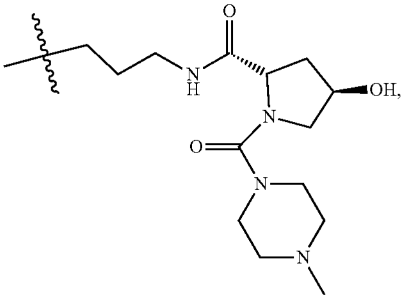
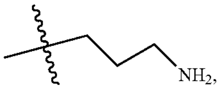
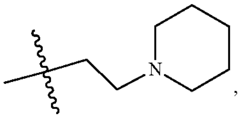
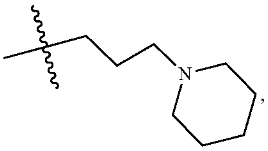
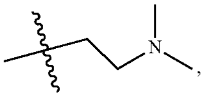
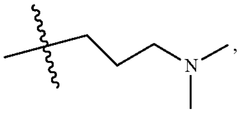
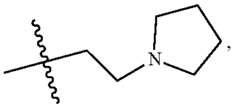
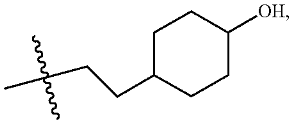
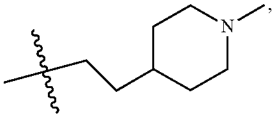
and
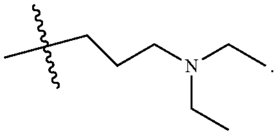
In some embodiments, compounds shown in Table I are contemplated for Formula I.
TABLE I
| Structures of Quindoline compounds | | |
| --- | --- | --- |
| Compound Number | | Structure |
| 1 | GSA0817 | 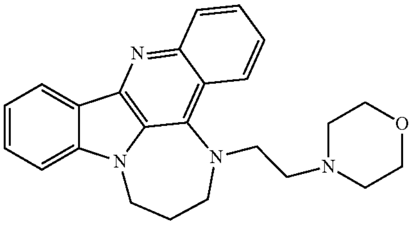 [SMILES: c1ccc2c3c4c(nc2c1)c1ccccc1n4CCCN3CCN1CCOCC1] |

TABLE I-continued
| Structures of Quindoline compounds | | |
|---|---|---|
| Compound Number | | Structure |
| 2 | GSA0829 | 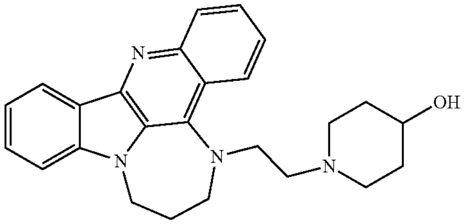 [SMILES: OC1CCN(CCN2CCCn3c4ccccc4c4nc5ccccc5c2c43)CC1] |
| 3 | GSA0825 | 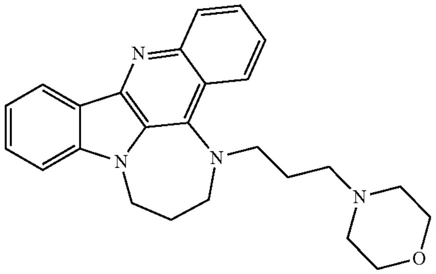 [SMILES: c1ccc2c3c4c(nc2c1)c1ccccc1n4CCCN3CCCN1CCOCC1] |
| 4 | GSA0826 | 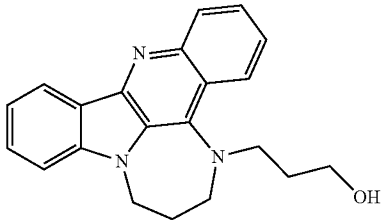 [SMILES: OCCCN1CCCn2c3ccccc3c3nc4ccccc4c1c32] |
| 5 | GSA0903 | 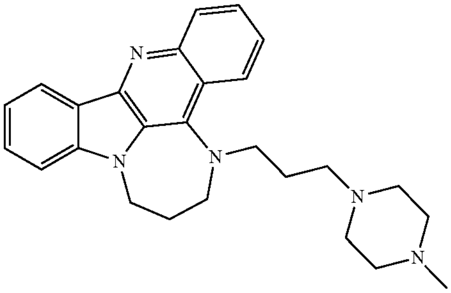 [SMILES: CN1CCN(CCCN2CCCn3c4ccccc4c4nc5ccccc5c2c43)CC1] |
| 6 | GSA0920 | 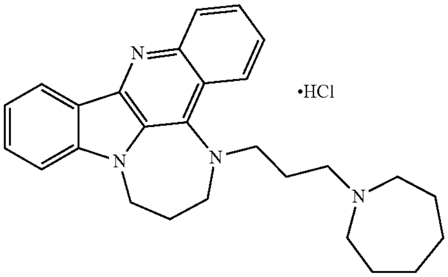 [SMILES: c1ccc2c3c4c(nc2c1)c1ccccc1n4CCCN3CCCN1CCCCCC1 ; Cl] |

TABLE I-continued
Structures of Quindoline compounds
| Compound Number | | Structure |
|---|---|---|
| 7 | GSA0216 | 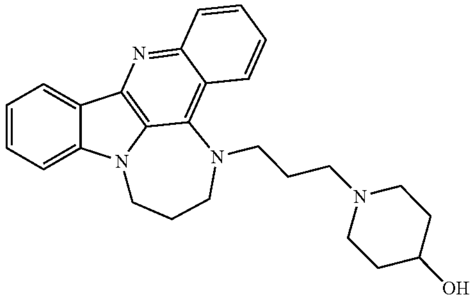 [SMILES: OC1CCN(CCCN2CCCn3c4ccccc4c4nc5ccccc5c2c43)CC1] |
| 8 | GSA0833 | 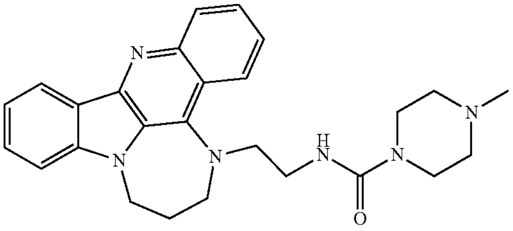 [SMILES: CN1CCN(C(=O)NCCN2CCCn3c4ccccc4c4nc5ccccc5c2c43)CC1] |
| 9 | GSA0843 | 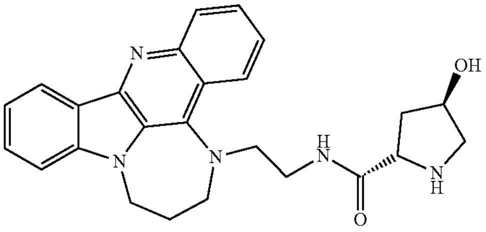 |
| 10 | GSA0848 | 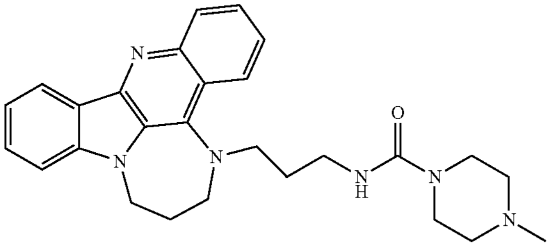 [SMILES: CN1CCN(C(=O)NCCCN2CCCn3c4ccccc4c4nc5ccccc5c2c43)CC1] |
| 11 | GSA0901 | 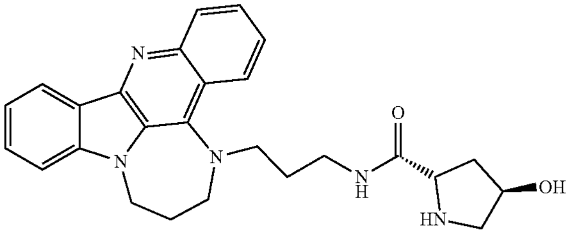 |
| 12 | GSA0926 | 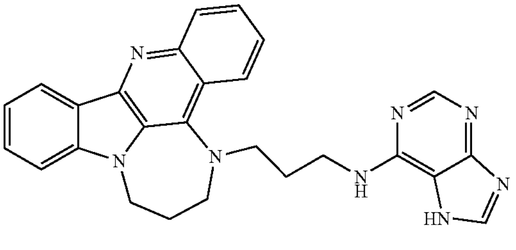 [SMILES: c1ccc2c3c4c(nc2c1)c1ccccc1n4CCCN3CCCNc1ncnc2nc[nH]c12] |

TABLE I-continued
| Structures of Quindoline compounds | | |
|---|---|---|
| Compound Number | | Structure |
| 13 | GSA0921 | 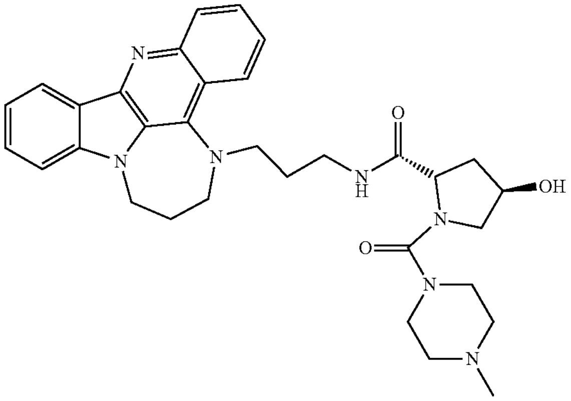 |
| 14 | GSA1141 | 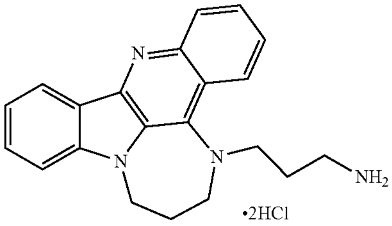 [SMILES: NCCCN1CCCn2c3ccccc3c3nc4ccccc4c1c32] |
| 15 | GSA1202 | 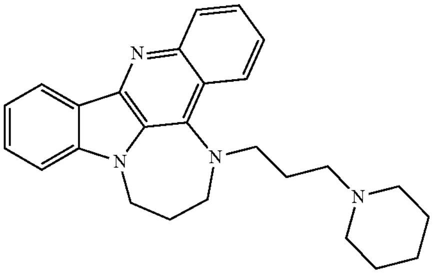 |
| 16 | GSA1204 | 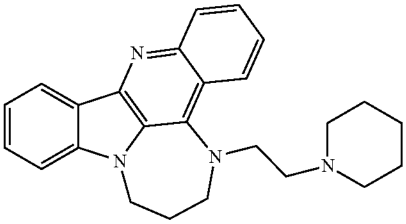 [SMILES: c1ccc2c3c4c(nc2c1)c1ccccc1n4CCCN3CCN1CCCCC1] |
| 17 | GSA0830 | 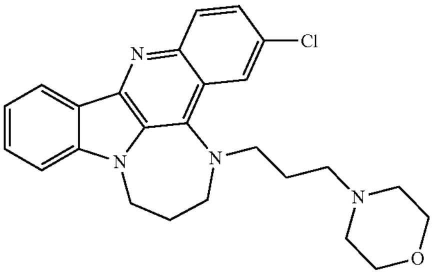 [SMILES: Clc1ccc2nc3c4ccccc4n4c3c(c2c1)N(CCCN1CCOCC1)CCC4] |

TABLE I-continued
| Structures of Quindoline compounds | | |
|---|---|---|
| Compound Number | | Structure |
| 18 | GSA0844 | 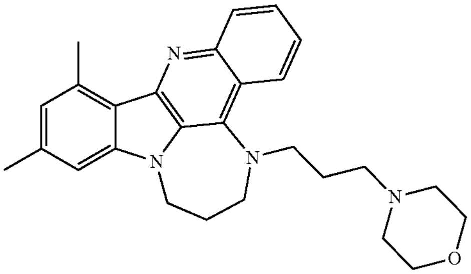 [SMILES: Cc1cc(C)c2c3nc4ccccc4c4c3n(c2c1)CCCN4CCCN1CCOCC1] |
| 19 | GSA0907 | 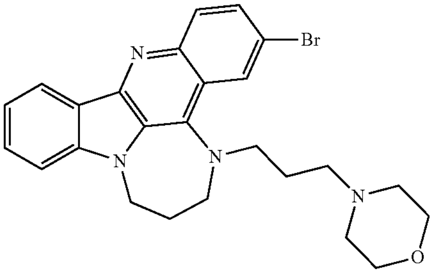 |
| 20 | GSA1502 | 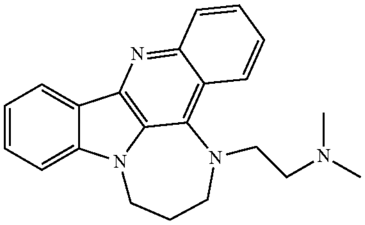 [SMILES: CN(C)CCN1CCCn2c3ccccc3c3nc4ccccc4c1c32] |
| 21 | GSA1504 | 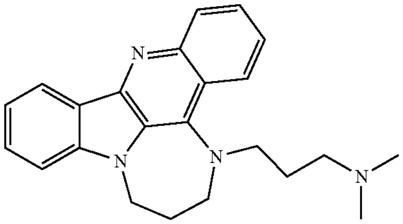 [SMILES: CN(C)CCCN1CCCn2c3ccccc3c3nc4ccccc4c1c32] |
| 22 | GSA1510 | 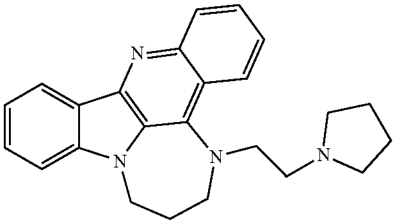 [SMILES: c1ccc2c3c4c(nc2c1)c1ccccc1n4CCCN3CCN1CCCC1] |
| 23 | GSA1512 | 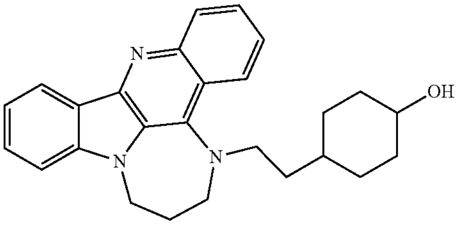 [SMILES: OC1CCC(CCN2CCCn3c4ccccc4c4nc5ccccc5c2c43)CC1] |

TABLE I-continued
| Structures of Quindoline compounds | | |
|---|---|---|
| Compound Number | | Structure |
| 24 | GSA1508 | 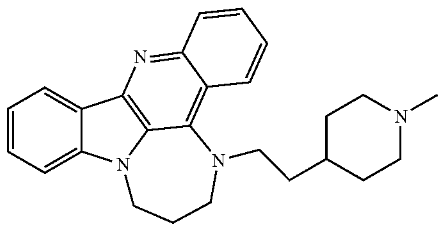 [SMILES: CN1CCC(CCN2CCCn3c4ccccc4c4nc5ccccc5c2c43)CC1] |
| 25 | GSA0114 | 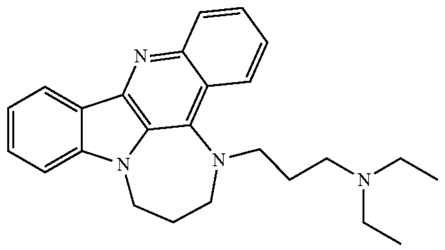 [SMILES: CCN(CC)CCCN1CCCn2c3ccccc3c3nc4ccccc4c1c32] |
| 26 | GSA0932 | 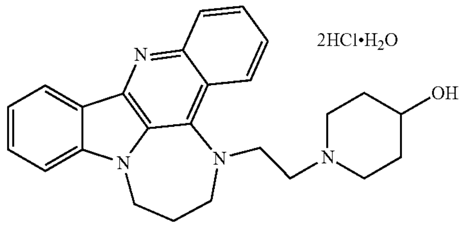 |
| 27 | GSA0905 | 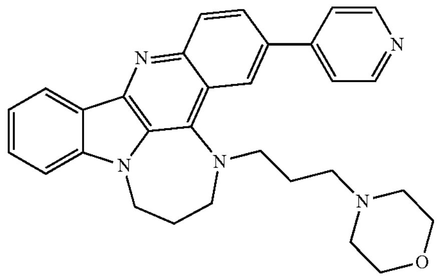 [SMILES: c1ccc2c(c1)c1nc3ccc(-c4ccncc4)cc3c3c1n2CCCN3CCCN1CCOCC1] |
| 28 | GSA0908 | 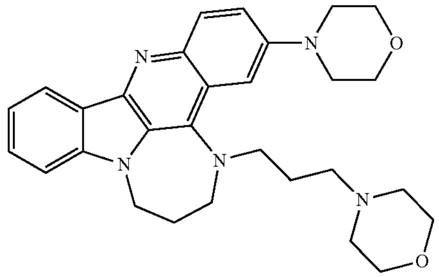 [SMILES: c1ccc2c(c1)c1nc3ccc(N4CCOCC4)cc3c3c1n2CCCN3CCCN1CCOCC1] |

TABLE I-continued
| Structures of Quindoline compounds | | |
|---|---|---|
| Compound Number | | Structure |
| 29 | GSA1010 | 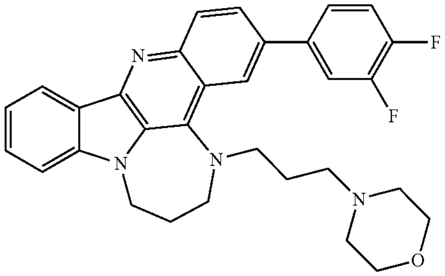 [SMILES: Fc1ccc(-c2ccc3nc4c5ccccc5n5c4c(c3c2)N(CCCN2CCOCC2)CCC5)cc1F] |
| 30 | GSA0257 | 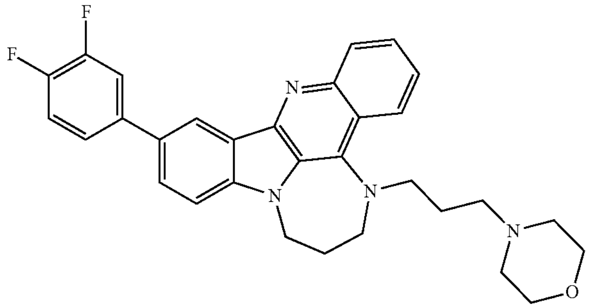 [SMILES: Fc1ccc(-c2ccc3c(c2)c2nc4ccccc4c4c2n3CCCN4CCCN2CCOCC2)cc1F] |
| 31 | GSA1011 | 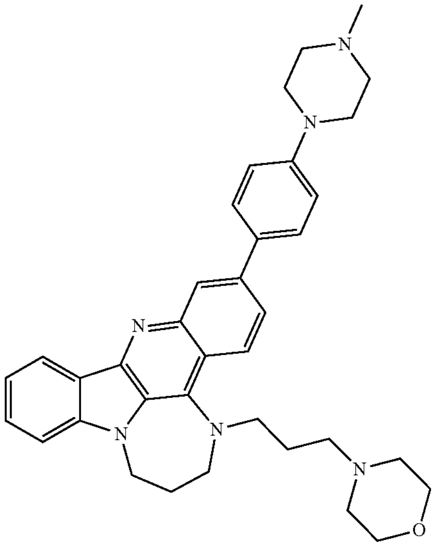 [SMILES: CN1CCN(c2ccc(-c3ccc4c5c6c(nc4c3)c3ccccc3n6CCCN5CCCN3CCOCC3)cc2)CC1] |
| 32 | GSA1014 | 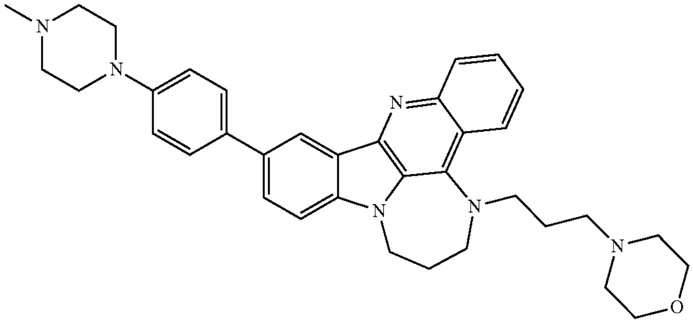 [SMILES: CN1CCN(c2ccc(-c3ccc4c(c3)c3nc5ccccc5c5c3n4CCCN5CCCN3CCOCC3)cc2)CC1] |

TABLE I-continued
| Structures of Quindoline compounds | | |
|---|---|---|
| Compound Number | | Structure |
| 33 | GSA0923 | 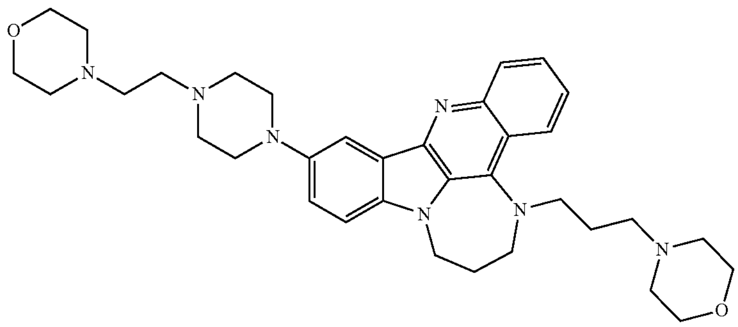 [SMILES: c1ccc2c3c4c(nc2c1)c1cc(N2CCN(CCN5CCOCC5)CC2)ccc1n4CCCN3CCCN1CCOCC1] |
| 34 | GSA1108 | 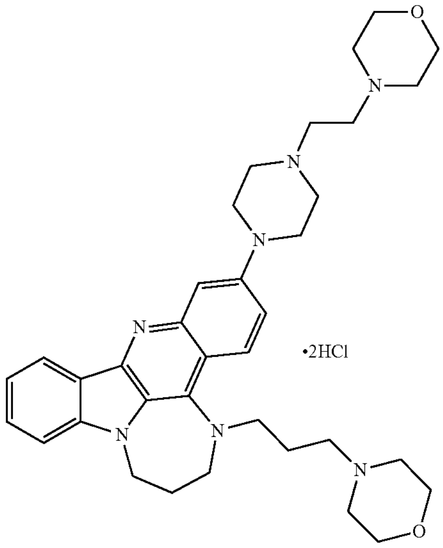 [SMILES: c1ccc2c(c1)c1nc3cc(N4CCN(CCN5CCOCC5)CC4)ccc3c3c1n2CCCN3CCCN1CCOCC1] |
| 35 | GSA0911 | 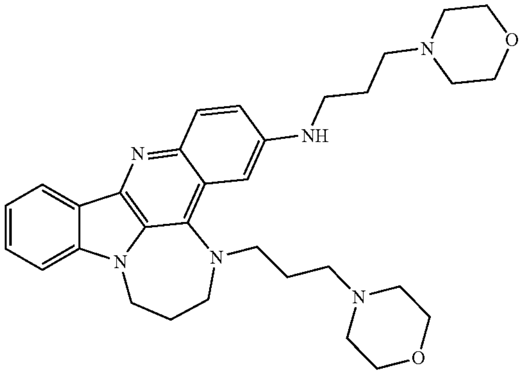 [SMILES: c1ccc2c(c1)c1nc3ccc(NCCCN4CCOCC4)cc3c3c1n2CCCN3CCCN1CCOCC1] |

TABLE I-continued
| Structures of Quindoline compounds | | |
|---|---|---|
| Compound Number | | Structure |
| 36 | GSA1107 | 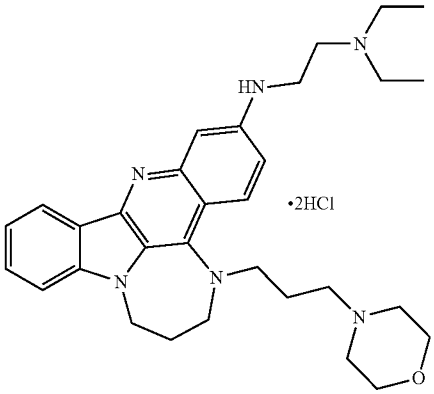 [SMILES: CCN(CC)CCNc1ccc2c3c4c(nc2c1)c1ccccc1n4CCCN3CCCN1CCOCC1] •2HCl |
| 37 | GSA1016 | 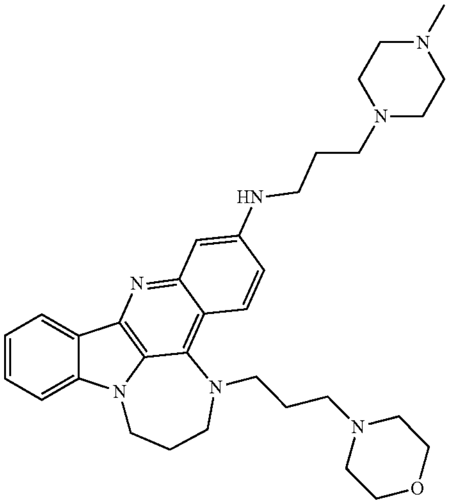 [SMILES: CN1CCN(CCCNc2ccc3c4c5c(nc3c2)c2ccccc2n5CCCN4CCCN2CCOCC2)CC1] |
| 38 | GSA0261 | 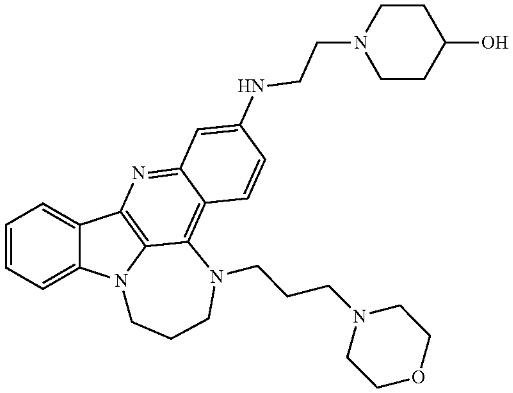 [SMILES: OC1CCN(CCNc2ccc3c4c5c(nc3c2)c2ccccc2n5CCCN4CCCN2CCOCC2)CC1] |

TABLE I-continued
| Structures of Quindoline compounds | | |
|---|---|---|
| Compound Number | | Structure |
| 39 | GSA1021 | 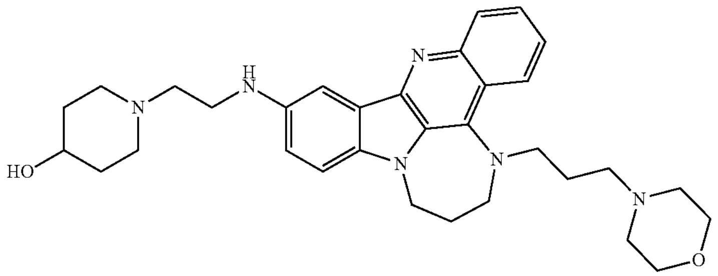 [SMILES: OC1CCN(CCNc2ccc3c(c2)c2nc4ccccc4c4c2n3CCCN4CCCN2CCOCC2)CC1] |
| 40 | GSA1104 | 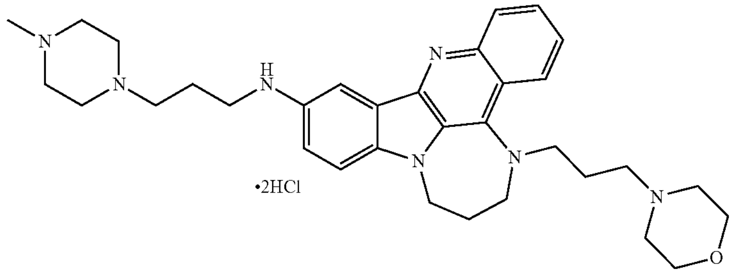 [SMILES: CN1CCN(CCCNc2ccc3c(c2)c2nc4ccccc4c4c2n3CCCN4CCCN2CCOCC2)CC1] |
| 41 | GSA1019 | 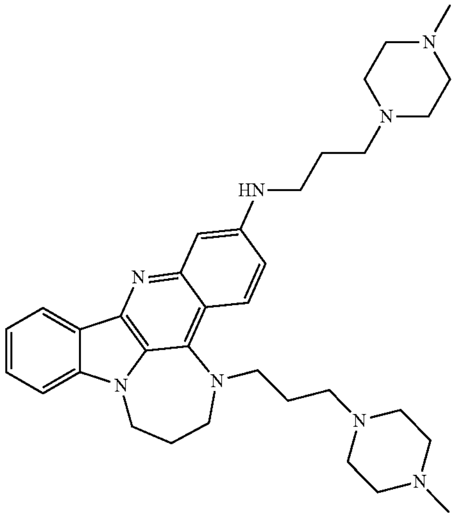 [SMILES: CN1CCN(CCCNc2ccc3c4c5c(nc3c2)c2ccccc2n5CCCN4CCCN2CCN(C)CC2)CC1] |
| 42 | GSA1018 | 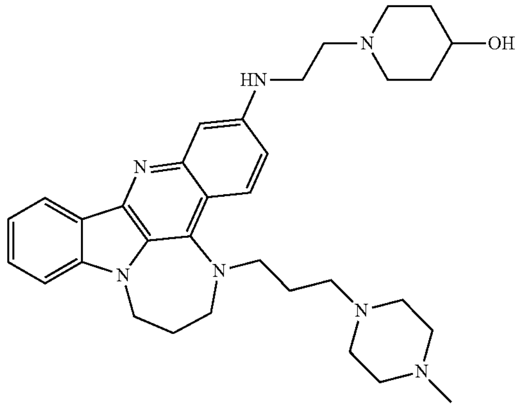 [SMILES: CN1CCN(CCCN2CCCn3c4ccccc4c4nc5cc(NCCN6CCC(O)CC6)ccc5c2c43)CC1] |

TABLE I-continued
| Structures of Quindoline compounds | | |
|---|---|---|
| Compound Number | | Structure |
| 43 | GSA1109 | 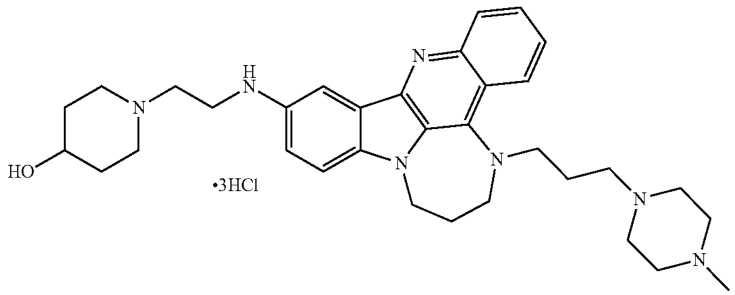 [SMILES: CN1CCN(CCCN2CCCn3c4ccc(NCCN5CCC(O)CC5)cc4c4nc5ccccc5c2c43)CC1] |
| 44 | GSA1110 | 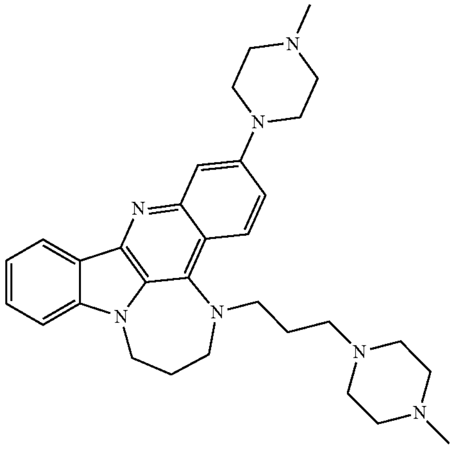 [SMILES: CN1CCN(CCCN2CCCn3c4ccccc4c4nc5cc(N6CCN(C)CC6)ccc5c2c43)CC1] |
| 45 | GSA1111 | 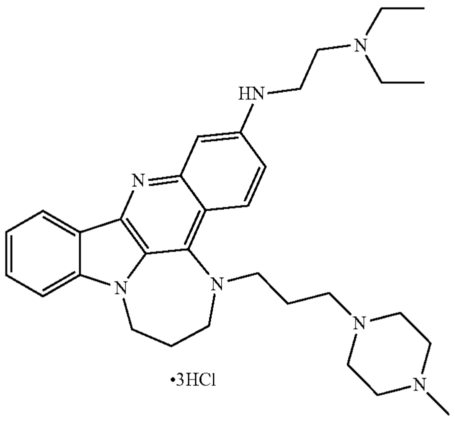 [SMILES: CCN(CC)CCNc1ccc2c3c4c(nc2c1)c1ccccc1n4CCCN3CCCN1CCN(C)CC1] |
| 46 | GSA1102 | 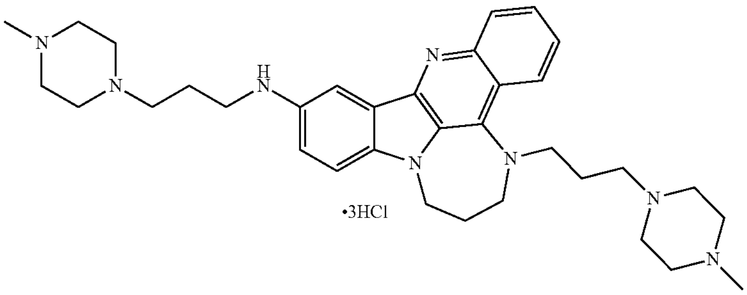 |

TABLE I-continued
Structures of Quindoline compounds
| Compound Number | | Structure |
|---|---|---|
| 47 | GSA1106 | 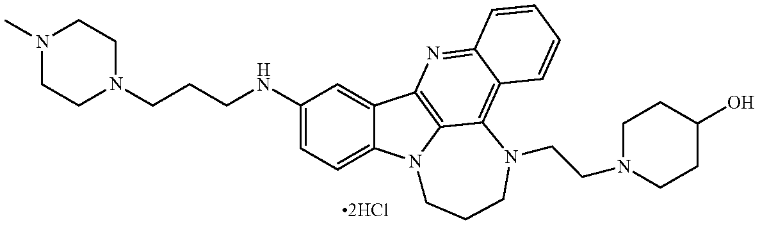 [SMILES: CN1CCN(CCCNc2ccc3c(c2)c2nc4ccccc4c4c2n3CCCN4CCN2CCC(O)CC2)CC1] |
| 48 | GSA1022 | 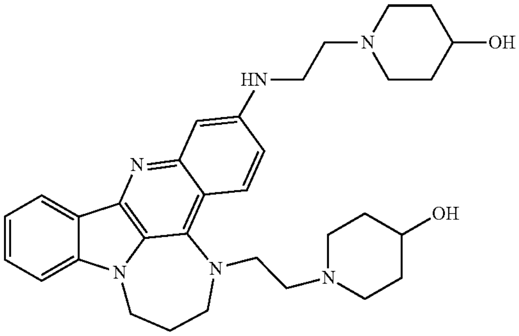 [SMILES: OC1CCN(CCNc2ccc3c4c5c(nc3c2)c2ccccc2n5CCCN4CCN2CCC(O)CC2)CC1] |
| 49 | GSA1103 | 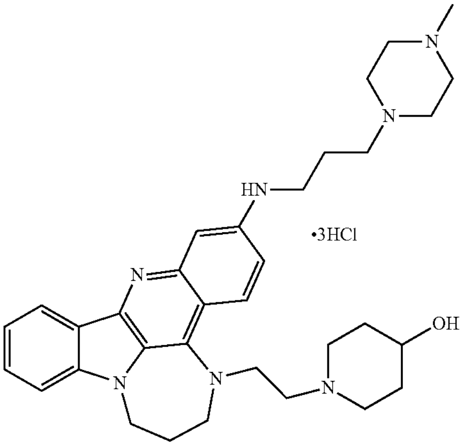 [SMILES: CN1CCN(CCCNc2ccc3c4c5c(nc3c2)c2ccccc2n5CCCN4CCN2CCC(O)CC2)CC1] |
| 50 | GSA0262 | 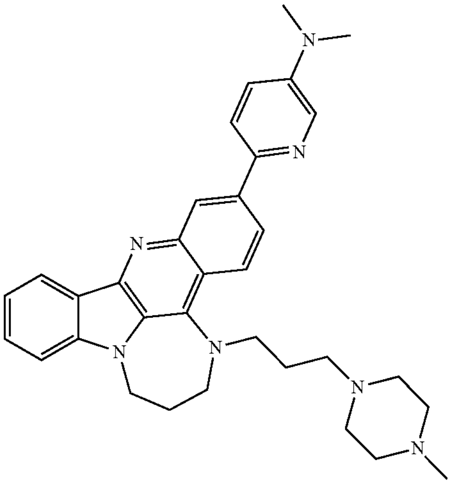 [SMILES: CN1CCN(CCCN2CCCn3c4ccccc4c4nc5cc(-c6ccc(N(C)C)cn6)ccc5c2c43)CC1] |

TABLE I-continued
| Structures of Quindoline compounds | | |
|---|---|---|
| Compound Number | | Structure |
| 51 | GSA1401 | 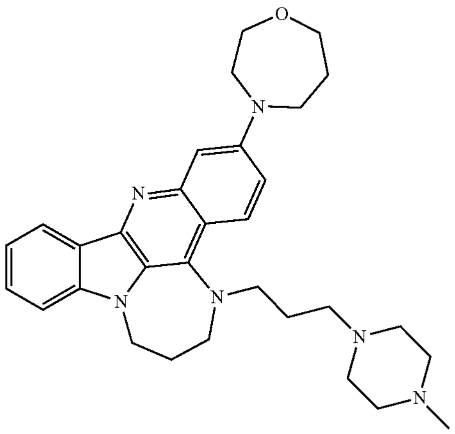 [SMILES: CN1CCN(CCCN2CCCn3c4ccccc4c4nc5cc(N6CCCOCC6)ccc5c2c43)CC1] |
| 52 | GSA1402 | 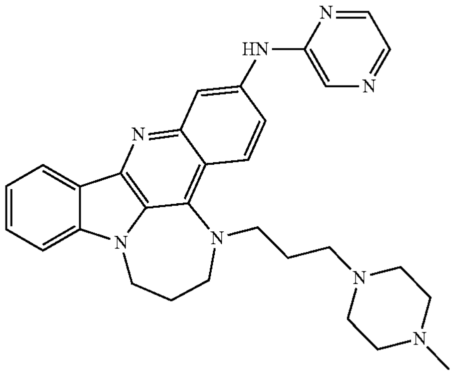 [SMILES: CN1CCN(CCCN2CCCn3c4ccccc4c4nc5cc(Nc6cnccn6)ccc5c2c43)CC1] |
| 53 | GSA1403 | 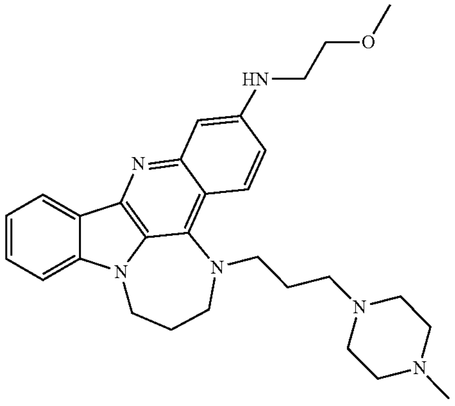 [SMILES: COCCNc1ccc2c3c4c(nc2c1)c1ccccc1n4CCCN3CCCN1CCN(C)CC1] |

TABLE I-continued
| Structures of Quindoline compounds | | |
|---|---|---|
| Compound Number | | Structure |
| 54 | GSA1501 | 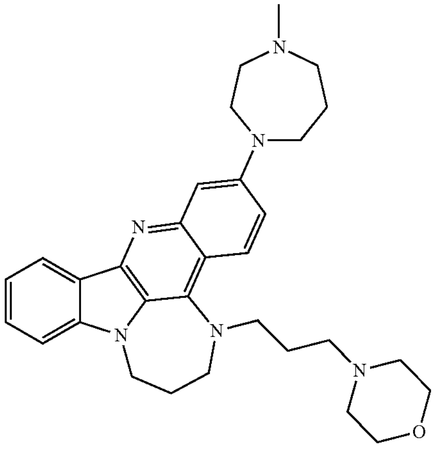 [SMILES: CN1CCCN(c2ccc3c4c5c(nc3c2)c2ccccc2n5CCCN4CCCN2CCOCC2)CC1] |
| 55 | GSA1503 | 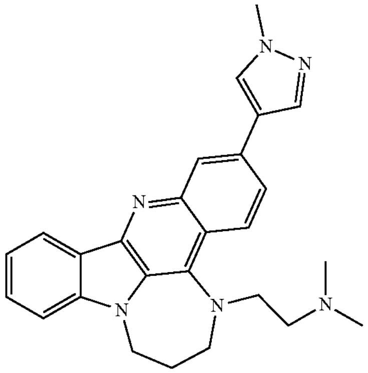 [SMILES: CN(C)CCN1CCCn2c3ccccc3c3nc4cc(-c5cnn(C)c5)ccc4c1c32] |
| 56 | GSA1505 | 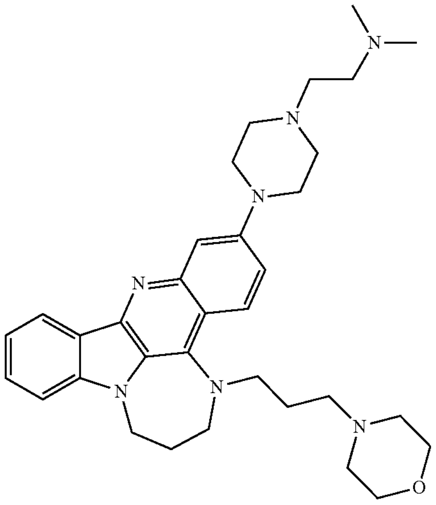 [SMILES: CN(C)CCN1CCN(c2ccc3c4c5c(nc3c2)c2ccccc2n5CCCN4CCCN2CCOCC2)CC1] |

TABLE I-continued
| Structures of Quindoline compounds | | |
|---|---|---|
| Compound Number | | Structure |
| 57 | GSA1509 | 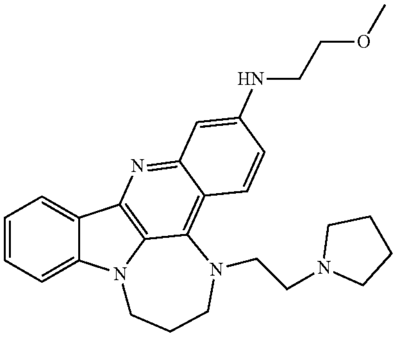 [SMILES: COCCNc1ccc2c3c4c(nc2c1)c1ccccc1n4CCCN3CCN1CCCC1] |
| 58 | GSA1511 | 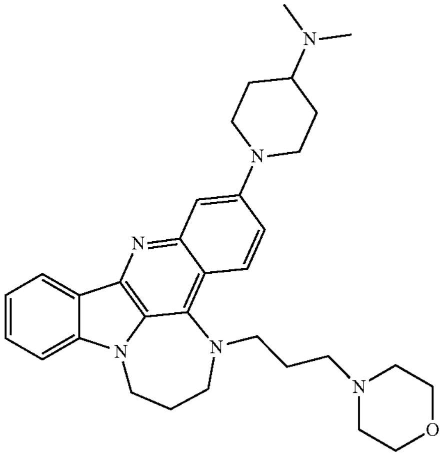 [SMILES: CN(C)C1CCN(c2ccc3c4c5c(nc3c2)c2ccccc2n5CCCN4CCCN2CCOCC2)CC1] |
| 59 | GSA1205 | 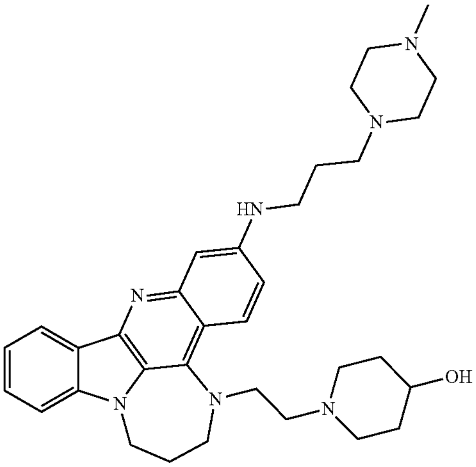 [SMILES: CN1CCN(CCCNc2ccc3c4c5c(nc3c2)c2ccccc2n5CCCN4CCN2CCC(O)CC2)CC1] |

TABLE I-continued
| Structures of Quindoline compounds | | |
|---|---|---|
| Compound Number | | Structure |
| 60 | GSA1206 | 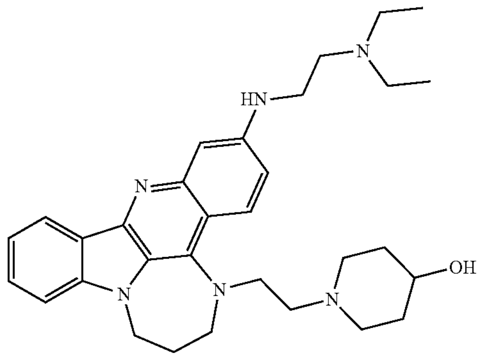 [SMILES: CCN(CC)CCNc1ccc2c3c4c(nc2c1)c1ccccc1n4CCCN3CCN1CCC(O)CC1] |
| 61 | GSA1207 | 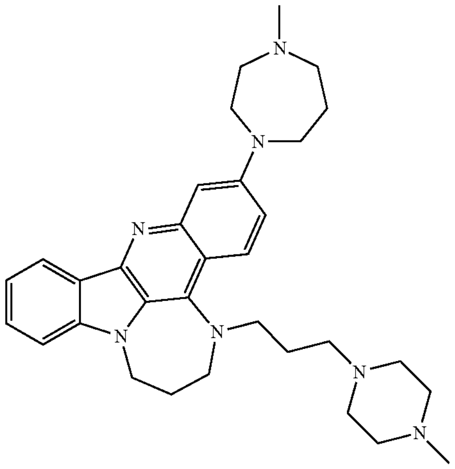 [SMILES: CN1CCN(CCCN2CCCn3c4ccccc4c4nc5cc(N6CCCN(C)CC6)ccc5c2c43)CC1] |
| 62 | GSA1209 | 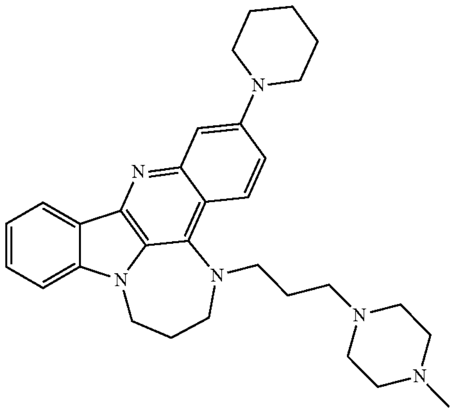 [SMILES: CN1CCN(CCCN2CCCn3c4ccccc4c4nc5cc(N6CCCCC6)ccc5c2c43)CC1] |

TABLE I-continued

| Structures of Quindoline compounds | | |
|---|---|---|
| Compound Number | | Structure |
| 63 | GSA1210 | 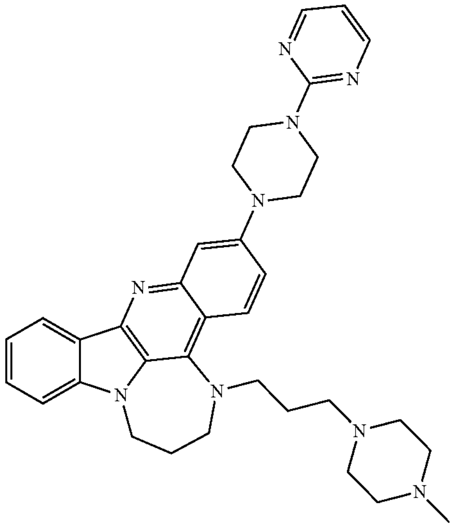 [SMILES: CN1CCN(CCCN2CCCn3c4ccccc4c4nc5cc(N6CCN(c7ncccn7)CC6)ccc5c2c43)CC1] |
| 64 | GSA1211 | 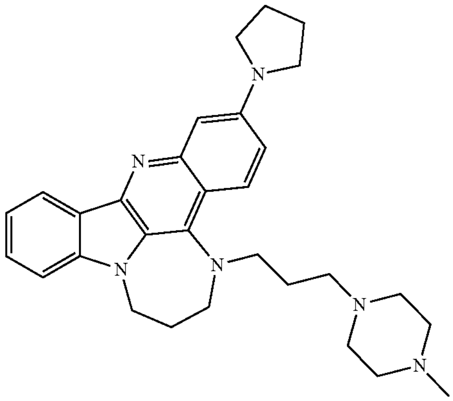 [SMILES: CN1CCN(CCCN2CCCn3c4ccccc4c4nc5cc(N6CCCC6)ccc5c2c43)CC1] |

In a particular embodiment, compounds encompassed within Formula II are provided:

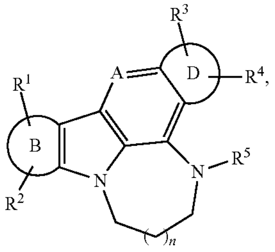

or a pharmaceutically acceptable salt thereof.

Formula II is not limited to a particular chemical structure. In some embodiments, the compound encompassed by Formula II is capable of stabilizing G-quadruplex structures.

In some embodiments, the compound encompassed by Formula II is capable of inhibiting c-Myc activity and/or expression. In some embodiments, the compound encompassed by Formula II is capable of inhibiting c-Myc activity and/or expression through stabilization of G-quadruplex structures related to c-Myc activity and/or expression.

In some embodiments, the compound encompassed by Formula II is capable of inhibiting AR activity and/or expression. In some embodiments, the compound encompassed by Formula II is capable of inhibiting AR activity and/or expression through stabilization of G-quadruplex structures related to AR activity and/or expression. In some embodiments, the compound encompassed by Formula II is capable of inhibiting AR activity and/or expression through stabilization of AR promoter related G-quadruplex structures.

In some embodiments, n is 0, 1, 2, or 3.

In some embodiments, A is —N= or —$N^+(R^A)$=, wherein $R^A$ is $C_1$-$C_6$alkyl, wherein when A is —$N^+(R^A)$=, then the compound further comprises a pharmaceutically acceptable anion.

In some embodiments, the B ring and the D ring are each independently a fused phenyl ring or a 6-membered heteroaryl ring comprising one to four annular nitrogen atoms.

In some embodiments, $R^1$, $R^2$, $R^3$ and $R^4$ are each independently hydrogen, $C_1$-$C_6$alkyl, $C_2$-$C_6$alkenyl, $C_2$-$C_6$alkynyl, $C_3$-$C_8$cycloalkyl, heterocyclyl, aryl, heteroaryl, aryl-aryl, aryl-heteroaryl, aryl-heterocyclyl, heteroaryl-aryl, heterocyclyl-aryl, $C_3$-$C_8$cycloalkyl($C_1$-$C_6$)alkyl, heterocyclyl($C_1$-$C_6$)alkyl, aryl($C_1$-$C_6$)alkyl, heteroaryl ($C_1$-$C_6$)alkyl, or $R^{10}$, wherein the alkyl, alkenyl, alkynyl, cycloalkyl, heterocyclyl, aryl, heteroaryl, aryl-aryl, aryl-heteroaryl, aryl-heterocyclyl, heteroaryl-aryl, heterocyclyl-aryl, cycloalkylalkyl, heterocyclylalkyl, arylalkyl, and heteroarylalkyl groups are each optionally substituted by 1, 2, 3, or 4 $R^{10}$ groups, or $R^1$ and $R^2$ are taken together to form a fused phenyl, monocyclic $C_3$-$C_8$cycloalkyl, monocyclic heterocyclyl, monocyclic aryl, or monocyclic heteroaryl ring, each optionally substituted with 1, 2, 3, or 4 $R^{10}$ groups;

or $R^3$ and $R^4$ are taken together to form a fused phenyl, monocyclic $C_3$-$C_8$cycloalkyl, monocyclic heterocyclyl, monocyclic aryl, or monocyclic heteroaryl ring, each optionally substituted with 1, 2, 3, or 4 $R^{10}$ groups.

In some embodiments, each $R^{10}$ is independently $R^{15}$, $C_1$-$C_6$alkyl, —$C_1$-$C_6$alkyl-$R^{15}$.

In some embodiments, each $R^{15}$ is independently halo, nitro, azido, cyano, nitroso, —OR, —SR, —$NR_2$, —C(O)R, —C(O)OR, —C(O)$NR_2$, —$S(O)_2$R, —$S(O)_2NR_2$, —N(R)C(O)R, —N(R)$S(O)_2$R, —OC(O)R, —OC(O)OR, —N(R)C(O)OR, —N(R)C(O)$NR_2$, or —N(R)C(=NR)$NR_2$.

In some embodiments, $R^5$ is $C_1$-$C_6$alkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

In some embodiments, the alkyl, cycloalkyl, heterocyclyl, cycloalkylalkyl, and heterocyclylalkyl groups are optionally substituted with 1, 2, 3, 4, or 5 groups which are each independently oxo, thia, —$R^{50}$, or —$C_1$-$C_6$alkyl-$R^{50}$.

In some embodiments, the aryl, heteroaryl, arylalkyl, and heteroarylalkyl groups are optionally substituted 1, 2, 3, or 4 groups which are each independently $R^{50}$ or —$C_1$-$C_6$alkyl-$R^{50}$.

In some embodiments, each $R^{50}$ is independently halogen, cyano, nitro, azido, nitroso, —OR, —SR, —$NR_2$, —N($R^N$)C(H)($R^{AA}$)C(O)($R^C$), —N(R)$NR_2$, —C(O)R, —C(O)C(H)($R^{AA}$)N(H)($R^N$), —C(O)OR, —C(O)$NR_2$, —C(O)N($R^N$)—C(H)($R^{AA}$)C(O)$R^C$, —C(=NR)$NR_2$, —$S(O)_2$R, —$S(O)_2NR_2$, —N(R)C(O)R, —N(R)C(O)C(H)($R^{AA}$)N(H)($R^N$), —N(R)$S(O)_2$R, —OC(O)R, —OC(O)OR, —N(R)C(O)OR, —N(R)C(O)$NR_2$, —N(R)C(=NR)$NR_2$, $C_1$-$C_6$alkyl, $C_2$-$C_6$alkenyl, $C_2$-$C_6$alkynyl, $C_3$-$C_8$cycloalkyl, heterocyclyl, aryl, or heteroaryl.

In some embodiments, each R is independently hydrogen, $C_1$-$C_6$alkyl, $C_2$-$C_6$alkenyl, $C_2$-$C_6$alkynyl, $C_3$-$C_8$cycloalkyl, heterocyclyl, aryl, heteroaryl, $C_3$-$C_8$cycloalkyl($C_1$-$C_6$)alkyl heterocyclyl($C_1$-$C_6$)alkyl, aryl($C_1$-$C_6$)alkyl, or heteroaryl ($C_1$-$C_6$)alkyl, wherein the alkyl, alkenyl, alkynyl, cycloalkyl, heterocyclyl, aryl, heteroaryl, cycloalkylalkyl heterocyclylalkyl, arylalkyl, and heteroarylalkyl are each optionally substituted with 1, 2, 3, or 4 $R^{11}$ groups, or two R groups attached to the same nitrogen atom taken together with the nitrogen atom to which they are attached form a heterocyclyl optionally substituted with 1, 2, 3, or 4 $R^{11}$ groups.

In some embodiments, each $R^{11}$ is independently halo, nitro, azido, cyano, nitroso, —$OR^{12}$, —$SR^{12}$, —N($R^{12}$)$_2$, —C(O)$R^{12}$, —C(O)O$R^{12}$, —C(O)N($R^{12}$)$_2$, —$S(O)_2R^{12}$, —$S(O)_2$N($R^{12}$)$_2$, —N($R^{12}$)C(O)$R^{12}$, —N($R^{12}$)$S(O)_2R^{12}$, —OC(O)$R^{12}$, —OC(O)O$R^{12}$, —N($R^{12}$)C(O)O$R^{12}$, —N($R^{12}$)C(O)N($R^{12}$)$_2$, —N($R^{12}$)C(=N$R^{12}$)N($R^{12}$)$_2$, $C_1$-$C_6$alkyl, $C_2$-$C_6$alkenyl, or $C_2$-$C_6$alkynyl.

In some embodiments, each $R^{12}$ is hydrogen or $C_1$-$C_6$alkyl, or two $R^{12}$ groups attached to the same nitrogen atom taken together with the nitrogen atom to which they are attached form a heterocyclyl optionally substituted with 1 or 2 groups that are each independently halo or $C_1$-$C_6$alkyl.

In some embodiments, each $R^N$ is independently hydrogen or —C(O)C(H)($R^{AA}$)NH($R^{N2}$).

In some embodiments, each $R^C$ is independently —OH or —N($R^{N2}$)C(H)($R^{AA}$)COOH.

In some embodiments, $R^{N2}$ is (i) hydrogen or (ii) $R^{N2}$ and $R^{AA}$ taken together with the atoms to which they are attached form a 4-8 membered heterocyclyl optionally substituted with one or two $R^{A1}$ groups.

In some embodiments, each $R^{AA}$ is hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with 1, 2, 3, 4, or 5 $R^{A1}$ groups, wherein each $R^{A1}$ is independently halo, cyano, —$OR^{A2}$, —$SR^{A2}$, —N($R^{A2}$)$_2$, —C(O)O$R^{A2}$, —C(O)N($R^{A2}$)$_2$, —N($R^{A2}$)C(=N$R^{A2}$)N($R^{A2}$)$_2$, or $C_1$-$C_6$alkyl, wherein each $R^{A2}$ is hydrogen or $C_1$-$C_6$alkyl;

or $R^N$ and $R^{AA}$ taken together with the atoms to which they are attached form a 4-8 membered heterocyclyl optionally substituted with one or two $R^{A1}$ groups.

The invention further comprises subgenera of compounds encompassed within Formula II in which the substituents are selected as any and all combinations of structural formula II, A, $R^1$-$R^4$, and $R^5$ as defined herein, including without limitation, the following:

(IIa)

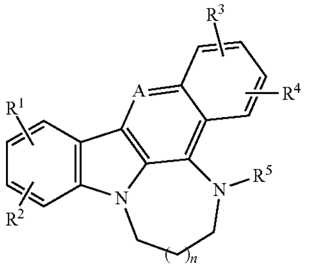

(IIb)

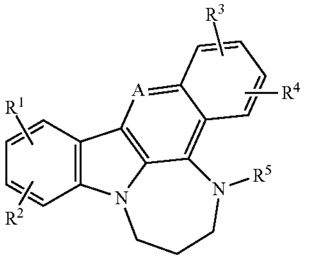

(IIc)

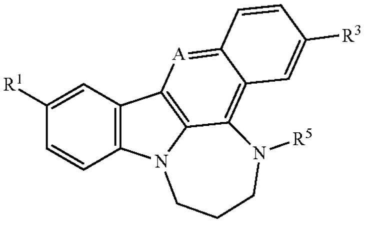

-continued (IId)

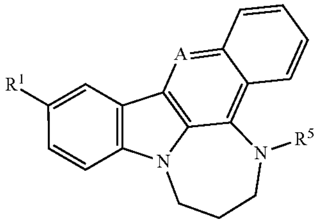

or (IIe)

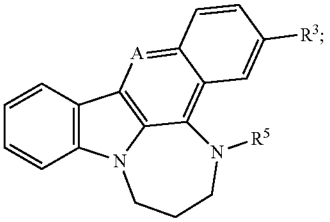

wherein, when present, each B is independently —N— or —C(H)—, and wherein when B is —C(H)—, then B can be optionally substituted with $R^1$, $R^2$, $R^3$, or $R^4$ when the ring in which each B is present is allowed to be substituted by $R^1$-$R^4$ as defined in the preceding formulae.

In some embodiments, A is selected from one of the following groups (a)-(c):

(a) A is —N=.

(b) A is —$N^+(R^A)$=, wherein $R^A$ is $C_1$-$C_6$alkyl, and wherein the compound further comprises a pharmaceutically acceptable anion.

(c) A is —$N^+(R^A)$=, and the pharmaceutically acceptable anion is a halide.

In some embodiments, $R^1$-$R^4$ are selected from one of the following groups (d)-(ss):

(d) One of $R^1$, $R^2$, $R^3$ and $R^4$ is —$OR^{16}$, —$SR^{16}$, or —$N(H)(R^{16})$, wherein $R^{16}$ is $C_1$-$C_6$alkyl, or $C_1$-$C_6$alkyl-$R_{17}$, heterocyclyl($C_1$-$C_6$)alkyl, aryl($C_1$-$C_6$) alkyl, or heteroaryl($C_1$-$C_6$)alkyl, wherein $R^{17}$ is —$OR^{18}$, —$SR^{18}$, —$N(R^{18})_2$, —$C(O)R^{18}$, —$C(O)OR^{18}$, —$C(O)N(R^{18})_2$, —$S(O)_2R^{18}$, —$S(O)_2N(R^{18})_2$, —$N(R^{18})C(O)R^{18}$, —$N(R^{18})S(O)_2R^{18}$, —$OC(O)R^{18}$, —$OC(O)OR^{18}$, —$N(R^{18})C(O)OR^{18}$, —$N(R^{18})C(O)N(R^{18})_2$, or —$N(R^{18})C(=NR^{18})N(R^{18})_2$, wherein each $R^{18}$ is hydrogen or $C_1$-$C_6$alkyl.

(e) $R^2$ and $R^4$ are each hydrogen; and $R^1$ and $R^3$ are each independently —$OR^{16}$, —$SR^{16}$, or —$N(H)(R^{16})$, wherein $R^{16}$ is $C_1$-$C_6$alkyl, or —$C_1$-$C_6$alkyl-$R^{17}$, heterocyclyl($C_1$-$C_6$)alkyl, aryl($C_1$-$C_6$)alkyl, or heteroaryl ($C_1$-$C_6$)alkyl, wherein $R^{17}$ is —$OR^{18}$, —$SR^{18}$, —$N(R^{18})_2$, —$C(O)R^{18}$, —$C(O)OR^{18}$, —$C(O)N(R^{18})_2$, —$S(O)_2R^{18}$, —$S(O)_2N(R^{18})_2$, —$N(R^{18})C(O)R^{18}$, —$N(R^{18})S(O)_2R^{18}$, —$OC(O)R^{18}$, —$OC(O)OR^{18}$, —$N(R^{18})C(O)OR^{18}$, —$N(R^{18})C(O)N(R^{18})_2$, or —$N(R^{18})C(=NR^{18})N(R^{18})_2$, wherein each $R^{18}$ is hydrogen or $C_1$-$C_6$alkyl.

(f) $R^2$ and $R^4$ are each hydrogen; one of $R^1$ and $R^3$ is —$OR^{16}$, —$SR^{16}$, or —$N(H)(R^{16})$, wherein $R^{16}$ is $C_1$-$C_6$alkyl, or —$C_1$-$C_6$alkyl-$R^{17}$, heterocyclyl($C_1$-$C_6$) alkyl, aryl($C_1$-$C_6$)alkyl, or heteroaryl($C_1$-$C_6$)alkyl, wherein $R^{17}$ is —$OR^{18}$, —$SR^{18}$, —$N(R^{18})_2$, —$C(O)R^{18}$, —$C(O)OR^{18}$, —$C(O)N(R^{18})_2$, —$S(O)_2R^{18}$, —$S(O)_2N(R^{18})_2$, —$N(R^{18})C(O)R^{18}$, —$N(R^{18})S(O)_2R^{18}$, —$OC(O)R^{18}$, —$OC(O)OR^{18}$, —$N(R^{18})C(O)OR^{18}$, —$N(R^{18})C(O)N(R^{18})_2$, or —$N(R^{18})C(=NR^{18})N(R^{18})_2$, wherein each $R^{18}$ is hydrogen or $C_1$-$C_6$alkyl; and the other of $R^1$ and $R^3$ is hydrogen.

(g) Group (f), wherein $R^1$ is hydrogen.

(h) Group (f), wherein $R^3$ is hydrogen.

(i) $R^2$ and $R^4$ are each hydrogen; and $R^1$ and $R^3$ are each independently —$N(H)R^{16}$, wherein $R^{16}$ is $C_1$-$C_6$alkyl, or —$C_1$-$C_6$alkyl-$R^{17}$, heterocyclyl($C_1$-$C_6$)alkyl, aryl ($C_1$-$C_6$)alkyl, or heteroaryl($C_1$-$C_6$)alkyl, wherein $R^{17}$ is —$OR^{18}$, —$SR^{18}$, —$N(R^{18})_2$, —$C(O)R^{18}$, —$C(O)OR^{18}$, —$C(O)N(R^{18})_2$, —$S(O)_2R^{18}$, —$S(O)_2N(R^{18})_2$, —$N(R^{18})C(O)R^{18}$, —$N(R^{18})S(O)_2R^{18}$, —$OC(O)R^{18}$, —$OC(O)OR^{18}$, —$N(R^{18})C(O)OR^{18}$, —$N(R^{18})C(O)N(R^{18})_2$, or —$N(R^{18})C(=NR^{18})N(R^{18})_2$, wherein each $R^{18}$ is hydrogen or $C_1$-$C_6$alkyl.

(j) $R^2$ and $R^4$ are each hydrogen; one of $R^1$ and $R^3$ is —$N(H)R^{16}$, wherein $R^{16}$ is $C_1$-$C_6$alkyl, or —$C_1$-$C_6$alkyl-$R^{17}$, heterocyclyl($C_1$-$C_6$)alkyl, aryl($C_1$-$C_6$)alkyl, or heteroaryl($C_1$-$C_6$)alkyl, wherein $R^{17}$ is —$OR^{18}$, —$SR^{18}$, —$N(R^{18})_2$, —$C(O)R^{18}$, —$C(O)OR^{18}$, —$C(O)N(R^{18})_2$, —$S(O)_2R^{18}$, —$S(O)_2N(R^{18})_2$, —$N(R^{18})C(O)R^{18}$, —$N(R^{18})S(O)_2R^{18}$, —$OC(O)R^{18}$, —$OC(O)OR^{18}$, —$N(R^{18})C(O)OR^{18}$, —$N(R^{18})C(O)N(R^{18})_2$, or —$N(R^{18})C(=NR^{18})N(R^{18})_2$, wherein each $R^{18}$ is hydrogen or $C_1$-$C_6$alkyl; and the other of $R^1$ and $R^3$ is hydrogen.

(k) Group (j), wherein $R^1$ is hydrogen.

(l) Group (j), wherein $R^3$ is hydrogen.

(m) $R^2$ and $R^4$ are each hydrogen; and $R^1$ and $R^3$ are each independently —$N(H)R^{16}$, wherein $R^{16}$ is —$C_1$-$C_6$alkyl-$R^{17}$ or heterocyclyl($C_1$-$C_6$)alkyl, wherein $R^{17}$ is —$OR^{18}$, —$SR^{18}$, —$N(R^{18})_2$, —$N(R^{18})C(O)R^{18}$, —$N(R^{18})S(O)_2R^{18}$, —$OC(O)R^{18}$, —$OC(O)OR^{18}$, —$N(R^{18})C(O)OR^{18}$, —$N(R^{18})C(O)N(R^{18})_2$, or —$N(R^{18})C(=NR^{18})N(R^{18})_2$, wherein each $R^{18}$ is hydrogen or $C_1$-$C_6$alkyl.

(n) $R^2$ and $R^4$ are each hydrogen; one of $R^1$ and $R^3$ is —$N(H)R^{16}$, wherein $R^{16}$ is —$C_1$-$C_6$alkyl-$R^{17}$ or heterocyclyl($C_1$-$C_6$)alkyl, wherein $R^{17}$ is —$OR^B$, —$SR^{18}$, —$N(R^{18})_2$, —$N(R^{18})C(O)R^{18}$, —$N(R^{18})S(O)_2R^{18}$, —$OC(O)R^{18}$, —$OC(O)OR^{18}$, —$N(R^{18})C(O)OR^{18}$, —$N(R^{18})C(O)N(R^{18})_2$, or —$N(R^{18})C(=NR^{18})N(R^{18})_2$, wherein each $R^{18}$ is hydrogen or $C_1$-$C_6$alkyl, and the other of $R^1$ and $R^3$ is hydrogen.

(o) Group (n), wherein $R^1$ is hydrogen.

(p) Group (n), wherein $R^3$ is hydrogen.

(q) One of $R^1$, $R^2$, $R^3$ and $R^4$ is heterocyclyl, aryl, or heteroaryl, wherein the heterocyclyl, aryl, and heteroaryl groups are each optionally substituted by a one group which is $R^{20}$, $C_1$-$C_6$alkyl, or —$C_1$-$C_6$alkyl-$R^{20}$, wherein $R^{20}$ is —$OR^{21}$, —$SR^{21}$, —$N(R^{21})_2$, —$C(O)R^{21}$, —$C(O)OR^{21}$, —$C(O)N(R^{21})_2$, —$S(O)_2R^{21}$, —$S(O)_2N(O)_2$, —$N(R^{21})C(O)R^{21}$, —$N(R^{21})S(O)_2R^{21}$, —$OC(O)R^{21}$, —$OC(O)OR^{21}$, —$N(R^{21})C(O)OR^{21}$, —$N(R^{21})C(O)N(R^{21})_2$, or —$N(R^{21})C(=NR^{21})N(R^{21})_2$, wherein each $R^{21}$ is independently hydrogen; $C_1$-$C_6$alkyl; or heterocyclyl optionally substituted with 1, 2, 3, or 4 $R^{11}$ groups.

(r) Group (q), wherein $R^2$ and $R^4$ are hydrogen.

(s) Group (q), wherein $R^1$, $R^2$, and $R^4$ are hydrogen.

(t) Group (q), wherein $R^2$, $R^3$, and $R^4$ are hydrogen.

(u) One of $R^1$, $R^2$, $R^3$ and $R^4$ is heterocyclyl, aryl, or heteroaryl, wherein the heterocyclyl, aryl, and heteroaryl groups are each optionally substituted by a one group which is $R^{20}$, $C_1$-$C_6$alkyl, or —$C_1$-$C_6$alkyl-$R^{20}$, wherein $R^{20}$ is —$OR^{21}$, —$SR^{21}$, —$N(R^{21})_2$, —$C(O)R^{21}$, —$C(O)OR^{21}$, —$C(O)N(R^{21})_2$, —$S(O)_2R^{21}$, —$S(O)_2N(R^{21})_2$, wherein each $R^{21}$ is independently hydrogen; $C_1$-$C_6$alkyl; or heterocyclyl optionally substituted with 1, 2, 3, or 4 $R^{11}$ groups.

(v) Group (u), wherein $R^2$ and $R^4$ are hydrogen.

(w) Group (u), wherein $R^1$, $R^2$, and $R^4$ are hydrogen.

(x) Group (u), wherein $R^2$, $R^3$, and $R^4$ are hydrogen.

(y) At least one of $R^1$, $R^2$, $R^3$ and $R^4$ is

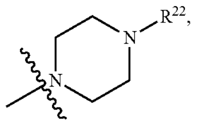

wherein $R^{22}$ is —$C(O)R^{21}$, —$C(O)OR^{21}$, —$C(O)N(R^{21})_2$, —$S(O)_2R^{21}$, —$S(O)_2N(R^{21})_2$, $C_1$-$C_6$alkyl, or —$C_1$-$C_6$alkyl-$R^{20}$, wherein $R^{20}$ is —$OR^{21}$, —$SR^{21}$, —$N(R^{21})_2$, —$C(O)R^{21}$, —$C(O)OR^{21}$, —$C(O)N(R^{21})_2$, —$S(O)_2R^{21}$, —$S(O)_2N(R^{21})_2$, and each $R^{21}$ is independently hydrogen; $C_1$-$C_6$alkyl; or heterocyclyl optionally substituted with 1, 2, 3, or 4 $R^{11}$ groups.

(z) Group (y), wherein $R^1$ and $R^3$ are each independently

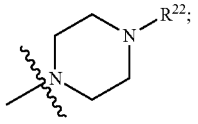

and $R^2$ and $R^4$ are hydrogen.

(aa) Group (y), wherein $R^1$, $R^2$, and $R^4$ are hydrogen.

(bb) Group (y), wherein $R^2$, $R^3$, and $R^4$ are hydrogen.

(cc) At least one of $R^1$, $R^2$, $R^3$ and $R^4$ is

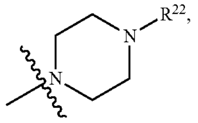

wherein $R^{22}$ is $C_1$-$C_6$alkyl, or —$C_1$-$C_6$alkyl-$R^{20}$ wherein $R^{20}$ is —$OR^{21}$, —$SR^{21}$, —$N(R^{21})_2$, —$N(R^{21})C(O)R^{21}$, —$N(R^{21})S(O)_2R^{21}$, —$OC(O)R^{21}$, —$OC(O)OR^{21}$, —$N(R^{21})C(O)OR^{21}$, —$N(R^{21})C(O)N(R^{21})_2$, or —$N(R^{21})C(=NR^{21})N(R^{21})_2$, wherein each $R^{21}$ is independently hydrogen; $C_1$-$C_6$alkyl; or heterocyclyl optionally substituted with 1, 2, 3, or 4 $R^{11}$ groups.

(dd) Group (cc), wherein $R^1$ and $R^3$ are each independently

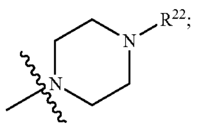

and $R^2$ and $R^4$ are hydrogen.

(ee) Group (cc), wherein $R^1$, $R^2$, and $R^4$ are hydrogen.

(ff) Group (cc), wherein $R^2$, $R^3$, and $R^4$ are hydrogen.

(gg) At least one of $R^1$, $R^2$, $R^3$ and $R^4$ is

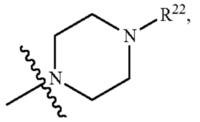

wherein $R^{22}$ is $C_1$-$C_6$alkyl, or —$C_1$-$C_6$alkyl-$R^{20}$, wherein $R^{20}$ is —$OR^{21}$, —$SR^{21}$, or —$N(R^{21})_2$, wherein each $R^{21}$ is independently hydrogen; $C_1$-$C_6$alkyl; or heterocyclyl optionally substituted with 1, 2, 3, or 4 $R^{11}$ groups.

(hh) Group (gg), wherein $R^1$ and $R^3$ are each independently

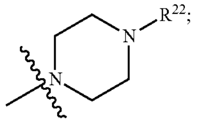

and $R^2$ and $R^4$ are hydrogen.

(ii) Group (gg), wherein $R^1$, $R^2$, and $R^4$ are hydrogen.

(jj) Group (gg), wherein $R^2$, $R^3$, and $R^4$ are hydrogen.

(kk) At least one of $R^1$, $R^2$, $R^3$ and $R^4$ is

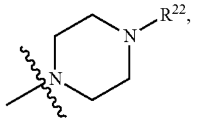

wherein $R^{22}$ is —$C(O)R^{21}$ or —$S(O)_2R^{21}$ each $R^{21}$ is independently hydrogen; $C_1$-$C_6$alkyl; or heterocyclyl optionally substituted with 1, 2, 3, or 4 $R^{11}$ groups.

(ll) Group (kk), wherein $R^1$ and $R^3$ are each independently

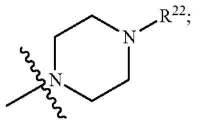

and $R^2$ and $R^4$ are hydrogen.

(mm) Group (kk), wherein $R^1$, $R^2$, and $R^4$ are hydrogen.

(nn) Group (kk), wherein $R^2$, $R^3$, and $R^4$ are hydrogen.

(oo) Any one of groups q-(nn), wherein each $R^{21}$ is independently hydrogen or $C_1$-$C_6$alkyl.

(pp) At least one of $R^1$, $R^2$, $R^3$ and $R^4$ is

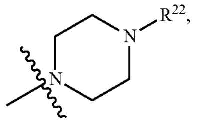

wherein $R^{22}$ is —$C(O)R^{21}$ or —$S(O)_2R^{21}$, wherein $R^{21}$ is heterocyclyl optionally substituted with 1, 2, 3, or 4 $R^{11}$ groups.

(qq) Group (pp), wherein $R^1$ and $R^3$ are each independently

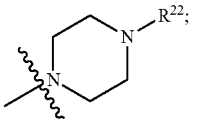

and $R^2$ and $R^4$ are hydrogen.

(rr) Group (pp), wherein $R^1$, $R^2$, and $R^4$ are hydrogen.

(ss) Group (pp), wherein $R^2$, $R^3$, and $R^4$ are hydrogen.

In some embodiments, $R^5$ is selected from one of the following groups (tt)-(zzz):

(tt) $R^5$ is —$C_1$-$C_6$alkyl-$R^{50}$, wherein $R^{50}$ is —OR, —SR, —$NR_2$, —N(R)C(H)($R^{AA}$)C(O)($R^C$), —N(R)$NR_2$, —N(R)C(O)R, —N(R)C(O)C(H)($R^{AA}$)N(H)($R^N$), —N(R)S(O)$_2$R, —OC(O)R, —OC(O)OR, —N(R)C(O)OR, —N(R)C(O)$NR_2$, or —N(R)C(=NR)$NR_2$.

(uu) $R^5$ is —$C_1$-$C_6$alkyl-$R^{50}$, wherein $R^{50}$ is —N(H)C(O)$R^{53}$, —N(H)S(O)$_2R^{53}$, —OC(O)$R^{53}$, —OC(O)O$R^{53}$, —N(H)C(O)O$R^{53}$, —N(H)C(O)N(H)$R^{53}$, wherein $R^{53}$ is $C_1$-$C_6$alkyl, $C_3$-$C_8$cycloalkyl, heterocyclyl, aryl, or heteroaryl, each optionally substituted with 1 or 2 $R^{11}$ groups.

(vv) $R^5$ is —$C_1$-$C_6$alkyl-$R^{50}$, wherein $R^{50}$ is —N(H)C(O)$R^{53}$, —N(H)S(O)$_2R^{53}$, —OC(O)$R^{53}$, —OC(O)O$R^{53}$, —N(H)C(O)O$R^{53}$, —N(H)C(O)N(H)$R^{53}$, wherein $R^{53}$ is $C_1$-$C_6$alkyl, $C_3$-$C_8$cycloalkyl, heterocyclyl, aryl, or heteroaryl.

(ww) Group (uu), wherein $R^{53}$ is $C_1$-$C_6$alkyl, $C_3$-$C_8$cycloalkyl, heterocyclyl, aryl, or heteroaryl, each optionally substituted with 1 or 2 groups which are each independently halo, —O$R^{12}$, —S$R^{12}$, —N($R^{12}$)$_2$, or $C_1$-$C_6$alkyl, wherein each $R^{12}$ is hydrogen or $C_1$-$C_6$alkyl.

(xx) Group (uu), wherein $R^{53}$ is heterocyclyl optionally substituted with 1 or 2 groups which are each independently halo, —O$R^{12}$, —S$R^{12}$)$_2$, —N($R^{12}$)$_2$, or $C_1$-$C_6$alkyl, wherein each $R^{12}$ is hydrogen or $C_1$-$C_6$alkyl.

(yy) Group (uu), wherein $R^{53}$ is pyrrolidinyl, tetrahydrofuranyl, tetrahydrothienyl, imidazolidinyl, oxazolidinyl, thiazolidinyl, piperidinyl, piperazinyl, morpholinyl, thiomorpholinyl, azepanyl, diazepanyl, pyrrolinyl, imidazolinyl, oxazolinyl, or thiazolinyl, each optionally substituted with 1 or 2 groups which are each independently halo, —O$R^{12}$, —S$R^{12}$, —N($R^{12}$)$_2$, or $C_1$-$C_6$alkyl, wherein each $R^{12}$ is hydrogen or $C_1$-$C_6$alkyl.

(zz) Group (uu), wherein $R^{53}$ is pyrrolidinyl, imidazolidinyl, piperidinyl, piperazinyl, azepanyl, or diazepanyl, each optionally substituted with 1 or 2 groups which are each independently halo, —O$R^{12}$, —S$R^{12}$, —N($R^{12}$)$_2$, or $C_1$-$C_6$alkyl, wherein each $R^{12}$ is hydrogen or $C_1$-$C_6$alkyl.

(aaa) $R^5$ is heterocyclyl($C_1$-$C_6$)alkyl optionally substituted with 1, 2, 3, 4, or 5 groups which are each independently oxo, thia, or —$R^{50}$.

(bbb) $R^5$ is heterocyclyl($C_1$-$C_6$)alkyl optionally substituted with 1, 2, or 3 groups which are each independently oxo, thia, or —$R^{50}$.

(ccc) $R^5$ is of the formula,

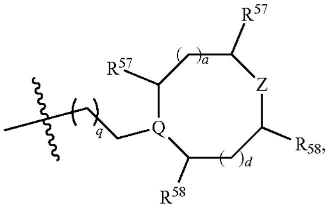

wherein a and d are each independently 0, 1, or 2;

q is 0, 1, 2, 3, 4 or 5;

Q is —N— or —C(H)—;

Z is a bond, —O—, —S—, —C(O)—, or —N($R^{60}$)—, wherein $R^{60}$ is hydrogen, $C_1$-$C_6$alkyl, aryl, heteroaryl, heterocyclyl, $C_3$-$C_8$cycloalkyl, aryl($C_1$-$C_6$)alkyl, heteroaryl($C_1$-$C_6$)alkyl, heterocyclyl($C_1$-$C_6$)alkyl, $C_3$-$C_8$cycloalkyl($C_1$-$C_6$)alkyl, —$C_1$-$C_6$alkyl-OR, —$C_1$-$C_6$alkyl-SR, —$C_1$-$C_6$alkyl-N(R)$_2$, —COR, —CON$R_2$, —C(O)C(H)($R^{AA}$)N(H)($R^N$), —C(=NR)N$R_2$, —SO$_2$R, —COOR; and each $R^{57}$ and $R^{58}$ are independently hydrogen, $C_1$-$C_6$alkyl, aryl, heteroaryl, heterocyclyl, $C_3$-$C_8$cycloalkyl, —OR, —N$R_2$, —N(R)C(O)N$R_2$, oxo, —COOH, —CON$R_2$, —C(O)C(H)($R^{AA}$)N(H)($R^N$), or —N(R)C(H)($R^{AA}$)C(O)($R^C$), or when a is 0, then both $R^{57}$ groups can be taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups;

or when d is 0, both $R^{58}$ groups can be taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(ddd) Group (ccc) wherein Q is —N—.

(eee) Group (ccc), wherein Q is —N—; and a is 0.

(fff) Group (ccc), wherein Q is —N—; and a and d are each 0.

(ggg) Group (ccc), wherein Q is —N— and Z is a bond or —O—.

(hhh) Group (ccc) wherein Q is —N—; a is 0; and both $R^{57}$ groups taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups; and each $R^{58}$ is independently hydrogen, $C_1$-$C_6$alkyl, aryl, heteroaryl, heterocyclyl, $C_3$-$C_8$cycloalkyl, —OR, —N$R_2$, —N(R)C(O)N$R_2$, oxo, —COOH, —CON$R_2$, —C(O)C(H)($R^{AA}$)N(H)($R^N$), or —N(R)C(H)($R^{AA}$)C(O)($R^C$).

(iii) Group (hhh), wherein each $R^{58}$ is independently hydrogen.

(jjj) Group (hhh), wherein both $R^{57}$ groups taken together with the carbon atoms to which they are attached form a fused phenyl, 5 or 6-membered monocyclic heteroaryl, 5 or 6 membered monocyclic heterocyclyl, or a $C_5$-$C_6$cycloalkyl, wherein the fused phenyl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(kkk) Group (hhh), wherein d is 0 and both $R^{58}$ groups taken together with the carbon atoms to which they are attached form a fused aryl, heteroaryl, heterocyclyl, or $C_3$-$C_8$cycloalkyl, wherein the fused aryl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(lll) Group (kkk), wherein both $R^{57}$ groups taken together with the carbon atoms to which they are attached and both $R^{58}$ groups taken together with the carbon atoms to which they are attached independently form a fused phenyl, 5 or 6-membered monocyclic heteroaryl, 5 or 6 membered monocyclic heterocyclyl, or $C_5$-$C_6$cycloalkyl, wherein the fused phenyl and heteroaryl groups are each optionally substituted with 1 or 2 $R^{50}$ groups; and wherein the fused heterocyclyl and cycloalkyl groups are each optionally substituted with 1 or 2 oxo, thia, or $R^{50}$ groups.

(mmm) Group (kkk), wherein both $R^{57}$ groups taken together with the carbon atoms to which they are attached and both $R^{58}$ groups taken together with the carbon atoms to which they are attached independently form a fused phenyl, 5 or 6-membered monocyclic heteroaryl, 5 or 6 membered monocyclic heterocyclyl, or $C_5$-$C_6$cycloalkyl, wherein the fused phenyl and heteroaryl groups are each optionally substituted with 1 or 2 $R^{70}$ groups; and wherein the fused heterocyclyl and cycloalkyl groups are each optionally substituted with 1 or 2 oxo, thia, or $R^{70}$ groups, wherein each $R^{70}$ is independently halogen, $C_1$-$C_6$alkyl, $-OR^{65}$, $-SR^{65}$, $-N(R^{65})_2$, $-C(O)R^{65}$, $-C(O)OR^{65}$, $-C(O)N(R^{65})_2$, $-S(O)_2R^{65}$, $-S(O)_2N(R^{65})_2$, $-N(R^{65})C(O)R^{65}$, $-N(R^{65})S(O)_2R^{65}$, $-OC(O)R^{65}$, $-OC(O)OR^{65}$, $-N(R)C(O)OR^{65}$, $-N(R^{65})C(O)N(R^{65})_2$, wherein each $R^{65}$ is independently hydrogen or $C_1$-$C_6$ alkyl.

(ooo) $R^5$ is $-(CH_2)_{1-6}-R^{61}$, wherein $R^{61}$ is a group which is

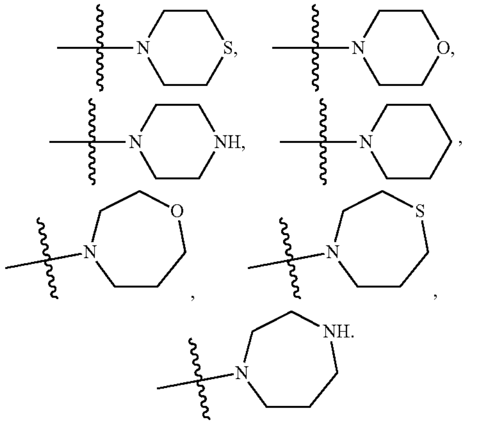

or (ppp) $R^5$ is $-(CH_2)_{1-6}-R^{61}$, wherein $R^{61}$ is a group which is

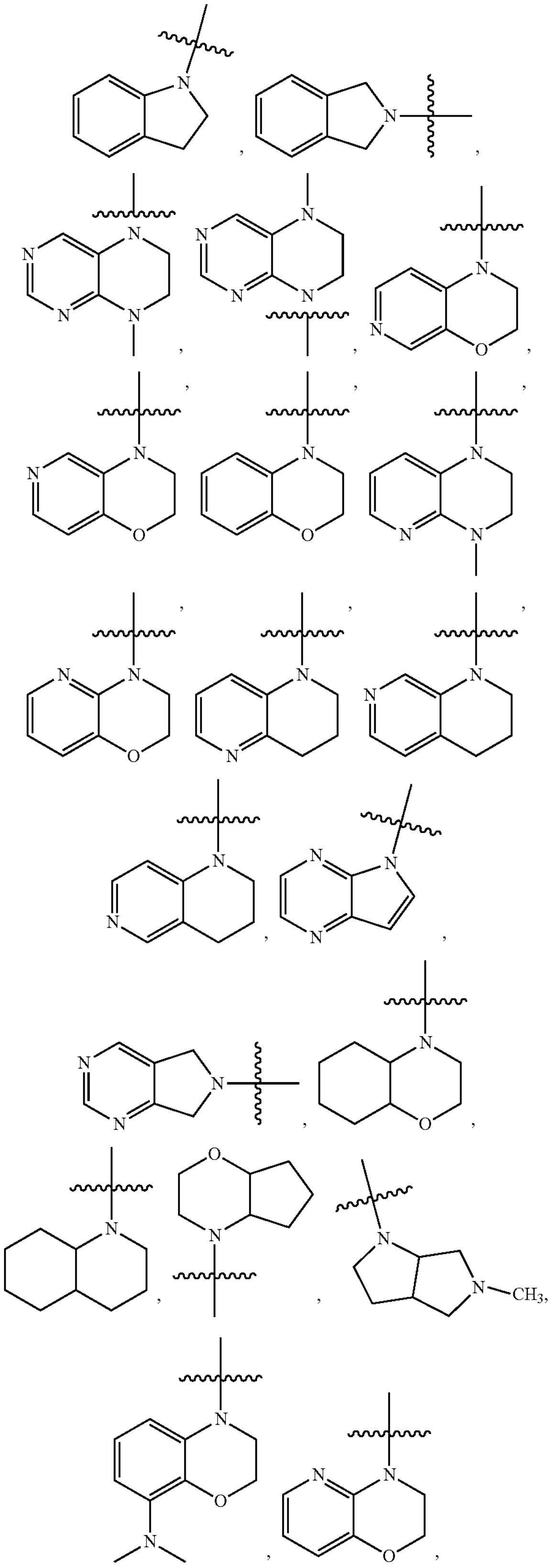

-continued

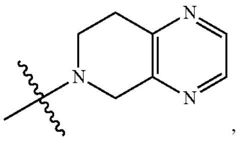, 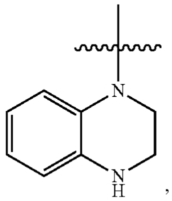,

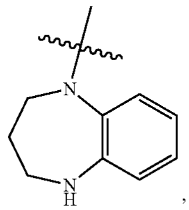, 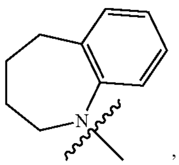, or

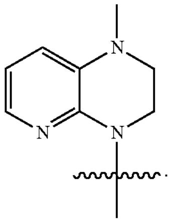.

(rrr) $R^5$ is $—(CH_2)_m—N(H)R^{56}$, wherein m is 2, 3, 4, 5, or 6, and $R^{56}$ is aryl or heteroaryl, each optionally substituted with 1, 2, 3, or 4 groups which are each independently $R^{50}$.

(sss) $R^5$ is $—(CH_2)_m—N(H)R^{56}$, wherein m is 2, 3, 4, 5, or 6, and $R^{56}$ is phenyl or a mono or bicyclic heteroaryl, each optionally substituted with 1, 2, 3, or 4 groups which are each independently $R^{50}$.

(ttt) $R^5$ is $—(CH_2)_m—N(H)R^{56}$, wherein m is 2, 3, 4, 5, or 6, and $R^{56}$ is phenyl optionally substituted with 1, 2, 3, or 4 groups which are each independently $R^{50}$.

(uuu) $R^5$ is $—(CH_2)_m—N(H)R^{56}$, wherein m is 2, 3, 4, 5, or 6, and $R^{56}$ is a mono or bicyclic heteroaryl, each optionally substituted with 1, 2, 3, or 4 groups which are each independently $R^{50}$.

(vvv) $R^5$ is $—(CH_2)_m—N(H)R^{56}$, wherein m is 2 or 3, and $R^{56}$ is aryl or heteroaryl, each optionally substituted with 1, 2, 3, or 4 groups which are each independently $R^{50}$.

(www) $R^5$ is $—(CH_2)_m—N(H)R^{56}$, wherein m is 2 or 3, and $R^{56}$ is phenyl or a mono or bicyclic heteroaryl, each optionally substituted with 1, 2, 3, or 4 groups which are each independently $R^{50}$.

(xxx) $R^5$ is $—(CH_2)_m—N(H)R^{56}$, wherein m is 2 or 3, and $R^{56}$ is phenyl optionally substituted with 1, 2, 3, or 4 groups which are each independently $R^{50}$.

(yyy) $R^5$ is $—(CH_2)_m—N(H)R^{56}$, wherein m is 2 or 3, and $R^{56}$ is a mono or bicyclic heteroaryl, each optionally substituted with 1, 2, 3, or 4 groups which are each independently $R^{50}$.

(zzz) $R^5$ is $—(CH_2)_m—N(H)R^{56}$, wherein m is 2, 3, 4, 5, or 6, and $R^{56}$ is

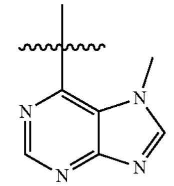 or 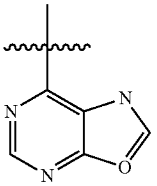

In some embodiments, compounds encompassed within Formula II are provided, wherein A is $—N=$ or $—N^+(R^A)=$, wherein $R^A$ is $C_1$-$C_6$alkyl, wherein when A is $—N^+(R^A)=$, then the compound further comprises a pharmaceutically acceptable anion;

the B ring and the D ring are each independently a fused phenyl ring;

$R^1$, $R^2$, $R^3$ and $R^4$ are each independently hydrogen, $C_1$-$C_6$alkyl, $C_3$-$C_8$cycloalkyl, heterocyclyl, aryl, heteroaryl, or $R^{10}$, wherein the alkyl, cycloalkyl, heterocyclyl, aryl, and heteroaryl groups are each optionally substituted by 1 or 2 $R^{10}$ groups, wherein each $R^{10}$ is independently $R^{15}$, $C_1$-$C_6$alkyl, $—C_1$-$C_6$alkyl-$R^{15}$, wherein each $R^{15}$ is independently halo, nitro, azido, cyano, nitroso, —OR, —SR, $—NR_2$, —C(O)R, —C(O)OR, $—C(O)NR_2$, $—S(O)_2R$, $—S(O)_2NR_2$, —N(R)C(O)R, $—N(R)S(O)_2R$, —OC(O)R, —OC(O)OR, —N(R)C(O)OR, $—N(R)C(O)NR_2$, or $—N(R)C(=NR)NR_2$; and $R^5$ is $C_1$-$C_6$alkyl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkylalkyl, and heterocyclylalkyl groups are optionally substituted with 1 or 2 groups which are each independently oxo or $—R^{50}$; and the arylalkyl and heteroarylalkyl groups are optionally substituted 1, 2, 3, or 4 groups which are each independently $—R^{50}$ or $—C_1$-$C_6$alkyl-$R^{50}$, wherein each $R^{50}$ is independently halogen, cyano, nitro, azido, nitroso, —OR, —SR, $—NR_2$, $—N(R)C(H)(R^{AA})C(O)(R^C)$, $—N(R)NR_2$, —C(O)R, $—C(O)C(H)(R^{AA})N(H)(R^N)$, —C(O)OR, $—C(O)NR_2$, $—C(O)N(R)—C(H)(R^{AA})C(O)R^C$, $—C(=NR)NR_2$, $—S(O)_2R$, $—S(O)_2 NR_2$, —N(R)C(O)R, $—N(R)C(O)C(H)(R^{AA})N(H)(R^N)$, $—N(R)S(O)_2R$, —OC(O)R, —OC(O)OR, —N(R)C(O)OR, $—N(R)C(O)NR_2$, $—N(R)C(=NR)NR_2$, or $C_1$-$C_6$alkyl, wherein each R is independently hydrogen, $C_1$-$C_6$alkyl, $C_2$-$C_6$alkenyl, $C_2$-$C_6$alkynyl, $C_3$-$C_8$cycloalkyl, heterocyclyl, aryl, heteroaryl, $C_3$-$C_8$cycloalkyl($C_1$-$C_6$)alkyl heterocyclyl($C_1$-$C_6$)alkyl, aryl($C_1$-$C_6$)alkyl, or heteroaryl($C_1$-$C_6$)alkyl, wherein the alkyl, alkenyl, alkynyl, cycloalkyl, heterocyclyl, aryl, heteroaryl, cycloalkylalkyl heterocyclylalkyl, arylalkyl, and heteroarylalkyl are each optionally substituted with 1 or 2 $R^{11}$ groups, wherein each $R^{11}$ is independently halo, nitro, azido, cyano, nitroso, $—OR^{12}$, $—SR^{12}$, $—N(R^{12})_2$, $—C(O)R^{12}$, $—C(O)OR^{12}$, $—C(O)N(R^{12})_2$, $—S(O)_2R^{12}$, $—S(O)_2N(R^{12})_2$, $—N(R^{12})C(O)R^{12}$, $—N(R^{12})S(O)_2R^{12}$, $—OC(O)R^{12}$, $—OC(O)OR^{12}$, $—N(R^{12})C(O)OR^{12}$, $—N(R^{12})C(O)N(R^{12})_2$, $—N(R^{12})C(=NR^{12})N(R^{12})_2$, $—N(R^{12})_2$, or $C_1$-$C_6$alkyl, wherein each $R^{12}$ is hydrogen or $C_1$-$C_6$alkyl.

The invention further comprises subgenera of embodiment (2) in which the substituents are selected as any and all combinations of structural formula (II), A, $R^1$-$R^4$, and $R^5$ as defined herein, including without limitation, the following:

Structural Formula II is one of formulae (Ia)-(Ih), and preferably is one of formulae (Id)-(Ih);

wherein A is selected from one of the following groups (aaaa)-(cccc):

(aaaa) A is —N═.

(bbbb) A is —$N^+(R^4)$═, wherein $R^4$ is $C_1$-$C_6$alkyl, and wherein the compound further comprises a pharmaceutically acceptable anion.

(cccc) A is —$N^+(R^4)$═, and the pharmaceutically acceptable anion is a halide.

wherein $R^1$-$R^4$ are selected from one of the following groups (d)-(ss), as defined above;

wherein $R^5$ is selected from one of the following groups (tt)-(zzz), as defined above.

In some embodiments, compounds shown in Table I are contemplated for Formulas I and II.

In certain embodiments, the present invention provides compounds shown in Table I.

An important aspect of the present invention is that compounds of the invention induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. Indeed, the compounds of the present invention (e.g., quindoline (or similar) compounds) can be used to induce apoptosis in any disorder that can be treated, ameliorated, or prevented by the induction of apoptosis (e.g., cancers characterized with unstable G-quadruplex activity).

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, any type of cancer characterized with AR activity and/or AR expression (e.g., cancer (e.g., CRPC), and any type of cancer characterized with c-Myc activity and/or expression. In some embodiments, the condition is characterized with unstable G-quadruplex activity including but not limited to pancreatic cancer, breast cancer, prostate cancer, lymphoma, skin cancer, colon cancer, melanoma, malignant melanoma, ovarian cancer, brain cancer, primary brain carcinoma, head and neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antifungals, and anti-inflammatory agents) and/or therapeutic technique (e.g., surgical intervention, and/or radiotherapies).

In a particular embodiment, the additional therapeutic agent(s) is an anticancer agent. A number of suitable anticancer agents are contemplated for use in the methods of the present invention. Indeed, the present invention contemplates, but is not limited to, administration of numerous anticancer agents such as: agents that induce apoptosis; polynucleotides (e.g., antisense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-$\alpha$) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table IV provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE IV

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N",N",-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus Calmette-Gukin* [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |

TABLE IV-continued

| | | |
|---|---|---|
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R.W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |

TABLE IV-continued

| | | |
|---|---|---|
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl- | Wellcovorin, Leucovorin | Immunex, Corp., Seattle, WA |

TABLE IV-continued

| | | |
|---|---|---|
| 1,4,5,6,7,8 hexahydro4oxo6-pteridinyl)methyl]amino]benzoyl], calcium salt (1:1)) | | |
| Levamisole HCl ((−)-(S)-2,3,5,6-tetrahydro-6-phenylimidazo [2,1-b] thiazole monohydrochloride $C_{11}H_{12}N_2S$•HCl) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum | Eloxatin | Sanofi Synthelabo, Inc., NY, NY |
| Paclitaxel (5ß,20-Epoxy-1,2a,4,7ß,10ß,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |

TABLE IV-continued

| | | |
|---|---|---|
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N, N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1"-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10}•H_2SO_4$) | Velban | Eli Lilly |
| Vincristine ($C_{46}H_{56}N_4O_{10}•H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB- 2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

Antimicrobial therapeutic agents may also be used as therapeutic agents in the present invention. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antifungal agents, and the like.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

Compounds with varying A, B, $R^1$, $R^2$, $R^3$, $R^4$, $R^5$ and n variables can be prepared using the schemes shown below. Unless otherwise defined, the various variables have the definitions as described above for formula (I).

Substituted or unsubstituted amino quindolines can be synthesized starting from nitro substituted chloroquinoline as shown in Scheme I. These substituted or unsubstituted amino quindolines can be used to derive varying functionalities at $R^1$, $R^2$, $R^3$ and $R^4$ positions on quindoline structure as shown in schemes II and III. Amino group can be converted into amides or sulfonamides by reaction with corresponding carbonyl or sulfonyl chlorides Scheme I

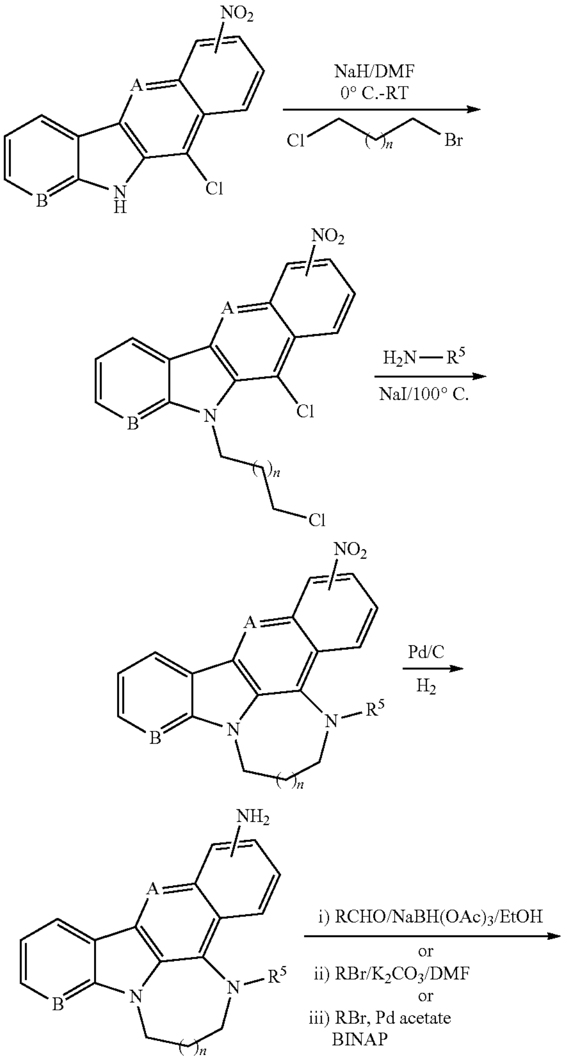

-continued

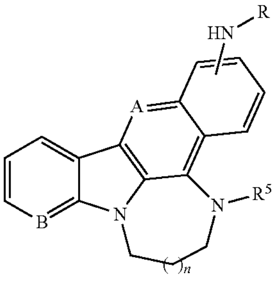

Ref. Van Oeveren et al., *Bioorg. Med. Chem. Lett.* 2007, 17, 1523.

Scheme II

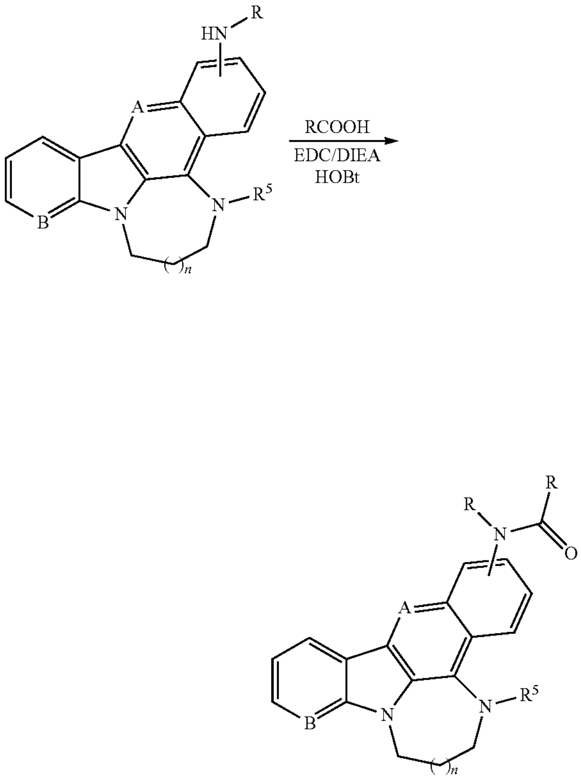

Ref. Johnston, T. et al., *J. Med. Chem.* 1971, 14, 600.

Scheme III

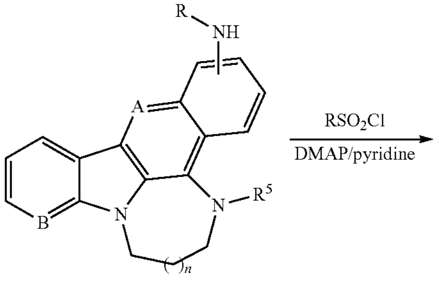

-continued

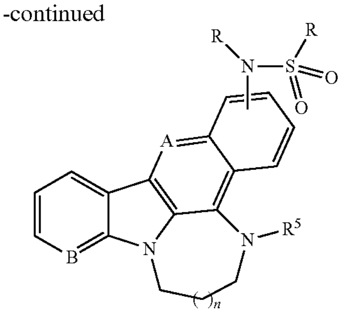

Ref. Miyazaki et al., *Bioorg. Med. Chem. Lett.* 2008, 18, 1967.

Bromo substituted quindolines can be used to synthesize aryl, heteroaryl or heterocyclyl substituted quindolines using Suzuki or Buchwald coupling methods as depicted in schemes IV and V.

Scheme IV

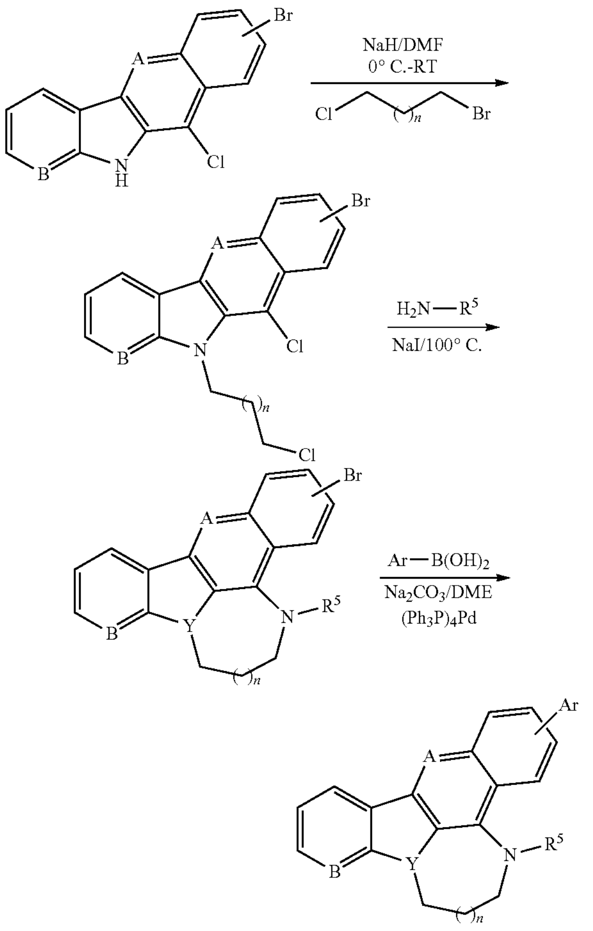

wherein Ar=aryl

Ref. Le Sann et al., *Tetrahedron* 2007, 63, 12903.

As described earlier, the bromoquinoline compound can be subjected to the alkylation and then, the cyclization reaction with various amines to obtain bromo substituted core quindoline scaffold. This bromo substituted scaffold can then be converted into heterocyclyl substituted quindoline compounds through Buchwald reaction.

Scheme V

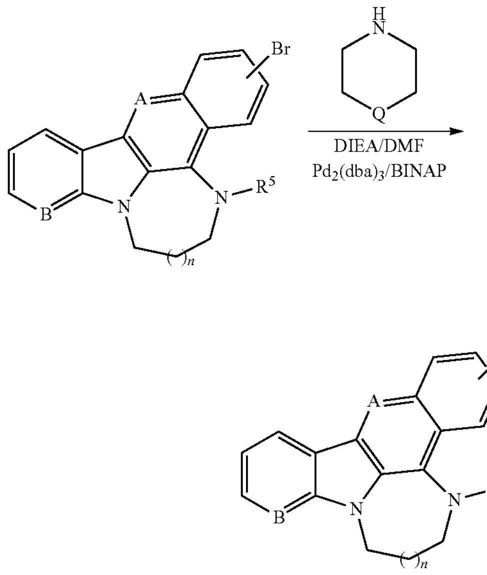

wherein Q=—O—, —$CHR^{10}$, —$NR^{10}$, —S—,

Ref. Xiang et al., *J. Med. Chem.* 2008, 51, 4068.

Compounds with varying $R^5$ substituents can be prepared using the following methods as illustrated in schemes VI and VIII.

The chloroquinoline compound can be alkylated using methods described earlier. These alkylated chloroquinoline can be cyclized using various heterocyclylalkyl amines as depicted in the Scheme VI.

Scheme VI

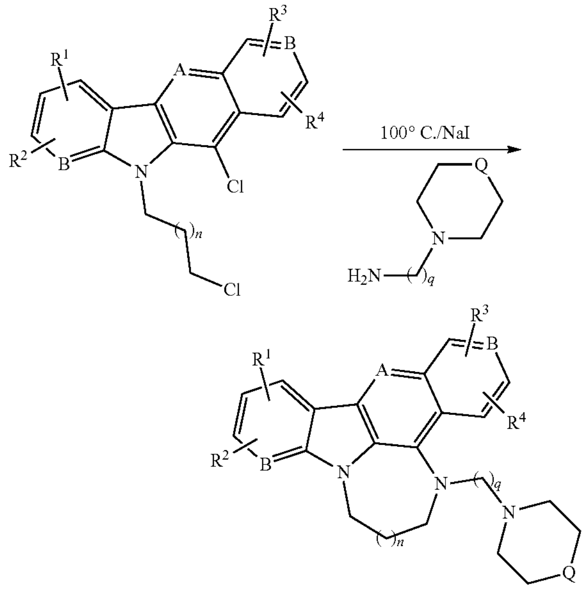

wherein Q=—O—, —$CHR^{10}$, —$NR^{10}$, —S—; and q is 1, 2, 3, 4, 5, or 6.

Substituted or unsubstituted amino group at $R^5$ position can be synthesized using Boc-protected diamines as shown in scheme below.

Scheme VII

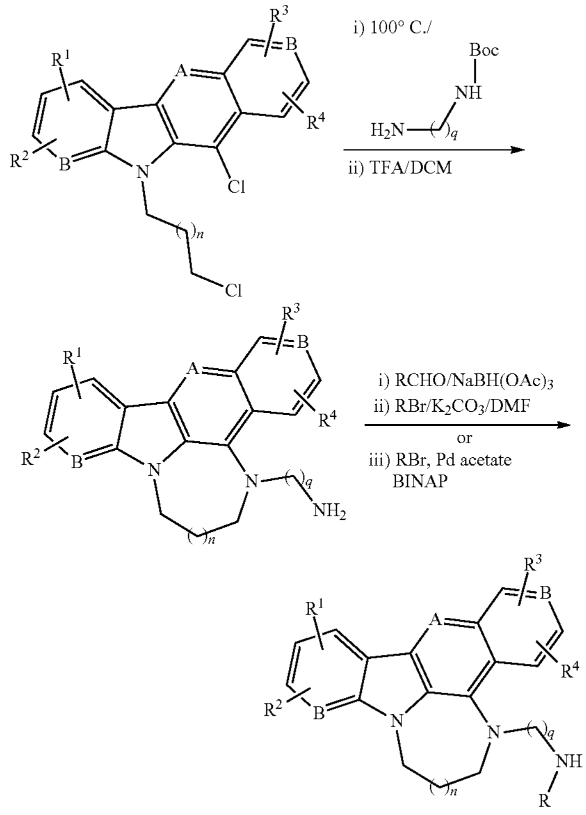

wherein q is 1, 2, 3, 4, 5, or 6.

Aminoalkyl groups at $R^5$ position can be used to obtain different amino acid derivatives, amides, sulfonamides, ureas and carbamates as shown below.

Scheme VIII

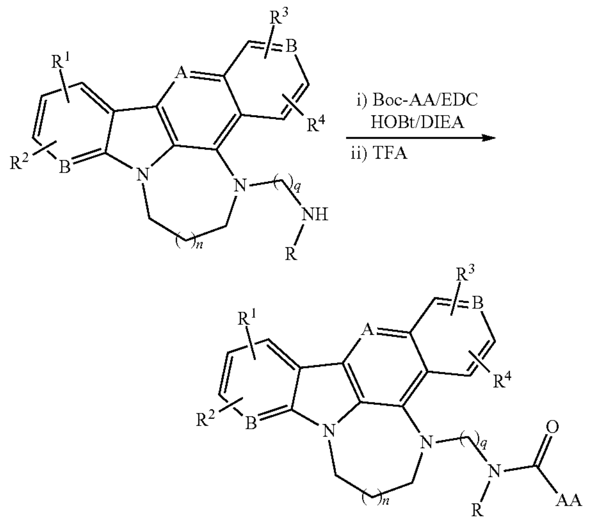

where AA is —C(H)($R^{AA}$)N(H)($R^N$); and q is 1, 2, 3, 4, 5, or 6.

Various carboxy ester containing amines can be used to synthesize carboxyl group substitution at $R^5$ position (scheme IX). These terminal carboxylate groups can be used to synthesize amino acid derivatives and amides as shown in schemes X-XII.

Scheme IX

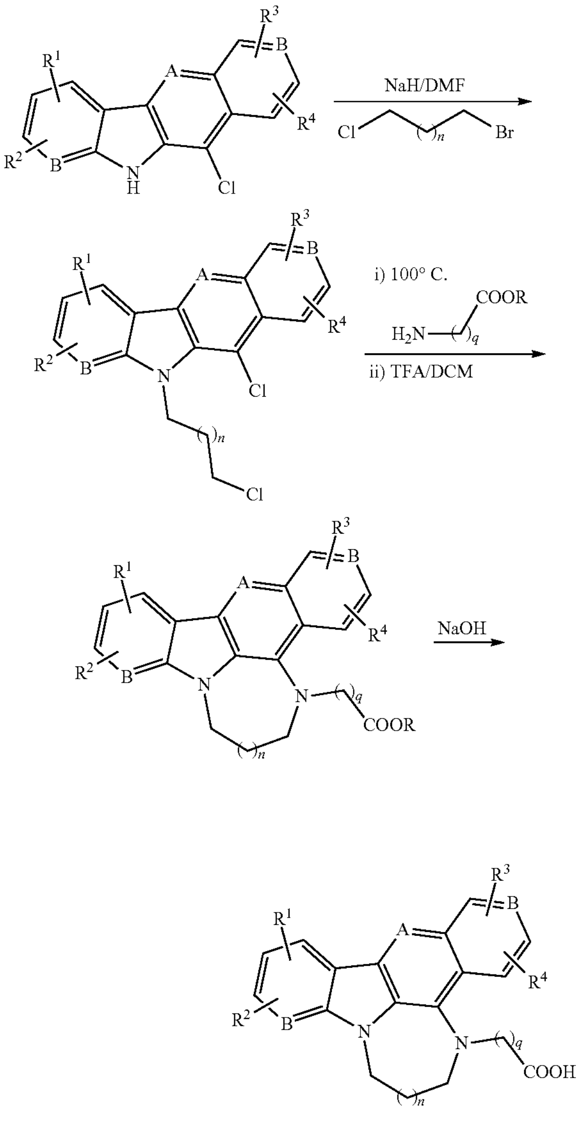

wherein q is 1, 2, 3, 4, 5, or 6.

Scheme X

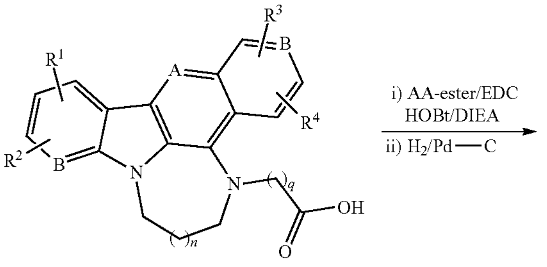

-continued

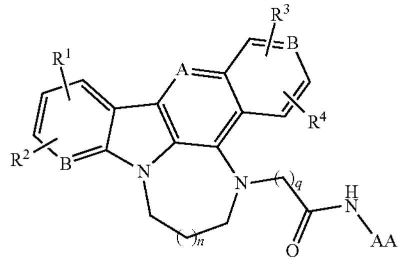

wherein AA is —C(H)($R^{AA}$)C(O)$R^C$; and q is 1, 2, 3, 4, 5, or 6.

Scheme XI

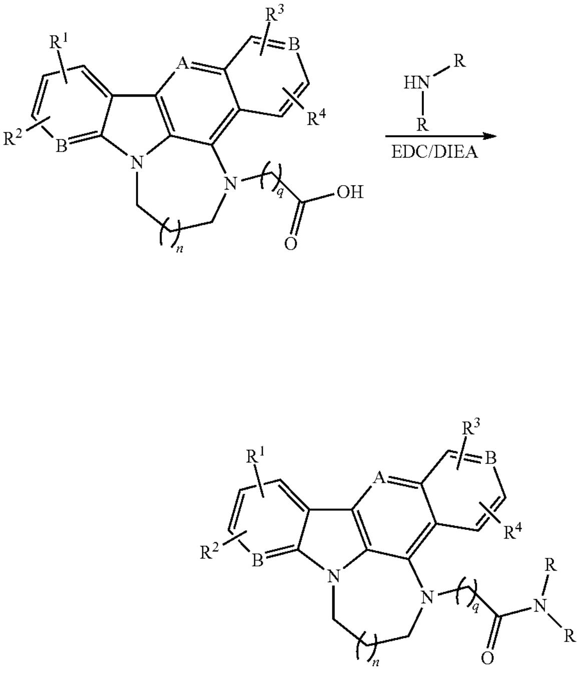

wherein q is 1, 2, 3, 4, 5, or 6.

Compounds with hydroxyl substitution at $R^5$ position can be synthesized using amino alcohols. The hydroxyl group can be converted to bromide or aldehyde group (using mild oxidation). Both bromo and aldehyde groups can be used to synthesize various substituted or unsubstituted heterocyclyl quindoline compounds as shown in schemes XII-XIV.

Scheme XII

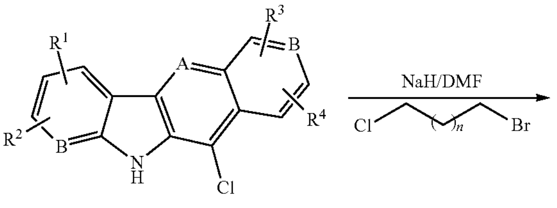

-continued
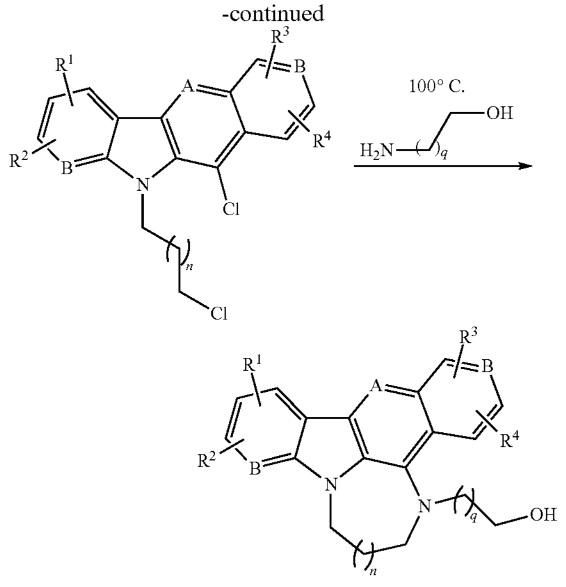
wherein q is 1, 2, 3, 4, 5, or 6.
Scheme XIII
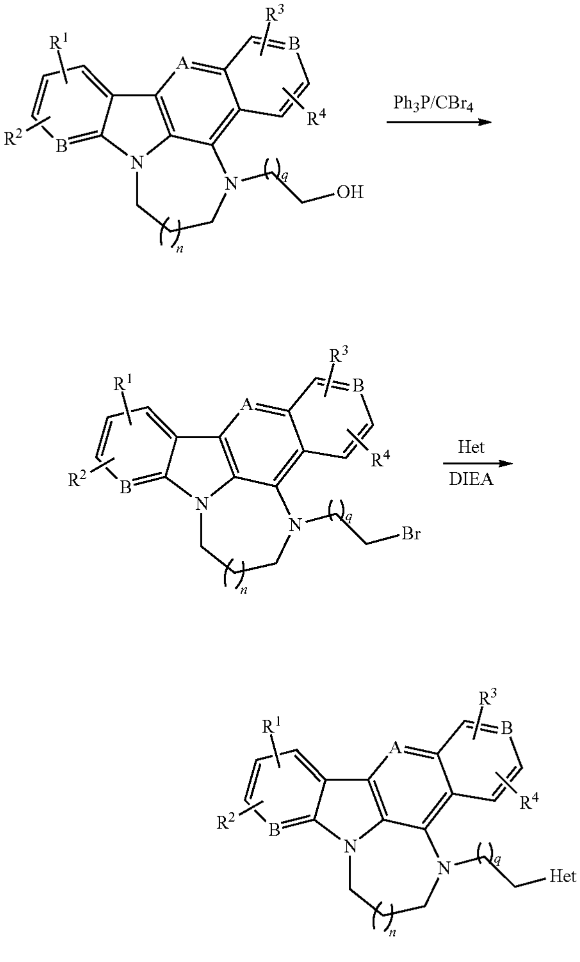
wherein Het is heterocyclyl or heteroaryl; and q is 1, 2, 3, 4, 5, or 6.
Scheme XIV
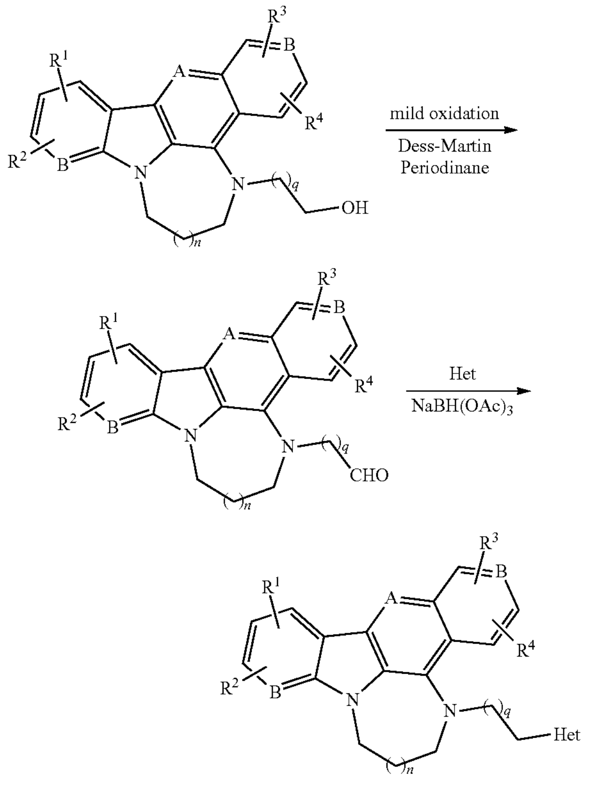
wherein Het is heterocyclyl or heteroaryl; and q is 1, 2, 3, 4, 5, or 6.
Quinoline aromatic nitrogen can be alkylated with various alkyl, arylalkyl bromides or heterocyclylalkyl bromides as shown below.
Scheme XV
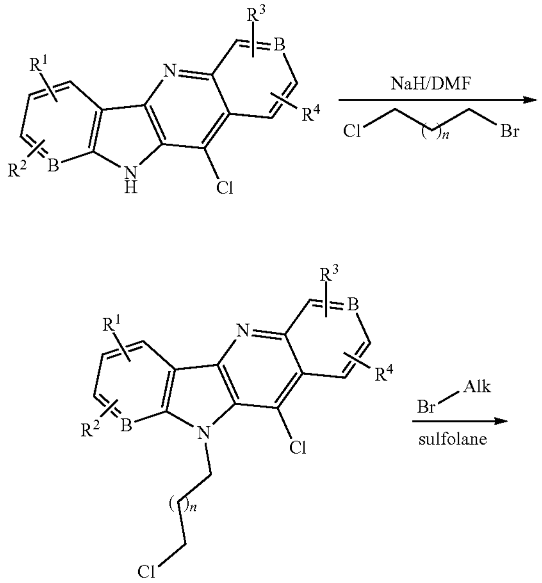

-continued

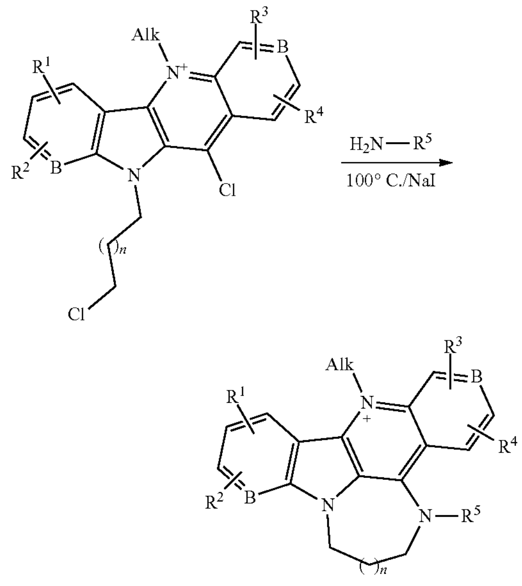

wherein Alk is an alkyl group.

Example II

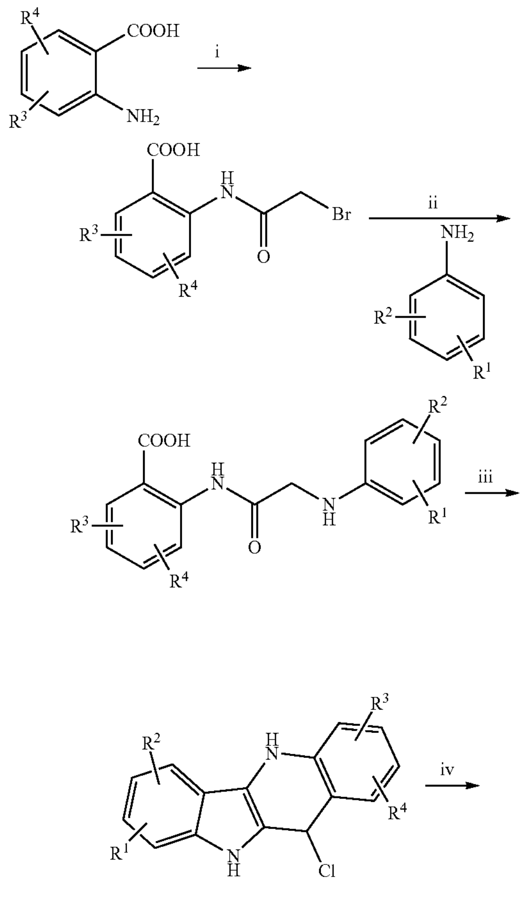

-continued

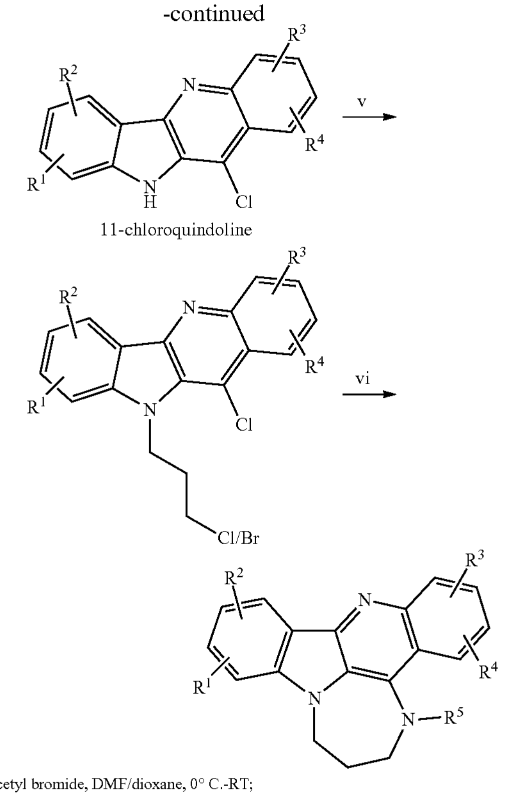

11-chloroquindoline (i) Bromoacetyl bromide, DMF/dioxane, 0° C.-RT;
(ii) DMF, 130° C.;
(iii) PPA, 120° C.;
(iv) $POCl_3$, Reflux
(v) NaH, DMF, 1,3-Dibromopropane or 1-bromo-3-chloropropane, 0° C.-RT;
(vi) Appropriate amines, NaI (Table 1), neat condition, 100° C.;

For the following examples, 11-Chloroquindoline can synthesized by previously reported procedures. See, Takeuchi, et al. *Chem. Pharm. Bull.* 1997, 45(12), 2096-2099; and Bierer, et al. *J. Med. Chem.* 1998, 41, 2754-2764.

Abbreviations Used in the Present Invention

HOBt 1-Hydroxybenzotriazole
DCM Dichloromethane
EtOAc Ethyl acetate
MeOH Methanol
$CHCl_3$ Chloroform
DME 1,2-dimethoxyethane
EDC.HCl N-Ethyl-N'-(3-dimethylaminopropyl)carbodiimide hydrochloride
DIEA N,N-diisopropylethylamine
DMF N,N-dimethylformamide
PPA Polyphosphoric acid
$POCl_3$ Phosphorus oxychloride
NaI Sodium iodide
$Pd(ddpf)_2Cl_2$ [1,1'-bis(diphenylphosphino)ferrocene]dichloropalladium (II)
Liq. $NH_3$ Liquor ammonia
$NaO^tBu$ Sodium tert-butoxide
$MgSO_4$ Magnesium sulfate
NaH Sodium hydride TLC Thin layer chromatography NMR Nuclear magnetic resonance Boc t-Butyloxycarbonyl Preparation of 10-(3-bromopropyl)-11-chloro-10H-indolo[3,2-b]quinoline

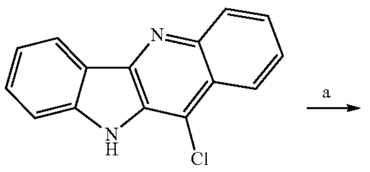

11-chloro-10H-indolo[3,2-b]quinoline

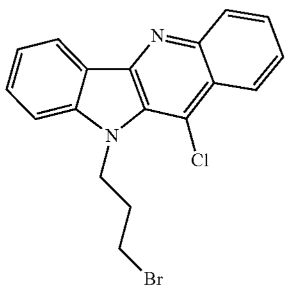

10-(3-bromopropyl)-11-chloro-10H-indolo[3,2-b]quinoline (a) NaH, 1,3-dibromopropane, DMF, 0° C.-RT To a solution of 11-chloro-10H-indolo[3,2-b]quinoline (2.5 g, 9.92 mmol) in dry DMF (20 mL) was added 60% sodium hydride in mineral oil (750 mg, 39.6 mmol) at 0° C. The reaction mixture was stirred at the same temperature for 1 hour and 1,3-dibromopropane (2.97 g, 14.88 mmol) was added drop wise to the reaction mixture at 0° C. After completion of the addition, the reaction mixture was stirred at room temperature for 2 h. Then the reaction mixture was poured in to ice cold water and extracted with EtOAc (3×100 mL). The combined EtOAc layers were washed with water, dried over anhydrous $MgSO_4$ and concentrated under vacuum to give the crude product. The crude product was purified by silica gel column chromatography using 2-4% EtOAc in hexane as an eluent to afford 1.0 g (27%) of 10-(3-bromopropyl)-11-chloro-10H-indolo[3,2-b]quinoline as yellow solid. $^1H$ NMR (300 MHz, $CDCl_3$): δ 8.54 (d, J=7.5 Hz, 1H, ArH), 8.43 (d, J=8.1 Hz, 1H, ArH), 8.33 (d, J=8.4 Hz, 1H, ArH), 7.77-7.66 (m, 3H, ArH), 7.61 (d, J=8.4 Hz, 1H, ArH), 7.40 (t, J=7.3 Hz, 1H, ArH), 4.95 (t, J=7.2 Hz, 2H), 3.53 (t, J=6.1 Hz, 2H), 2.58-2.49 (m, 2H). MS (ESI): m/z 373.2 (80%), 375.2 [100%, $(M+H)^+$].

Preparation of Compound 1

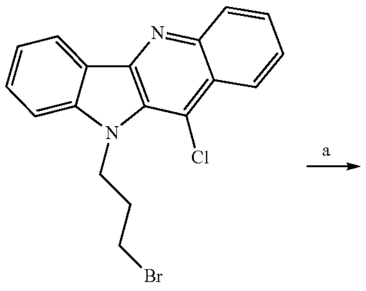

10-(3-bromopropyl)-11-chloro-10H-indolo[3,2-b]quinoline

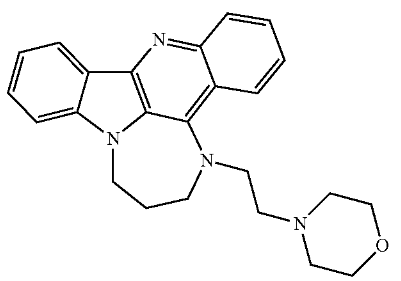

1

(a) N-(2-aminoethyl) morpholine, Neat, 100° C.

A stirred mixture of 10-(3-bromopropyl)-11-chloro-10H-indolo[3,2-b]quinoline (900 mg, 2.4 mmol) in 4-(2-aminoethyl)morpholine (5 mL, excess) was heated at 100° C. for overnight. After completion of the reaction, as indicated by TLC (8% MeOH in $CHCl_3$), the reaction mixture was cooled to room temperature and poured into ice cold water and extracted with EtOAc (3×100 mL). The combined EtOAc layers were washed with water (3×200 mL), separated and dried over anhydrous $MgSO_4$, and finally concentrated under reduced pressure to give the crude product. The crude product was then purified by silica gel column chromatography using 2-3% MeOH in EtOAc as an eluent to afford 300 mg (36%) of pure product (1) as yellow color solid. $^1H$ NMR (300 MHz, $CDCl_3$): δ 8.53 (d, J=7.6 Hz, 1H, ArH), 8.34 (d, J=7.9 Hz, 1H, ArH), 8.27 (d, J=8.2 Hz, 1H, ArH), 7.71-7.55 (m, 2H, ArH), 7.50 (t, J=7.2 Hz, 1H, ArH), 7.43 (d, J=8.2 Hz, 1H, ArH), 7.32 (t, J=7.4 Hz, 1H, ArH), 4.21 (t, J=5.8 Hz, 2H), 3.78-3.66 (m, 2H), 3.65-3.57 (m, 4H), 3.50 (t, J=6.8 Hz, 2H), 2.76 (t, J=6.8 Hz, 2H), 2.51-2.35 (m, 6H). $^{13}C$ NMR (75 MHz, $CDCl_3$): δ 147.95, 146.32, 145.80, 139.44, 129.83, 129.73, 129.66, 127.03, 124.37, 124.30, 123.32, 123.21, 122.44, 120.45, 110.07, 67.29, 57.91, 54.52, 52.00, 51.10, 47.05, and 26.55. MS (ESI): m/z 387.2 [100%, $(M+H)^+$].

Preparation of Compound 3

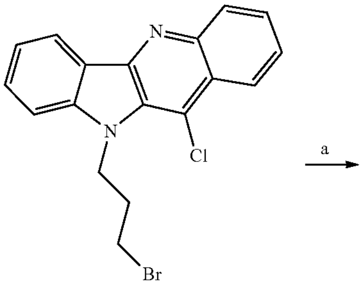

10-(3-bromopropyl)-11-chloro-10H-indolo[3,2-b]quinoline

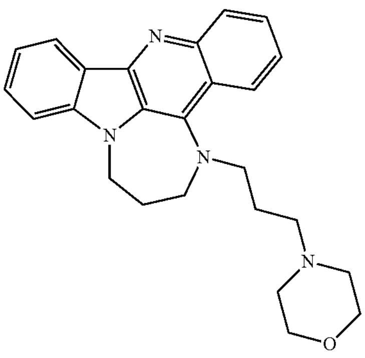

3

(a) N-(3-aminopropyl) morpholine, Neat, 100° C.

This compound was synthesized using the procedure similar to compound 1. N-(3-aminopropyl)morpholine (4.0 mL, excess) was used for the coupling reaction to yield compound 3 in 41% yield as yellow color solid. $^1$H NMR (300 MHz, $CDCl_3$): δ 8.53 (d, J=7.5 Hz, 1H, ArH), 8.32-8.23 (m, 2H, ArH), 7.70-7.58 (m, 2H, ArH), 7.54-7.40 (m, 2H, ArH), 7.33 (t, J=7.35 Hz, 1H, ArH), 4.23 (t, J=5.7 Hz, 2H), 3.78-3.60 (m, 6H), 3.43 (t, J=7.65 Hz, 2H), 2.51-2.32 (m, 8H), 2.10-1.94 (m, 2H). $^{13}$C NMR (75 MHz, $CDCl_3$): δ 147.89, 146.28, 145.88, 139.72, 129.84, 129.74, 129.66, 127.06, 124.37, 124.31, 123.33, 122.48, 120.49, 110.12, 67.34, 56.38, 54.13, 52.76, 50.45 47.14, 26.19, 26.12. MS (ESI): m/z 401.3 [100%, $(M+H)^+$].

Preparation of Compound 2

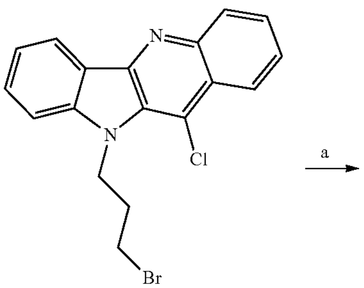

10-(3-bromopropyl)-11-chloro-10H-indolo[3,2-b]quinoline

-continued

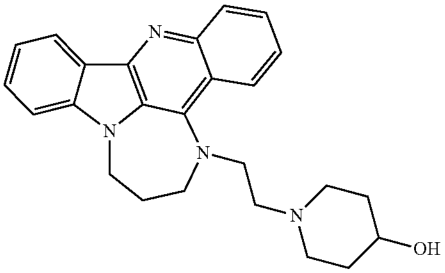

2

(a) N-(2-aminoethyl)-4-piperidinol, Neat, 100° C.

This compound was synthesized using the procedure similar to compound 1. N-(2-aminoethyl)-4-piperidinol (1.0 mL, 6.9 mmol) was used for the coupling reaction to yield compound 2 in 30% yield as yellow color solid. $^1$H NMR (300 MHz, $CDCl_3$): δ 8.54 (d, J=7.8 Hz, 1H, ArH), 8.40-8.22 (m, 2H, ArH), 7.70-7.58 (m, 2H, ArH), 7.56-7.40 (m, 2H, ArH), 7.33 (t, J=7.35 Hz, 1H, ArH), 4.24 (t, J=5.8 Hz, 2H), 3.81-3.63 (m, 3H), 3.54 (t, J=6.9 Hz, 2H), 2.91-2.65 (m, 4H), 2.55-2.38 (m, 2H), 2.31-2.15 (m, 3H, —OH is merged), 1.91-1.76 (m, 2H), 1.62-1.42 (m, 2H). $^{13}$C NMR (75 MHz, $CDCl_3$): δ 147.81, 146.22, 145.84, 139.61, 129.85, 129.68, 129.59, 127.07, 124.34, 124.31, 123.21, 122.54, 120.48, 110.07, 67.81, 57.25, 52.47, 51.86, 51.16, 47.07, 34.64, 26.53. MS (ESI): m/z 401.2 [100%, $(M+H)^+$].

Preparation of Compound 8

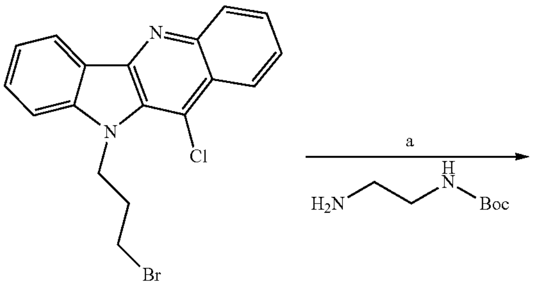

10-(3-bromopropyl)-11-chloro-10H-indolo[3,2-b]quinoline

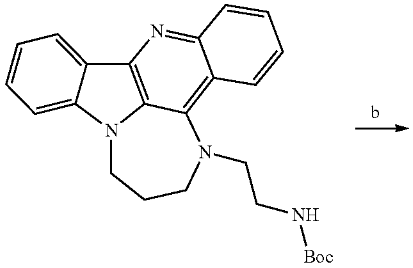

i

-continued

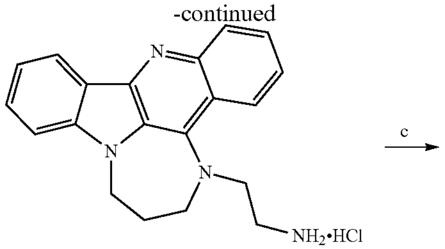

ii

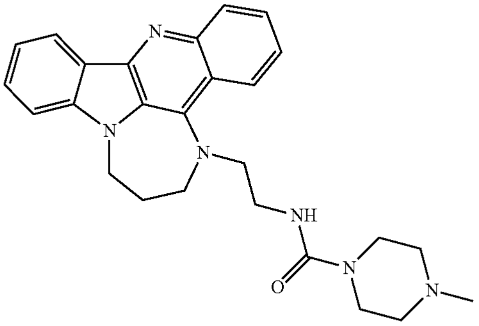

8

(a) Neat, 100° C.; b) DCM, MeOH•HCl, 0° C.-RT; c) 4-Methyl-1-piperazinecarbonylchloride•HCl, DIEA, DCM, 0° C.-RT.

Preparation of Compound (i)

A mixture of 10-(3-bromopropyl)-2,11-dichloro-10H-indolo[3,2-b]quinoline (500 mg, 1.34 mmol) in of N-Bocethylenediamine (1.0 g, 6.7 mmol) was stirred at 100° C. for 16 h. The progress of the reaction was monitored by TLC (40% EtOAc in hexane). After completion of the reaction, the reaction mixture was cooled to room temperature and poured into ice cold water and extracted with $CHCl_3$ (3×100 mL). The combined $CHCl_3$ layers were washed with water (4×200 mL), separated and dried over anhydrous $MgSO_4$, and finally concentrated under reduced pressure to give the crude product. The crude product was then purified by silica gel column chromatography using 20-25% EtOAc in hexane as an eluent to afford 250 mg (44%) of pure compound (i) as yellow color solid. $^1$H NMR (300 MHz, $CDCl_3$): δ 8.52 (d, J=7.8 Hz, 1H, ArH), 8.32-8.23 (m, 2H, ArH), 7.71-7.60 (m, 2H, ArH), 7.58-7.43 (m, 2H, ArH), 7.34 (t, J=7.3 Hz, 1H, ArH), 4.72 (br s, 1H, NH), 4.24 (t, J=6.0 Hz, 2H), 3.80-3.68 (m, 2H), 3.60-3.45 (m, 4H), 2.51-2.39 (m, 2H), 1.42 (s, 9H). MS (ESI): m/z 417.2 [100%, $(M+H)^+$].

Preparation of Compound (ii)

To a stirred solution of compound (i) (100 mg, 0.23 mmol) in DCM (8 mL) was added methanolic HCl (3 mL) slowly at 0° C. After completion of the addition, the reaction mixture was stirred at room temperature for overnight. The solvent was removed under vacuum and the crude product was triturated with DCM (3×10 mL) to get the product as yellow solid. The product was collected by filtration and washed with DCM (2×10 mL) and dried under vacuum to yield 70 mg of pure compound (ii) as yellow color solid. $^1$H NMR (300 MHz, $CD_3OD$): δ 8.50 (d, J=8.1 Hz, 1H, ArH), 8.36 (d, J=8.4 Hz, 1H, ArH), 8.20 (d, J=8.4 Hz, 1H, ArH), 7.99 (td, J=0.9 &7.2 Hz, 1H, ArH), 7.93-7.71 (m, 3H, ArH), 7.50 (td, J=0.9 &7.8 Hz, 1H, ArH), 4.53 (t, J=5.7 Hz, 2H), 4.20 (t, J=7.6 Hz, 2H), 4.15-4.05 (m, 2H), 3.45 (t, J=7.5 Hz, 2H), 2.71-2.56 (m, 2H). MS (ESI): m/z 317.2 [100%, $(M+H)^+$].

Preparation of Compound (8)

To a stirred mixture of compound (ii) (70 mg, 0.22 mmol) in DCM was added DIEA (0.1 mL, 0.33 mmol) at 0° C. Then the 4-methyl-1-piperazine carbonyl chloride hydrochloride (65 mg, 0.33 mmol) was added to the reaction mixture and the stirring was continued for overnight at room temperature. After completion of the reaction as indicated by TLC (10% MeOH in DCM), the solvent was removed under vacuum. The residue was washed with water (50 mL) and then extracted with DCM (3×50 mL). The combined organic layers was dried over anhydrous $MgSO_4$ and finally concentrated under vacuum to give crude the product. The crude product was then purified by silica gel column chromatography using 4-5% MeOH in DCM as an eluent to yield compound (8) as oil. This oil was solidified by treating with DCM/hexane and the solids were collected by filtration and washed with n-pentane (2×3 mL) to get 45 mg (46%) of the pure compound (8) as yellow solid. $^1$H NMR (300 MHz, $CDCl_3$): δ 8.54 (d, J=7.5 Hz, 1H, ArH), 8.28 (d, J=8.4 Hz, 1H, ArH), 8.22 (d, J=8.7 Hz, 1H, ArH), 7.70-7.58 (m, 2H, ArH), 7.56-7.43 (m, 2H, ArH), 7.35 (t, J=7.5 Hz, 1H, ArH), 4.43 (br s, 1H, NH), 4.21 (t, J=5.5 Hz, 2H), 3.82-3.74 (m, 2H), 3.73-3.62 (m, 2H), 3.60-3.48 (m, 2H), 3.09-2.95 (m, 4H), 2.53-2.39 (m, 2H), 2.20 (s, 3H), 2.16-2.02 (m, 4H). $^{13}$C NMR (75 MHz, $CDCl_3$): 157.61, 146.41, 146.16, 139.17, 130.08, 129.69, 127.34, 124.48, 124.32, 123.43, 122.69, 122.55, 120.86, 110.49, 55.39, 54.68, 51.96, 47.19, 46.31, 43.69, 39.89, 28.25. MS (ESI): m/z 443.2 [100% $(M+H)^+$].

Preparation of Compound 4

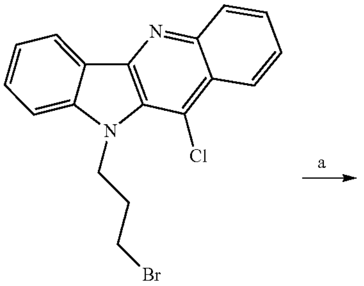

10-(3-bromopropyl)-11-chloro-10H-indolo[3,2-b]quinoline

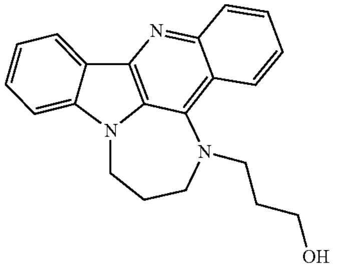

4

(a) 3-amino-1-propanol, Neat, 100° C.

This compound was synthesized using the procedure similar to compound 1. 3-Amino-1-propanol (3.0 mL, excess) was used for the coupling reaction to yield compound 4 in 54% yield as yellow color solid. $^1$H NMR (300 MHz, $CDCl_3$): δ 8.53 (d, J=7.8 Hz, 1H, ArH), 8.30-8.21 (m, 2H, ArH), 7.68-7.58 (m, 2H, ArH), 7.54-7.40 (m, 2H, ArH), 7.33 (t, J=7.5 Hz, 1H, ArH), 4.20 (t, J=6.0 Hz, 2H), 3.79 (t, J=6.0 Hz, 2H), 3.73-3.67 (m, 2H), 3.44 (t, J=7.6 Hz, 2H), 2.45-2.34 (m, 2H), 2.16-2.03 (m, 2H), 2.00 (br.s, 1H, —OH). $^{13}$C NMR (75 MHz, $CDCl_3$): δ 145.78, 140.11, 129.92, 129.489, 129.05, 127.23, 124.42, 124.28, 123.08, 122.88, 122.63, 120.54, 110.12, 60.97, 52.13, 50.33, 47.02, 31.86 25.92. MS (ESI): m/z 332.4 [100%, $(M+H)^+$].

Preparation of Compound 17

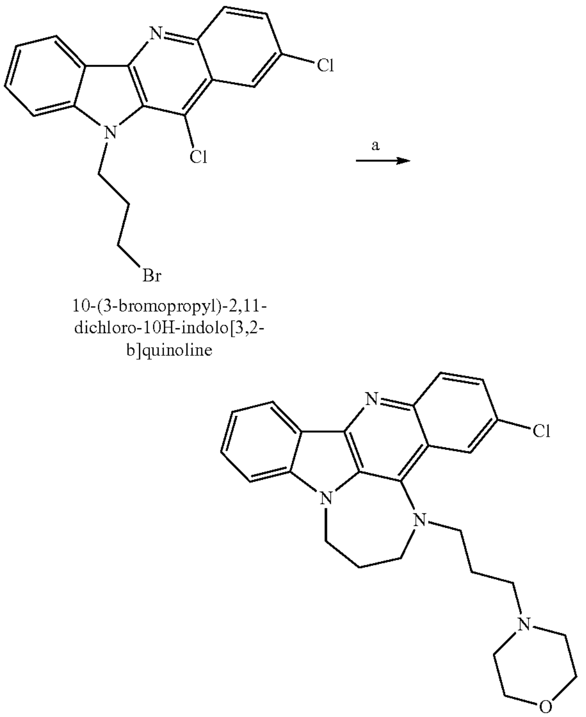

10-(3-bromopropyl)-2,11-dichloro-10H-indolo[3,2-b]quinoline

17

(a) N-(3-aminopropyl) morpholine, Neat, 100° C.

This compound was synthesized using the procedure similar to compound 1. N-(3-aminopropyl)morpholine (4.0 mL, excess) was used for the coupling reaction to yield compound 17 in 41% yield as yellow color solid. $^1$H NMR (300 MHz, $CDCl_3$): δ 8.48 (d, J=7.5 Hz, 1H, ArH), 8.21-8.15 (m, 2H, ArH), 7.61 (t, 1H, J=7.8 Hz ArH), 7.55 (dd, 1H, J=2.4 & 9.0 Hz, ArH), 7.41 (d, J=8.1 Hz, 1H, ArH), 7.33 (t, J=7.5 Hz, 1H, ArH), 4.19 (t, J=5.8 Hz, 2H), 3.75-3.58 (m, 6H), 3.36 (t, J=7.8 Hz, 2H), 2.48-2.32 (m, 8H), 2.08-1.92 (m, 2H). $^{13}$C NMR (75 MHz, $CDCl_3$): δ 148.34, 145.87, 144.676, 138.61, 131.36, 130.08, 130.03, 129.96, 127.72, 124.16, 123.28, 123.25, 122.37, 120.69, 110.17, 67.34, 56.49, 54.13, 52.76, 50.44, 47.12, 26.08, 26.05. MS (ESI): m/z 435.2 [100%, $(M+H)^+$].

Preparation of Compound 10

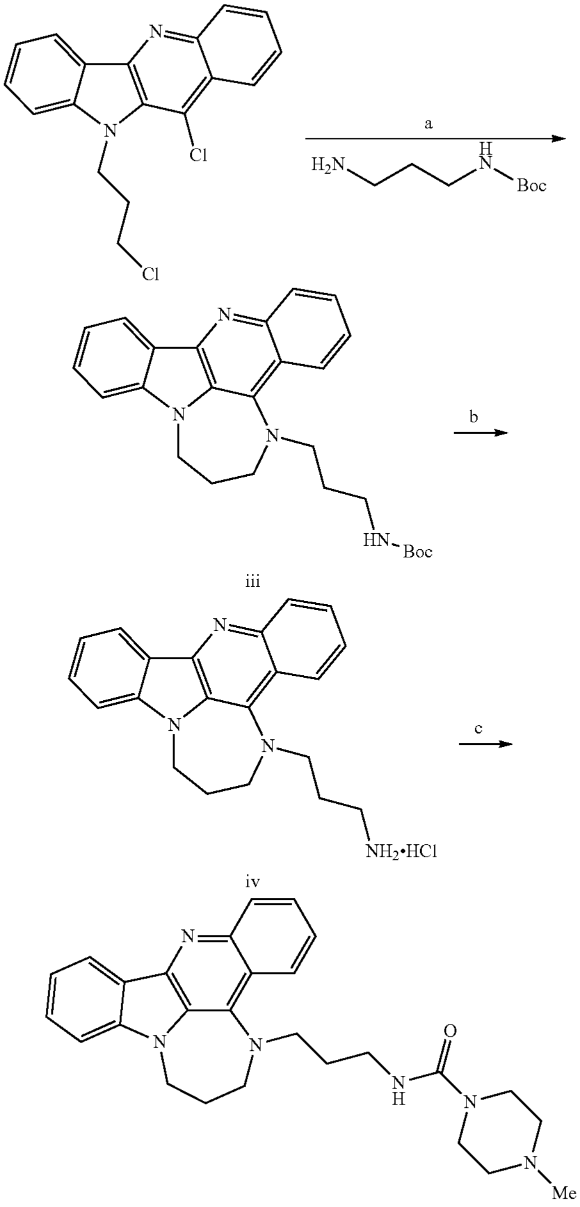

iii iv

10

(a) Neat, 100° C.; b) DCM, MeOH•HCl, 0° C.-RT; c) 4-Methyl-1-piperazinecarbonylchloride•HCl, DIEA, DCM, RT.

Preparation of Compound (iii)

A mixture of 11-chloro-10-(3-chloropropyl)-6,8-dimethyl-10H-indolo[3,2-b]quinoline (1.0 g, 3.04 mmol) and sodium iodide (452 mg, 3.04 mmol) in N-Bocpropylenediamine (3.6 g, 20.68 mmol) was stirred at 100° C. for 16 h. The progress of the reaction was monitored by TLC (40% EtOAc in hexane). After completion of the reaction, the reaction mixture was cooled to room temperature and poured in to ice cold water and extracted with $CHCl_3$ (3×100 mL). The combined $CHCl_3$ layers were washed with water (4×200 mL), separated and dried over anhydrous $MgSO_4$, and finally concentrated under reduced pressure to give the crude product. The crude product was then purified by silica gel column chromatography using 20-25% EtOAc in hexane as an eluent to afford 700 mg (53%) of pure compound (iii) as yellow color solid. $^1$H NMR (300 MHz, $CDCl_3$): δ 8.53 (d, J=7.5 Hz, 1H, ArH), 8.28 (d, J=8.4 Hz, 1H, ArH), 8.19 (d, J=8.4 Hz, 1H, ArH), 7.70-7.58 (m, 2H, ArH), 7.55-7.40 (m, 2H, ArH), 7.33 (t, J=7.3 Hz, 1H, ArH), 4.70-4.60 (br.s, 1H, NH), 4.22 (t, J=5.8 Hz, 2H), 3.75-3.63 (m, 2H), 3.36 (t, J=7.6 Hz, 2H), 3.30-3.13 (m, 2H), 2.49-2.35 (m, 2H), 2.10-1.93 (m, 2H), 1.43 (s, 9H). MS (ESI): m/z 431 [100%, $(M+H)^+$];

Preparation of Compound (iv)

To a stirred solution of compound (iii) (200 mg, 0.46 mmol) in DCM (20 mL) was added methanolic. HCl (3 mL) slowly at 0° C. After completion of the addition the reaction mixture was stirred at room temperature for overnight. The solvent was removed under vacuum and the crude product was triturated with DCM (3×10 mL) to get the product as yellow color solid. The product was collected by filtration, washed with DCM (2×20 mL) and dried under vacuum to yield 170 mg of pure compound (iv) as yellow solid. $^1$H NMR (300 MHz, $CD_3OD$): δ 8.47 (d, J=8.1 Hz, 1H, ArH), 8.34 (d, J=8.4 Hz, 1H, ArH), 8.15 (d, J=8.4 Hz, 1H, ArH), 8.03-7.93 (m, 1H, ArH), 7.91-7.77 (m, 2H, ArH), 7.76-7.67 (m, 1H, ArH), 7.56-7.45 (m, 1H, ArH), 4.52 (t, J=5.8 Hz, 2H), 4.15-4.05 (m, 2H), 4.02 (t, J=7.6 Hz, 2H), 2.87 (t, J=7.6 Hz, 2H), 2.70-2.58 (m, 2H), 2.31-2.15 (m, 2H). MS (ESI): m/z 331 [100%, $(M+H)^+$].

Preparation of Compound (10)

To a stirred mixture of the compound (iv) (500 mg, 1.35 mmol) in DCM was added DIEA (0.6 mL, 3.28 mmol) at 0° C. Then 4-methyl-1-piperazine carbonyl chloride hydrochloride (403 mg, 2.03 mmol) was added to the reaction mixture and the stirring was continued for overnight at room temperature. After completion of the reaction as indicated by TLC (15% MeOH in $CHCl_3$), the solvent was removed under vacuum. The residue was washed with water (100 mL) and then extracted with DCM (3×50 mL). The combined organic layers were washed with water (3×100 mL), separated and dried over anhydrous $MgSO_4$ and finally concentrated under vacuum to give crude product. The crude product was purified by silica gel column chromatography using 8-10% MeOH in DCM as an eluent to yield 250 mg (40%) of compound (10) as yellow color solid. $^1$H NMR (300 MHz, $CDCl_3$): δ 8.50 (d, J=7.8 Hz, 1H, ArH), 8.24 (d, J=8.7 Hz, 1H, ArH), 8.16 (d, J=8.7 Hz, 1H, ArH), 7.67-7.57 (m, 2H, ArH), 7.50-7.38 (m, 2H, ArH), 7.31 (t, J=7.3 Hz, 1H, ArH), 4.63 (t, 1H, NH), 4.15 (t, J=5.8 Hz, 2H), 3.72-3.61 (m, 2H), 3.38 (t, J=7.3 Hz, 2H), 3.32-3.18 (m, 6H), 2.45-2.28 (m, 6H), 2.27 (s, 3H), 2.08-1.92 (m, 2H). $^{13}$C NMR (75 MHz, $CDCl_3$): 157.99, 147.88, 146.23, 145.85, 139.49, 129.90, 129.58, 129.47, 127.07, 124.37, 124.31, 123.24, 123.00, 122.41, 120.54, 110.22, 55.01, 52.68, 50.85, 47.16, 46.52, 43.96, 38.91, 29.73, 26.66. MS (ESI): m/z 457.2 [100%, $(M+H)^+$].

Preparation of Compound 9

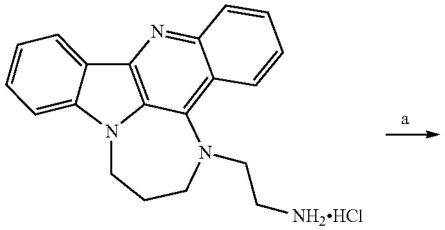

ii

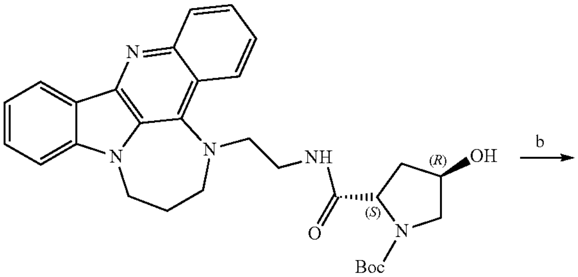

v

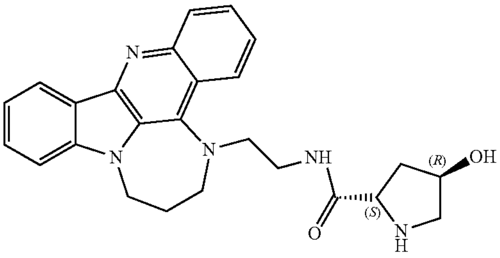

9

(a) DIEA, Boc-trans-4-hydroxyl-L-proline, EDC•HCl, HOBt, DCM, MeOH•HCl, 0° C.-RT Preparation of Compound (v)

To a stirred mixture of compound (ii) (200 mg, 0.56 mmol) in DCM was added DIEA (0.15 mL, 1.4 mmol) at 0° C. Then the Boc-trans-4-hydroxy-L-proline (196 mg, 0.85 mmol) was added to the reaction mixture then stirred for 10 min at the same temperature and HOBt (115 mg, 0.85 mmol) was added and stirred for 10 min at 0° C. After this EDC·HCl (162 mg, 0.85 mmol) was added and stirring was continued for overnight at room temperature. After completion of the reaction as indicated by TLC (10% MeOH in DCM), the solvent was removed under vacuum. The residue was washed with water (50 mL) and then extracted with DCM (3×50 mL). The combined organic layers were washed with water (3×100 mL), separated and dried over anhydrous $MgSO_4$ and finally concentrated under vacuum to give crude product. The crude product was then purified by silica gel column chromatography using 4-5% MeOH in DCM as an eluent to yield 185 mg (61%) of compound (v) as yellow color solid. $^1$H NMR (300 MHz, $CDCl_3$): δ 8.90-8.70 (m, 1H, ArH), 8.60-8.30 (m, 1H, ArH), 8.09 (d, J=8.7 Hz, 1H, ArH), 7.80-7.55 (m, 2H, ArH), 7.54-7.35 (m, 2H, ArH), 7.34-7.25 (m, 1H, ArH), 7.0 (br.s, 1H, NH), 4.5-4.2 (m, 2H), 4.15-3.70 (6H), 3.69-3.45 (m, 2H), 3.40-3.05 (m, 2H), 2.70-2.40 (m, 2H), 1.90-1.10 (m, 12H). MS (ESI): m/z 530.5 [100%, $(M+H)^+$].

Preparation of Compound (9)

To a stirred solution of compound (v) (185 mg, 0.348 mmol) in DCM (10 mL) was added methanolic HCl (3 mL) slowly at 0° C. After completion of addition the reaction mixture was stirred at room temperature for overnight. After completion of the reaction as indicated by TLC (10% MeOH in DCM), the solvent was removed under vacuum and the crude product was triturated with DCM (3×10 mL) to obtain the product as yellow color solid. To this solid EtOAc (50 mL) and water (20 mL) were added and made alkaline with liq. $NH_3$ (≈5-6 mL). The product was extracted with EtOAc (2×20 mL), the combined EtOAc layers were dried over anhydrous $MgSO_4$ and finally concentrated under vacuum to give crude product. The crude was then purified by silica gel column chromatography using 8-10% MeOH in DCM as an eluent to yield 70 mg (46%) of compound (9) as yellow color solid. $^1$H NMR (300 MHz, $CDCl_3$): δ 8.50 (d, J=7.8 Hz, 1H, ArH), 8.24 (d, J=8.4 Hz, 1H, ArH), 8.19 (d, J=8.4 Hz, 1H, ArH), 7.78-7.68 (br.s, 1H, —NH), 7.67-7.57 (m, 2H, ArH), 7.52-7.40 (m, 2H, ArH), 7.32 (t, J=7.5 Hz, 1H, ArH), 4.31-4.19 (m, 1H), 4.18-4.02 (m, 2H), 3.82-3.58 (m, 6H), 3.56-3.46 (m, 1H), 2.67 (d, J=12.6 Hz, 1H), 2.58-2.38 (m, 4H), 2.20 (d, J=12.3 Hz, 1H), 2.16-2.02 (m, 1H), 1.65-1.51 (m, 1H). $^{13}$C NMR (75 MHz, $CDCl_3$): 175.52, 147.84, 146.43, 146.00, 139.06, 130.02, 129.59, 129.54, 127.21, 124.35, 124.32, 123.27, 122.60, 122.43, 120.72, 110.34, 59.88, 55.41, 54.76, 51.46, 47.05, 39.93, 37.84, 27.83. MS (ESI): m/z 430.2 [100%, $(M+H)^+$].

Preparation of Compound 11

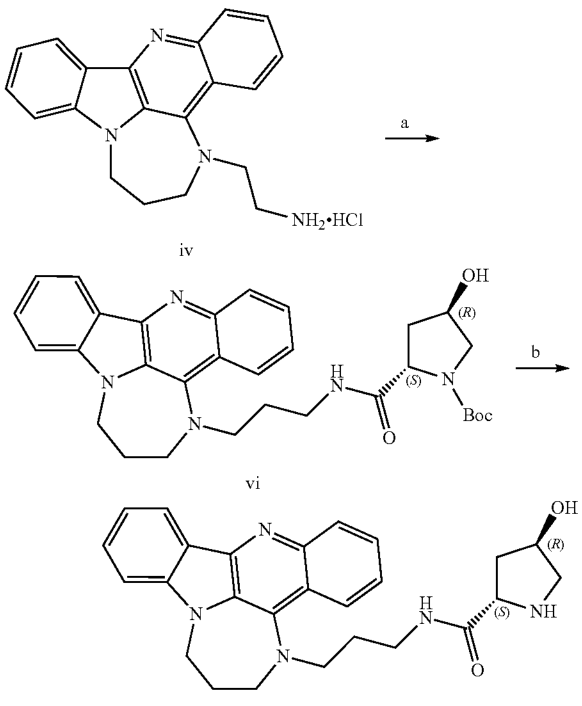

iv vi

11

(a) DIEA, Boc-trans-4-hydroxyl-L-proline, DCM, EDC•HCl, HOBt, RT; b) DCM, MeOH•HCl, liq. NH3

Preparation of Compound (vi)

This compound was synthesized using the similar procedure as described for compound (v) to yield compound (vi) in 66% yield as yellow color solid. $^1$H NMR (300 MHz, $CDCl_3$): δ 8.52 (d, J=7.8 Hz, 1H, ArH), 8.25 (d, J=8.4 Hz, 1H, ArH), 8.16 (d, J=8.1 Hz, 1H, ArH), 7.70-7.55 (m, 2H, ArH), 7.56-7.35 (m, 2H, ArH), 7.32 (t, J=7.5 Hz, 1H, ArH), 7.0 (br.s, 1H, —NH), 4.50-4.10 (m, 4H), 3.80-3.60 (m, 2H), 3.50-3.20 (m, 6H), 2.60-2.25 (m, 4H), 2.15-1.85 (m, 3H), 1.35 (s, 9H). MS (ESI): m/z 544.5 [100%, $(M+H)^+$].

Preparation of Compound (11)

This compound was synthesized using the similar procedure as described for compound 9 to yield compound 11. $^1$H NMR (300 MHz, $CDCl_3$): δ 8.53 (d, J=7.5 Hz, 1H, ArH), 8.26 (d, J=8.1 Hz, 1H, ArH), 8.18 (d, J=8.1 Hz, 1H, ArH), 7.75 (t, 1H, —CO—NH), 7.69-7.58 (m, 2H, ArH), 7.54-7.41 (m, 2H, ArH), 7.33 (t, J=7.5 Hz, 1H, ArH), 4.39-4.30 (m, 1H, —NH), 4.22 (t, J=5.8 Hz, 2H), 3.90 (t, J=8.25 Hz, 1H), 3.76-3.65 (m, 2H), 3.38 (t, J=7.65 Hz, 2H), 3.35-3.22 (m, 2H), 2.91 (d, J=12.0 Hz, 1H), 2.54 (dd, J=3.3 & 12.6 Hz, 1H), 2.50-2.21 (m, 5H), 2.20-1.92 (m, 2H), 1.85-1.70 (m, 1H). $^{13}$C NMR (75 MHz, $CDCl_3$): 174.93, 147.64, 145.91, 145.50, 139.00, 129.49, 129.33, 129.23, 126.61, 123.98, 123.86, 122.93, 122.83, 122.02, 120.15, 109.81, 73.02, 59.58, 55.19, 52.21, 50.31, 46.74, 39.79, 36.44, 28.93, 26.13. MS (ESI): m/z 444.4 [100%, $(M+H)^+$].

Preparation of Compound 5

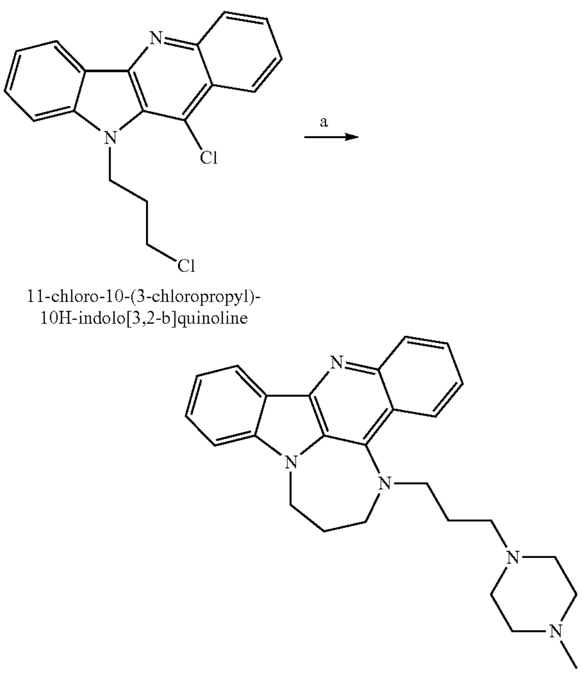

11-chloro-10-(3-chloropropyl)-10H-indolo[3,2-b]quinoline

5 a) 1-(3-aminopropyl)4-methylpiperazine, NaI, Neat, 100° C.

Preparation of Compound (5)

This compound was synthesized using the procedure similar to compound (iii). 1-(3-aminopropyl)-4-methylpiperazine (4.0 mL, excess) was used for the coupling reaction to yield compound 5 in 30% yield as yellow color solid. $^1H$ NMR (300 MHz, $CDCl_3$): δ 8.50 (d, J=7.8 Hz, 1H, ArH), 8.30-8.20 (m, 2H, ArH), 7.68-7.55 (m, 2H, ArH), 7.53-7.38 (m, 2H, ArH), 7.31 (t, J=7.3 Hz, 1H, ArH), 4.20 (t, J=5.7 Hz, 2H), 3.72-3.62 (m, 2H), 3.36 (t, J=7.95 Hz, 2H), 2.65-2.30 (m, 12H), 2.28 (s, 3H), 2.10-1.90 (m, 2H). $^{13}C$ NMR (75 MHz, $CDCl_3$): 148.11, 146.44, 145.89, 139.62, 129.83, 129.77, 126.96, 124.37, 123.50, 123.45, 122.39, 120.43, 110.11, 55.99, 55.49, 53.61, 52.75, 50.29, 47.12, 46.45, 26.48, 26.07. MS (ESI): m/z 414.5 [100%, $(M+H)^+$].

Preparation of Compound 18

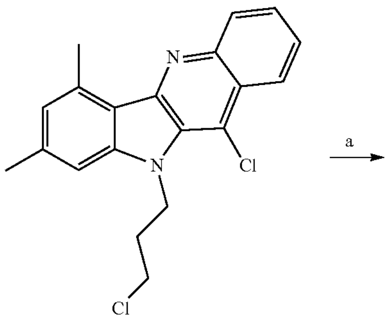

11-chloro-10-(3-chloropropyl)-6,8-dimethyl-10H-indolo[3,2-b]quinoline

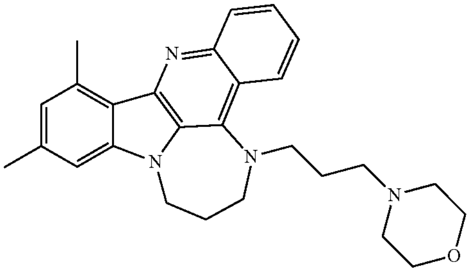

18 a) N-(3-aminopropyl)morpholine, NaI, Neat, 100° C.

Preparation of Compound (18)

This compound was synthesized using the procedure similar to compound (iii). N-(3-Aminopropyl)morpholine (4.0 mL, excess) was used for the coupling reaction to yield compound 18 in 41% yield as yellow color solid. $^1H$ NMR (300 MHz, $CDCl_3$): δ 8.31-8.21 (m, 2H, ArH), 7.68-7.55 (m, 1H, ArH), 7.52-7.42 (m, 1H, ArH), 7.07 (s, 1H, ArH), 6.92 (s, 1H, ArH), 4.18 (t, J=5.8 Hz, 2H), 3.80-3.62 (m, 6H), 3.38 (t, J=7.6 Hz, 2H), 3.17 (s, 3H), 2.55 (s, 3H), 2.52-2.31 (m, 8H), 2.09-1.95 (m, 2H). $^{13}C$ NMR (75 MHz, $CDCl_3$): 149.98, 146.88, 146.45, 139.62, 138.36, 136.72, 130.29, 126.41, 124.10, 123.96, 123.66, 122.90, 119.37, 107.69, 67.38, 56.51, 54.18, 52.52, 50.07, 46.99, 26.05, 25.83, 22.78, 19.94. MS (ESI): m/z 429.2 [100%, $(M+H)^+$].

Preparation of Compound 27

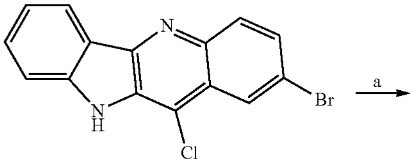

2-bromo-11-chloro-10H-indolo[3,2-b]quinoline

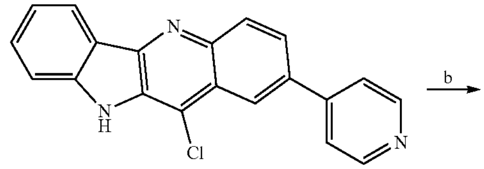

11-chloro-2-(pyridin-4-yl)-10H-indolo[3,2-b]quinoline

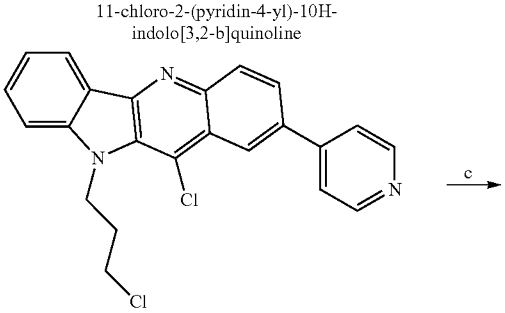

11-chloro-10-(3-chloropropyl)-2-(pyridin-4-yl)-10H-indolo[3,2-b]quinoline

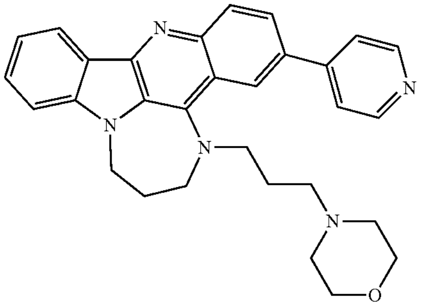

27

(a) 4-Pyridineboronic acid, $Pd(dppf)_2Cl_2$, $Na_2CO_3$, 1,2-dimethaxyethane:$H_2O$ (9:2), 90° C.; (b) 1-bromo-3-chloropropane, NaH, DMF, 0° C.-RT;
(c) N-(3-aminopropyl)morpholine, neat, 100° C.

Preparation of 11-chloro-2-(pyridin-4-yl)-10H-indolo[3,2-b]quinoline

A mixture of 2-bromo-11-chloro-10H-indolo[3,2-b]quinoline (200 mg, 0.60 mmol), 4-pyridineboronic acid (60 mg, 0.48 mmol), [1,1'-bis(diphenylphosphino)ferrocene]dichloro-palladium(II) (10 mol %), sodium carbonate (190 mg, 1.8 mmol) in 1,2-dimethoxyethane (9.0 mL) and water (2.0 mL) was heated under argon atmosphere at 90° C. for 4 h. After completion of the reaction as indicated by TLC (40% EtOAc in hexane), the reaction mixture was cooled to room temperature and the solvents were evaporated under vacuum. After addition of water (50 mL), the product was extracted with EtOAc (3x30 mL). The combined EtOAc layers were washed with water (2x50 mL), separated and dried over anhydrous $MgSO_4$, and finally concentrated under vacuum to get crude product. The crude product was then purified by silica gel column chromatography using 10-20% EtOAc in hexane as an eluent to afford 80 mg (40%) of pure 11-chloro-2-(pyridin-4-yl)-10H-indolo[3,2-b]quinoline as yellow color solid. $^{1}$H NMR (300 MHz, DMSO-$d_6$): δ 11.98 (br.s, 1H, —NH), 8.80-8.70 (m, 2H, ArH), 8.61 (s, 1H, ArH), 8.45-8.32 (m, 2H, ArH), 8.17 (d, J=8.7 Hz, 1H, ArH), 8.00-7.88 (m, 2H, ArH), 7.78-7.60 (m, 2H, ArH), 7.36 (t, J=6.7 Hz, 1H). MS (ESI): m/z 330.0 [100%, $(M+H)^+$].

Preparation of 11-chloro-10-(3-chloropropyl)-2-(pyridin-4-yl)-10H-indolo[3,2-b]quinoline To a stirred solution of 11-chloro-2-(pyridin-4-yl)-10H-indolo[3,2-b]quinoline (600 mg, 1.82 mmol) in dry DMF (15 mL) was added sodium hydride, 60% in mineral oil (174 mg, 7.28 mmol) at 0° C. The reaction mixture was stirred at 0° C. for 30 min, then 1-bromo-3-chloro-propane (572 mg, 3.64 mmol) was added slowly to the reaction mixture. After completion of the addition, the reaction mixture was stirred at room temperature for 4-5 h. After completion of the reaction as indicated by TLC, the mixture was poured in to ice cold water, after which the product was precipitated as solid. The solids were collected by filtration and washed with water (3×100 mL) and dried under vacuum to yield 600 mg (81%) of 11-chloro-10-(3-chloropropyl)-2-(pyridin-4-yl)-10H-indolo[3,2-b]quinoline as yellow color solid. $^{1}$H NMR (300 MHz, $CDCl_3$): δ 8.20-8.73 (m, 2H, ArH), 8.66 (d, J=1.8 Hz, 1H, ArH), 8.53 (d, J=7.5 Hz, 1H, ArH), 8.41 (d, J=8.7 Hz, 1H, ArH), 7.98 (dd, J=1.8 & 8.7 Hz, 1H, ArH), 7.78-7.68 (m, 3H, ArH), 7.59 (d, J=8.1 Hz, 1H, ArH), 7.41 (t, J=7.9 Hz, 1H), 4.95 (t, J=7.2 Hz, 2H), 3.68 (t, J=6.0 Hz, 2H), 2.51-2.35 (m, 2H). MS (ESI): m/z 406.0 [100%, $(M+H)^+$].

Preparation of Compound (27)

A mixture of 11-chloro-10-(3-chloropropyl)-2-(pyridin-4-yl)-10H-indolo[3,2-b]quinoline (350 mg, 0.86 mmol) and sodium iodide (231 mg, 1.5 mmol) in excess of 1-(3-aminopropyl)morpholine (3.0 mL) was stirred at 100° C. for 7 h. The progress of the reaction was monitored by TLC (10% MeOH in $CHCl_3$). After completion of the reaction, the reaction mixture was cooled to room temperature and poured into ice cold water and extracted with $CHCl_3$ (3×100 mL). The combined $CHCl_3$ layers were washed with water (4×200 mL), separated and dried over anhydrous $MgSO_4$, and finally concentrated under reduced pressure to give the crude product. The crude product was then purified by silica gel column chromatography using 8-10% MeOH in DCM as an eluent to afford 200 mg (48%) of pure compound (27) as yellow color solid. $^{1}$H NMR (300 MHz, $CDCl_3$): δ 8.78-8.69 (m, 2H, ArH), 8.57-8.49 (m, 2H, ArH), 8.36 (d, J=8.7 Hz, 1H, ArH), 7.92 (dd, J=2.1 & 8.7 Hz, 1H, ArH), 7.76-7.68 (m, 2H, ArH), 7.64 (td, J=1.2 & 7.2 Hz, 1H, ArH), 7.45 (d, J=8.1 Hz, 1H, ArH), 7.35 (t, J=7.5 Hz, 1H, ArH), 4.24 (t, J=5.8 Hz, 2H), 3.80-3.70 (m, 2H), 3.60-3.51 (m, 4H), 3.46 (t, J=7.65 Hz, 2H), 2.52-2.41 (m, 2H), 2.40-2.27 (m, 6H), 2.1-1.95 (m, 2H). $^{13}$C NMR (75 MHz, $CDCl_3$): 150.76, 149.00, 148.77, 146.52, 145.99, 139.88, 133.43, 130.81, 130.13, 129.91, 125.49, 123.38, 123.34, 123.25, 122.52, 122.11, 120.70, 110.20, 67.19, 56.60, 54.11, 53.31, 50.84, 47.22, 26.42, 26.39. MS (ESI): m/z 478.5 [100%, $(M+H)^+$].

Preparation of Compound 19

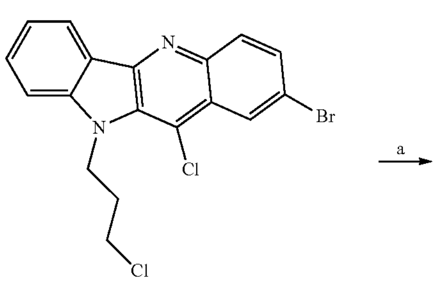

2-bromo-11-chloro-10-(3-chloropropyl)-10H-indolo[3,2-b]quinoline

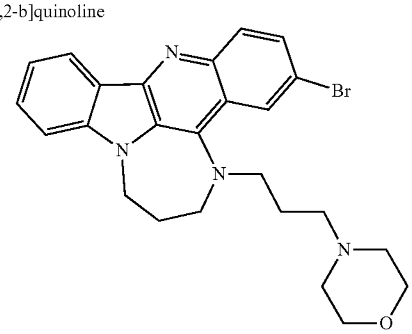

19

(a) N-(3-Aminopropyl)morpholine, Neat, 100° C.

Preparation of Compound (19)

This compound was synthesized using the procedure similar to compound (iii). N-(3-aminopropyl)morpholine (4.0 mL, excess) was used for the coupling reaction to yield compound 19 in 72.8% yield as yellow color solid. $^{1}$H NMR (300 MHz, $CDCl_3$): δ 8.47 (d, J=7.8 Hz, 1H, ArH), 8.35 (d, J=2.1 Hz, 1H, ArH), 8.11 (d, J=9.0 Hz, 1H, ArH), 7.67 (dd, J=2.1 & 9.0 Hz, 1H, ArH), 7.61 (t, J=8.1 Hz, 1H, ArH), 7.40 (d, J=8.4 Hz, 1H, ArH), 7.32 (t, J=7.3 Hz, 1H, ArH), 4.18 (t, J=5.7 Hz, 2H), 3.75-3.58 (m, 6H), 3.35 (t, J=7.6 Hz, 2H), 2.48-2.35 (m, 8H), 2.06-1.91 (m, 2H). $^{13}$C NMR (75 MHz, $CDCl_3$): 148.38, 145.88, 144.84, 138.51, 131.50, 130.16, 130.05, 129.78, 126.60, 124.66, 123.25, 122.39, 120.68, 118.19, 110.15, 67.35, 56.54, 54.12, 52.89, 50.48, 47.12, 26.11, 26.08. MS (ESI): m/z 481.2 [100%, $(M+H)^+$].

Preparation of Compound 28

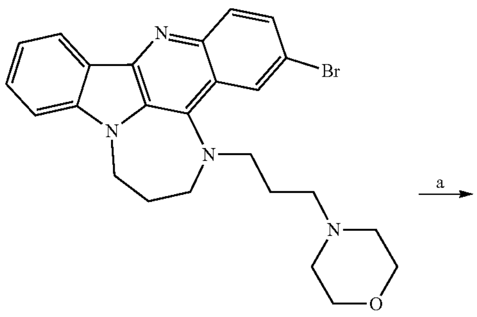

19

-continued

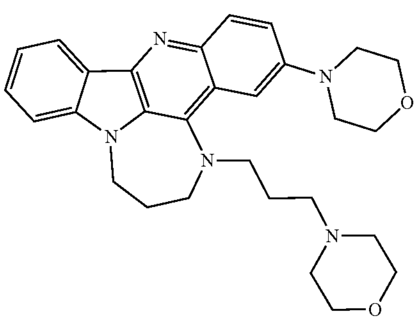

28

(a) Morpholine, Pd(dppf)$_2$Cl$_2$, NaO$^t$Bu, Neat, Microwave, 130° C.

Preparation of Compound (28)

A mixture of compound (19) (250 mg, 0.523 mmol), [1,1'-bis(diphenylphosphino)ferrocene]dichloropalladium (II) (38 mg, 10 mol %) sodium tert-butoxide (100 mg, 1.04 mmol) in morpholine (2 mL, excess) was reacted under microwave conditions at 130° C. for 30 min. After completion of the reaction as indicated by TLC (8% MeOH in EtOAc), the reaction mixture poured into cold water and extracted with DCM (3×50 mL). The combined DCM layers were washed with water (4×100 mL), separated and dried over anhydrous $MgSO_4$, and finally concentrated under reduced pressure to give the crude product. The crude product was then purified by silica gel column chromatography using 4-5% MeOH in EtOAc as an eluent to afford 130 mg (51%) of pure compound (28) as yellow color solid. $^1$H NMR (300 MHz, $CDCl_3$): δ 8.46 (d, J=7.5 Hz, 1H, ArH), 8.18 (d, J=9.9 Hz, 1H, ArH), 7.58 (t, J=7.6 Hz, 1H, ArH), 7.50-7.39 (m, 3H, ArH), 7.31 (t, J=7.5 Hz, 1H, ArH), 4.20 (t, J=5.7 Hz, 2H), 4.08-3.90 (m, 4H), 3.81-3.62 (m, 6H), 3.42-3.28 (m, 6H), 2.50-2.35 (m, 8H) 2.10-1.95 (m, 2H). $^{13}$C NMR (75 MHz, $CDCl_3$): 148.21, 146.28, 145.61, 142.41, 137.99, 130.81, 129.18, 124.34, 123.84, 121.95, 120.45, 120.23, 110.06, 106.06, 67.39, 67.32, 56.94, 54.23, 51.88, 50.44, 50.37, 47.07, 26.48, 26.00. MS (ESI): m/z 486.5 [100%, $(M+H)^+$].

Preparation of Compound 35

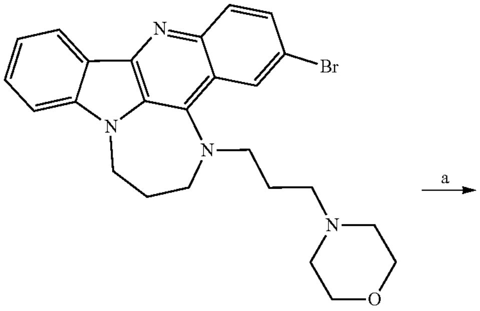

19

-continued

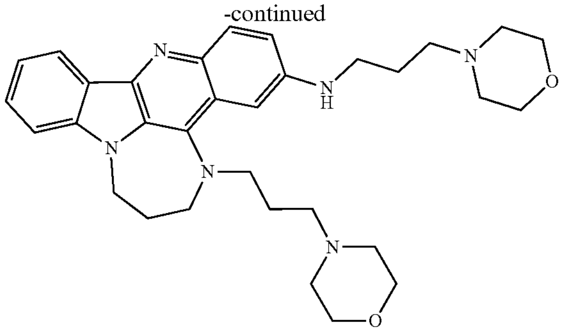

35

(a) N-(3-Aminopropyl)morpholine, Pd(dppf)$_2$Cl$_2$, NaO$^t$Bu, Neat, Microwave, 130° C.

Preparation of Compound (35)

This compound was synthesized using the procedure similar to compound 28. N-(3-aminopropyl)morpholine (4.0 mL, excess) was used for the coupling reaction to yield compound 16 in 35% yield as yellow color solid. $^1$H NMR (300 MHz, DMSO-d$_6$): δ 8.17 (d, J=7.5 Hz, 1H, ArH), 7.84 (d, J=9.0 Hz, 1H, ArH), 7.61 (d, J=8.4 Hz, 1H, ArH), 7.52 (t, J=7.5 Hz, 1H, ArH), 7.22 (t, J=7.3 Hz, 1H, ArH), 7.11 (dd, J=1.5 & 9.0 Hz, 1H, ArH), 6.87 (s, 1H, ArH), 6.12 (br.s, 1H, —NH), 4.28-4.12 (m, J=5.7 Hz, 2H), 3.62-3.43 (m, 12H), 3.30-3.12 (m, 4H), 2.48-2.20 (m, 12H), 2.05-1.90 (m, 2H), 1.89-1.77 (m, 2H). $^{13}$C NMR (75 MHz, DMSO-d$_6$): 146.42, 145.36, 143.36, 140.78, 137.02, 130.72, 130.54, 128.94, 125.46, 123.77, 121.04, 120.46, 120.38, 111.26, 98.14, 66.98, 57.19, 56.75, 54.29, 54.23, 50.99, 49.90, 47.08, 42.33, 26.15, 25.97, 25.35. MS (ESI): m/z 543.34 [100%, $(M+H)^+$].

Preparation of Compound 6

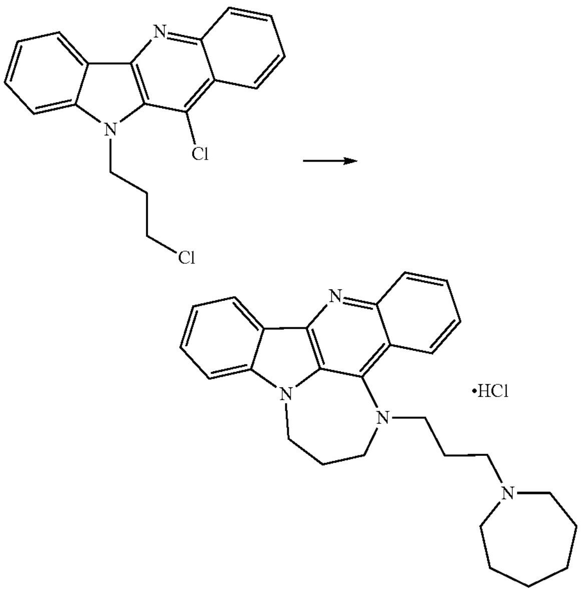

6

A mixture of 11-chloro-10-(3-chloropropyl)-6,8-dimethyl-10H-indolo[3,2-b]quinoline (350 mg, 1.06 mmol) and sodium iodide (394 mg, 2.65 mmol) in 3-(1-azapenyl)-1-propanamine (1.0 mL, 6.41 mmol) was reacted under microwave conditions at 150° C. for 35 min. After completion of the reaction, as indicated by TLC (10% MeOH in DCM), the reaction mixture was cooled to room temperature and poured into ice cold water and extracted with dichloromethane (DCM) (3×50 mL). The combined DCM layers were washed with water (4×100 mL), separated, dried over anhydrous $MgSO_4$, and finally concentrated under reduced pressure to give the crude product. The crude product was then purified by silica gel column chromatography using 5-8% MeOH in DCM as an eluent to afford 150 mg (34%) of compound as gummy oil. This gummy oil was treated with methanolic. HCl (3N, 2-3 mL) to make the hydrochloride salt (6). The hydrochloride salt was further purified by preparative HPLC (Zorbax sb C18, 250×22, 5 u, MeOH: $H_2O$:HCOOH, 40:60:0.25%) to yield pure product as yellow color solid. $^1$H NMR (300 MHz, $D_2O$): δ 7.69 (d, J=8.1 Hz, 1H, ArH), 7.62-7.51 (m, 2H, ArH), 7.46 (d, J=8.1 Hz, 1H, ArH), 7.38-7.18 (m, 2H, ArH), 7.06 (d, J=7.8 Hz, 1H, ArH), 6.97-6.82 (m, 1H, ArH), 3.92-3.75 (m, 2H), 3.68-3.46 (m, 4H), 3.30-3.15 (m, 2H), 3.05-2.88 (m, 2H), 2.87-2.70 (m, 2H), 2.25-1.95 (m, 4H), 1.80-1.58 (m, 4H), 1.57-1.48 (m, 4H). $^{13}$C NMR (75 MHz, $D_2O$): 148.25, 143.26, 135.63, 133.47, 132.12, 132.04, 126.26, 124.32, 122.79, 121.31, 121.22, 118.66, 117.37, 113.00, 111.05, 55.00, 54.67, 54.13, 52.22, 46.99, 26.47, 25.81, 23.71, 23.56. MS (ESI): m/z 413.3 [100%, $(M+H)^+$].

Preparation of Compound 12

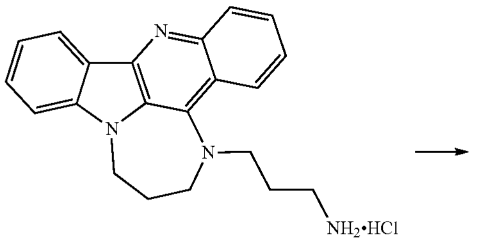

iv

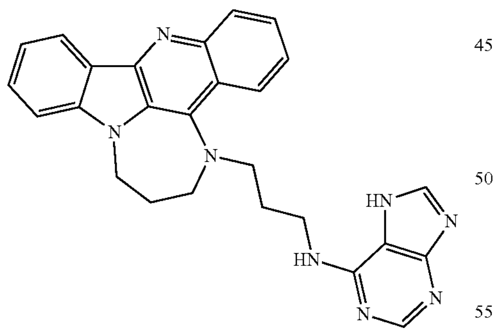

12

A mixture of compound (iv) (200 mg, 0.76 mmol), 6-chloropurine (126 mg, 0.81 mmol), potassium carbonate (149 mg, 1.08 mmol), and sodium iodide (160 mg, 1.08 mmol) in DMF (1 mL) was reacted under microwave conditions at 100° C. for 40 min. After completion of the reaction, as indicated by TLC, the reaction mixture was cooled to room temperature. Then the reaction mixture was diluted with water (50 mL) and extracted with DCM (3×40 mL). The combined organic layer was washed with water and dried over anhydrous sodium sulfate, and the DCM was evaporated under vacuum to get the crude product. The crude product was then purified by silica gel column chromatography using 5-8% MeOH in DCM as an eluent to yield 80 mg (33%) of compound 12 as yellow color solid. $^1$H NMR (300 MHz, DMSO-$d_6$): δ 12.90 (br.s, 1H, —NH), 8.30 (d, J=7.8 Hz, 1H, ArH), 8.23-8.01 (m, 4H, ArH), 7.78-7.59 (m, 3H, ArH), 7.54 (t, J=7.5 Hz, 1H, ArH), 7.29 (t, J=7.2 Hz, 1H, ArH), 7.25-7.15 (br.s, 1H, —NH), 4.26 (t, J=5.1 Hz, 2H), 3.72-3.50 (m, 4H), 3.42 (t, J=6.9 Hz, 2H), 2.43-2.30 (m, 2H), 2.29-2.10 (m, 2H). $^{13}$C NMR (75 MHz, DMSO-$d_6$): 153.19, 145.96, 145.82, 140.24, 139.46, 130.37, 129.41, 129.23, 127.33, 124.92, 124.39, 123.00, 122.77, 121.99, 120.71, 111.55, 52.57, 50.39, 47.24, 25.90. MS (ESI): m/z 449.2 [100%, $(M+H)^+$].

Preparation of Compound 13

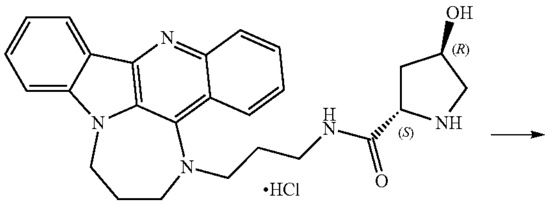

11

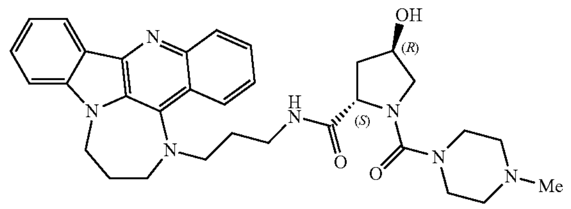

13

A mixture of compound (11) (HCl salt, 200 mg, 0.41 mmol), DIEA (0.23 mL, 1.25 mmol) in DCM (10 mL) was stirred at ice bath temperature for 15 min. 4-Methyl piperazine carbonylchloride hydrochloride (132 mg, 0.66 mmol) was added to the reaction mixture. After completion of the addition, the reaction mixture was stirred at room temperature for overnight. The completion of the reaction was monitored by TLC. After evaporation of DCM, the reaction mixture was diluted with water and extracted with DCM (3×40 mL). The combined organic layer was washed with water and dried over anhydrous sodium sulfate, and concentrated under vacuum to get the crude product. The crude product was then purified by silica gel chromatography using 20% MeOH in DCM as an eluent to get 150 mg (63%) of compound (13) as yellow color solid. $^1$H NMR (300 MHz, $CDCl_3$): δ 8.50 (d, J=7.8 Hz, 1H, ArH), 8.23 (d, J=8.1 Hz, 1H, ArH), 8.16 (d, J=8.7 Hz, 1H, ArH), 7.68-7.54 (m, 2H, ArH), 7.47 (t, J=7.5 Hz, 1H, ArH), 7.40 (d, J=8.4 Hz, 1H, ArH), 7.31 (t, J=8.2 Hz, 1H, ArH), 6.88 (br. t, 1H, NH), 4.68 (t, J=8.7 Hz, 1H), 4.40-4.29 (br.s, 1H), 4.28-4.03 (m, 2H), 3.72-3.53 (m, 2H), 3.48-3.18 (m, 8H), 3.16-2.98 (m, 2H), 2.45-2.14 (m, 7H), 2.13 (s, 3H, —N-Me), 2.10-1.92 (m, 4H). $^{13}$C NMR (75 MHz, $CDCl_3$): 172.60, 163.54, 147.92, 146.21, 145.91, 139.58, 129.93, 129.71, 129.47, 127.09, 124.45, 124.37, 123.25, 123.22, 122.45, 120.59, 110.23, 70.85, 59.78, 59.56, 54.99, 52.50, 50.53, 47.11, 46.33, 46.11, 37.66, 37.33, 28.93, 28.36. MS (ESI): m/z 570.2 [100%, $(M+H)^+$].

Preparation of Compound 33

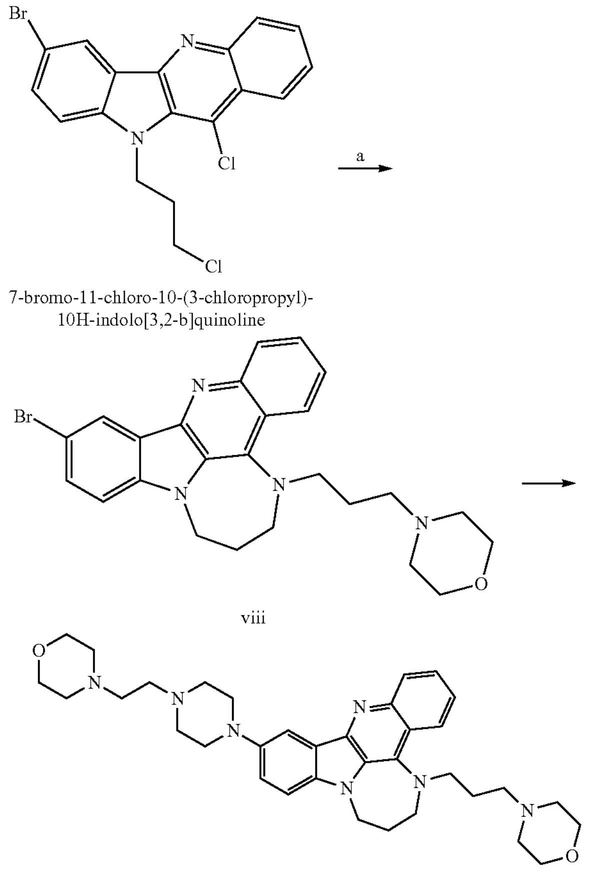

7-bromo-11-chloro-10-(3-chloropropyl)-10H-indolo[3,2-b]quinoline viii

33

(a) N-(3-Aminorpopyl)morpholine, Neat, 100° C.

Preparation of Compound (viii)

This compound was synthesized using the procedure similar to compound (iii). N-(3-aminopropyl)morpholine (4.0 mL, excess) was used for the coupling reaction to yield compound 17 in 73% yield as yellow color solid. $^1$H NMR (300 MHz, $CDCl_3$): δ 8.63 (d, J=1.8 Hz, 1H, ArH), 8.32-8.18 (m, 2H, ArH), 7.72-7.61 (m, 2H, ArH), 7.49 (td, J=1.2 & 8.4 Hz, 1H, ArH), 7.32-7.24 (m, 1H, ArH), 4.17 (t, J=5.8 Hz, 2H), 3.78-3.61 (m, 6H), 3.40 (t, J=7.6 Hz, 2H), 2.50-2.30 (m, 8H), 2.08-1.91 (m, 2H). $^{13}$C NMR (75 MHz, $CDCl_3$): 146.59, 144.31, 139.95, 132.23, 129.86, 129.79, 127.29, 125.25, 125.00, 124.57, 124.46, 123.46, 113.29, 111.64, 67.33, 56.34, 54.13, 52.80, 50.42, 47.29, 26.18, 26.12. MS (ESI): m/z 481.1 [100%, $(M+H)^+$].

Preparation of Compound (33)

To a stirred solution of compound (viii) (200 mg, 0.41 mmol) and 1-(2-morpholin-4-yl)ethyl piperazine in toluene (8 mL) under argon purging were added $Pd_2(dba)_3$ (36 mg, 10 mol %), (Rac) BINAP (25 mg 10 mol %) and sodium t-butoxide (78 mg, 0.82 mmol). The reaction mixture was stirred at 110° C. for 4-5 h under argon atmosphere. After completion of the reaction was indicated by TLC, the reaction mixture was cooled to room temperature. Then the reaction mixture was diluted with water (50 mL) and extracted with EtOAc (3×50 mL). The combined organic layer was washed with water, dried over anhydrous sodium sulfate, and the solvent was evaporated under vacuum to afford the crude product. The crude product was then purified by silica gel chromatography using 15% MeOH in DCM as an eluent to yield 120 mg (33%) of compound (33) as yellow color solid. $^1$H NMR (300 MHz, $CDCl_3$): δ 8.30-8.20 (m, 2H, ArH), 8.04 (s, 1H, ArH), 7.63 (t, J=7.6 Hz, 1H, ArH), 7.48 (t, J=7.6 Hz, 1H, ArH), 7.40-7.32 (m, 2H, ArH), 4.16 (t, J=5.7 Hz, 2H), 3.83-3.73 (m, 4H), 3.72-3.61 (m, 6H), 3.41 (t, J=7.5 Hz, 2H), 3.38-3.27 (m, 4H), 2.83-2.71 (m, 4H), 2.70-2.60 (m, 4H), 2.59-2.49 (m, 4H), 2.48-2.31 (m, 8H), 2.10-1.95 (m, 2H). $^{13}$C NMR (75 MHz, $CDCl_3$): 148.25, 146.46, 146.29, 141.20, 139.58, 130.72, 129.74, 126.83, 124.33, 124.19, 124.08, 123.39, 121.75, 110.81, 109.15, 67.40, 67.34, 56.82, 56.42, 56.15, 54.62, 54.30, 54.13, 52.67, 51.53, 50.52, 47.29, 26.39, 26.17. MS (ESI): m/z 598.5 [100%, $(M+H)^+$].

Compound 26

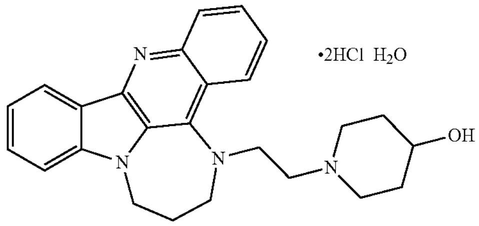

$^1$H NMR ($D_2O$, 500 MHz): δ 7.66 (d, J=8.5 Hz, 1H, ArH), 7.55 (t, J=7.7 Hz, 1H, ArH), 7.46 (d, J=8.5 Hz, 1H, ArH), 7.42-7.34 (m, 2H, ArH), 7.04 (t, J=7.7 Hz, 1H, ArH), 6.89 (d, J=8.5 Hz, 1H, ArH), 6.67 (t, J=7.2 Hz, 1H, ArH), 4.05-3.82 (m, 3H), 3.81-3.72 (m, 2H), 3.62-3.55 (m, 2H), 3.54-3.48 (m, 2H), 3.47-3.22 (m, 2H), 3.21-3.0 (m, 2H), 2.28-2.15 (m, 2H), 2.14-1.85 (m, 2H), 1.83-1.52 (m, 2H).

$^{13}$C NMR ($D_2O$, 250 MHz): 147.38, 143.58, 135.58, 134.35, 132.42, 132.36, 125.61, 125.34, 123.90, 121.40, 119.21, 117.91, 112.89, 111.11, 53.80, 52.49, 51.48, 47.16, 26.48.

HRMS: Found=401.2341 ($MH^+$) (Theoretically=401.2336) Error=−1.5 ppm

Compound 15

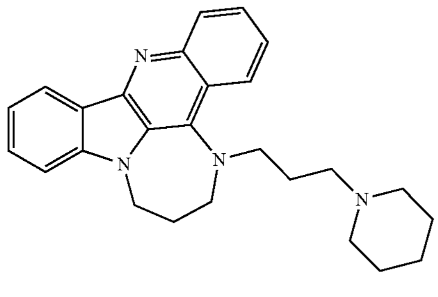

$^1$H NMR (300 MHz, $CDCl_3$): δ 8.52 (d, J=7.5 Hz, 1H), 8.32-8.21 (m, 2H), 7.70-7.56 (m, 2H), 7.55-7.45 (m, 1H), 7.42 (d, J=8.1 Hz, 1H), 7.30 (t, J=7.5 Hz, 1H), 4.15-4.28 (m, 2H), 3.72-3.65 (m, 2H), 3.35 (t, J=7.5 Hz, 2H), 2.50-2.25 (m, 8H), 2.04 (q, 2H), 1.59 (q, 4H), 1.55-1.38 (m, 2H).

$^{13}$C-NMR (75 MHz, $CDCl_3$): δ 148.12, 146.47, 145.87, 139.69, 129.81, 129.79, 129.72, 126.93, 124.40, 124.35, 123.51, 123.48, 122.36, 120.37, 110.10, 56.93, 55.15, 52.87, 50.14, 47.11, 26.66, 26.43, 25.91, 24.86.

HRMS: 399.2543 $MH^+$ (Theoretically=399.2543) Error=0.1 ppm.

Compound 16

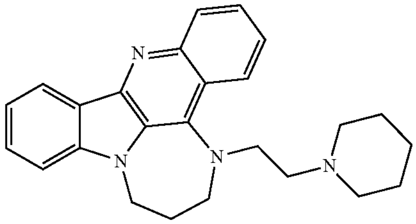

$^1$H NMR (300 MHz, $CDCl_3$): δ 8.52 (d, J=7.8 Hz, 1H), 8.340 (d, J=8.4 Hz, 1H), 8.27 (d, 8.4 Hz, 1H), 7.71-7.58 (m, 2H), 7.51 (t, J=7.8 Hz, 1H), 7.43 (d, J=8.4 Hz, 1H), 7.32 (t, J=7.5 Hz, 1H), 4.23 (t, J=6.0, 2H), 3.78-3.68 (m, 2H), 3.51 (t, J=6.9 Hz, 2H), 2.77 (t, J=7.2, 2H), 2.50-2.35 (m, 6H), 1.55 (q, 4H), 1.49-1.38 (m, 2H).

$^{13}$C-NMR (75 MHz, $CDCl_3$): δ 148.05, 146.45, 145.82, 139.59, 129.78, 129.72, 126.94, 124.44, 124.25, 123.46, 123.37, 122.38, 120.35, 110.05, 58.26, 55.61, 52.30, 50.88, 47.04, 26.37, 24.71.

HRMS: 385.2392 $MH^+$ (Theoretically=385.2386) Error=−1.4 ppm.

Compound 50

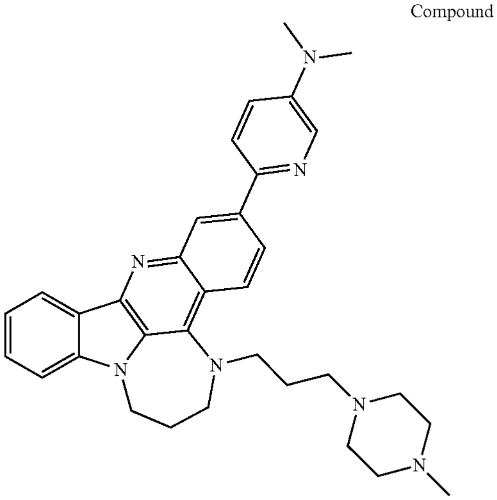

$^1$H NMR (300 MHz, $CDCl_3$): δ 8.69 (d, J=2.1 Hz, 1H), 8.53 (d, J=7.5 Hz, 1H), 8.41 (d, 1.2 Hz, 1H), 8.28 (d, J=8.7 Hz, 1H), 7.96 (dd, J=2.4 & 9.0 Hz, 1H), 7.72 (dd, J=1.5 & 9.0 Hz, 1H), 7.61 (t, J=7.5 Hz, 1H), 7.44 (d, J=8.4 Hz, 1H), 7.33 (t, J=7.5 Hz), 6.67 (d, J=8.7 Hz, 1H), 4.22 (t, J=5.7 Hz, 2H), 3.77-3.68 (m, 2H), 3.42 (t, J=7.5 Hz, 2H), 3.18 (s, 3H), 2.60-2.45 (m, 12H), 2.29 (s, 3H), 2.03 (q, 2H).

$^{13}$C-NMR (75 MHz, $CDCl_3$): δ 159.06, 148.40, 146.95, 146.78, 145.83, 139.70, 137.02, 136.37, 129.74, 129.59, 125.44, 125.10, 124.34, 123.45, 123.08, 122.38, 122.05, 120.43, 110.13, 106.35, 55.97, 55.48, 53.60, 52.89, 50.39, 47.14, 46.45, 38.67, 26.52, 26.17.

HRMS: 534.3346 $MH^+$ (Theoretically=534.3340) Error=−1.1 ppm.

Compound 59

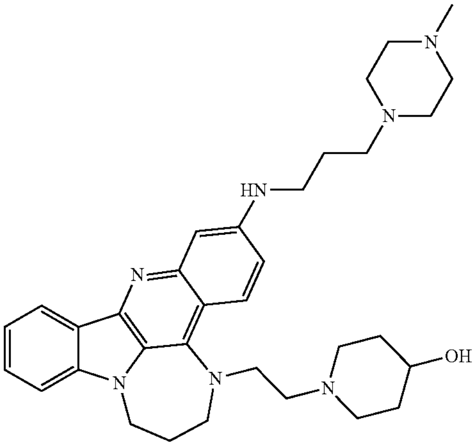

$^1$H NMR (300 MHz, DMSO-$d_6$): δ 8.21 (d, J=7.8 Hz, 1H), 8.10 (d, J=9.3 Hz, 1H), 7.69-7.45 (m, 2H), 7.21 (t, J=9.0, 1H), 6.97 (d, J=9.3, 1H), 6.89 (brs, 1H), 6.16 (brs, 1H), 4.59 (brs, 1H), 4.17 (t, J=5.1 Hz, 2H), 3.58 (d, J=6 Hz, 2H), 3.45-3.25 (m, 3H), 3.23-3.10 (m, 2H), 2.80-2.59 (m, 3H), 2.48-2.27 (m, 11H), 2.18 (s, 3H), 2.05 (t, J=9.0 Hz, 3H) 1.78 (quin, 2H), 1.70-1.55 (M, 2H), 1.42-1.20 (m, 2H).

$^{13}$C-NMR (75 MHz, DMSO-$d_6$): δ 148.71, 148.62, 145.29, 141.34, 129.46, 127.57, 125.54, 122.91, 121.65, 120.15, 117.63, 115.46, 111.36, 103.07, 67.04, 57.04, 56.58, 55.50, 53.42, 52.68, 52.34, 50.86, 47.15, 46.41, 42.04, 35.25, 26.45, 26.20.

HRMS: 556.3758 $MH^+$ (Theoretically=556.3758) Error=0.1 ppm.

Compound 60

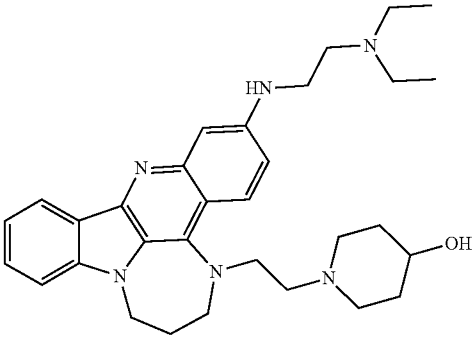

$^1$H NMR (300 MHz, DMSO-$d_6$): δ 8.20 (d, J=7.8 Hz, 1H), 8.11 (d, J=9.3 Hz, 1H), 7.65-7.50 (m, 2H), 7.22 (t, J=7.2 Hz, 1H), 7.00 (dd, J=2.4 & 9.3 Hz, 1H), 6.93 (d, 2.1 Hz, 1H), 5.92 (brs, 1H), 4.60 (brs, 1H), 4.18 (t, J=5.7 Hz, 2H), 3.58 (d, J=5.7 Hz, 2H), 3.45-3.21 (m, 3H), 3.20-3.15 (m, 2H), 2.85-2.55 (m, 10H, merged with DMSO-$d_6$ signal), 2.50 (t, J=1.8 Hz, 2H), 2.38-2.25 (m, 2H), 2.04 (t, J=9.9 Hz, 2H) 1.72-1.58 (m, 2H), 1.45-1.25 (m, 2H), 1.02 (t, J=6.9 Hz, 6H).

$^{13}$C-NMR (75 MHz, DMSO-$d_6$): δ 148.69, 148.37, 146.41, 145.35, 141.13, 129.47, 127.70, 125.58, 123.04, 121.65, 120.61, 117.67, 115.71, 111.36, 103.60, 67.06, 57.07, 52.66, 52.37, 51.84, 50.85, 47.40, 47.15, 35.28, 26.20, 12.24.

Compound 61

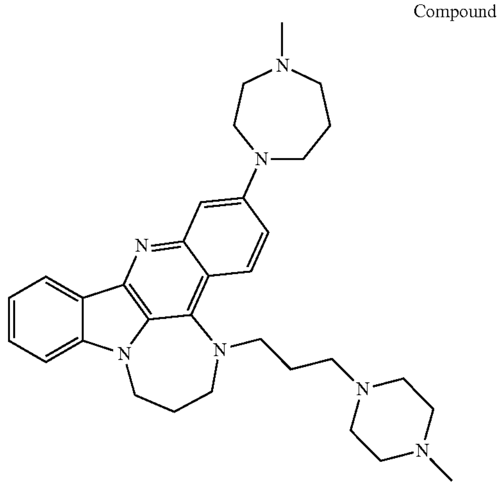

$^1$H NMR (300 MHz, $CDCl_3$): δ 8.52 (d, J=7.8 Hz, 1H), 8.07 (d, J=9.3 Hz, 1H), 7.62-7.53 (m, 1H), 7.45-7.33 (m, 1H), 7.28 (t, J=6.0 Hz, 1H), 7.13 (dd, J=2.4 & 9.3 Hz, 1H), 4.18 (t, J=6.0 Hz, 2H), 3.78 (t, J=3.0 Hz, 2H), 3.78-3.60 (m, 4H), 3.39 (t, J=6.0), 2.83 (t, J=3.0, 2H), 2.61 (t, J=6.0, 3H), 2.53-2.35 (m, 11H), 2.30 (s, 3H), 2.12 (q, 2H), 2.02 (q, 2H).

$^{13}$C-NMR (75 MHz, DMSO-$d_6$): δ 148.64, 148.31, 147.26, 145.57, 140.75, 129.57, 127.61, 125.82, 123.28, 121.69, 120.17, 115.36, 114.66, 111.37, 105.85, 58.08, 57.17, 55.61, 53.46, 52.67, 50.34, 49.14, 48.79, 47.30, 46.90, 46.60, 27.83, 26.04.

HRMS: 526.3653 $MH^+$ (Theoretically=526.3652) Error=0.1 ppm

Compound 62

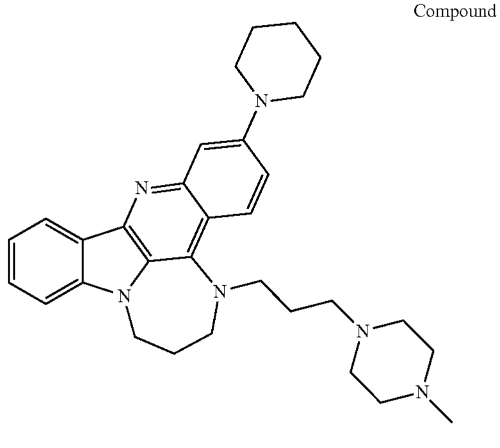

$^1$H NMR (300 MHz, $CDCl_3$): δ 8.73 (d, J=7.5 Hz, 1H), 7.94 (d, J=9.3 Hz, 1H), 7.22 (s, 1H), 7.53 (t, J=6.0 Hz, 1H), 7.35 (d, J=8.4 Hz), 7.30-7.18 (m, 2H), 4.21 (t, J=5.4 Hz, 2H), 3.71 (t, J=4.5 Hz, 2H), 3.50 (t, J=6.0 Hz), 3.41 (t, J=4.5), 2.60-2.23 (m, 15H), 1.97 (q, 2H), 1.85-1.55 (m, 6H).

$^{13}$C-NMR (75 MHz, ($CDCl_3$): δ 151.95, 145.20, 144.81, 143.60, 130.05, 126.72, 125.62, 123.59, 120.73, 120.48, 117.43, 115.26, 110.14, 106.84, 55.53, 55.12, 54.22, 53.01, 51.25, 50.29, 47.31, 46.06, 30.11, 26.88, 26.52, 26.09, 24.77.

HRMS: 497.33824 $MH^+$ (Theoretically=497.33872) Error=1 ppm.

Compound 63

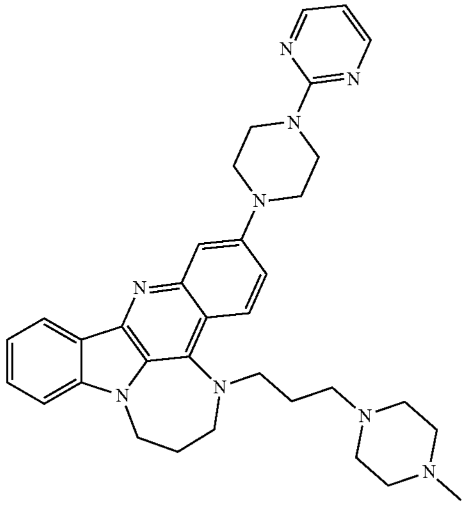

$^1$H NMR (300 MHz, $CDCl_3$): δ 8.63 (d, J=7.5 Hz, 1H), 8.36 (d, J=4.8 Hz, 2H), 8.04 (d, J=9.3 Hz), 7.69 (s, 1H), 7.55 (t, J=8.4 Hz, 1H), 7.37 (d, J=8.4 Hz), 7.38-7.23 (m, 2H), 6.54 (t, J=6.0 Hz, 1H), 4.19 (t, J=5.7 Hz, 2H), 4.05 (t, J=3.0 Hz, 4H), 3.69 (t, J=3.0 Hz, 2H), 3.55-3.35 (m, 7H), 2.70-2.25 (m, 15H), 2.00 (q, 2H).

$^{13}$C-NMR (75 MHz, ($CDCl_3$): δ 162.02, 158.21, 150.93, 146.03, 145.12, 142.34, 129.95, 128.15, 127.53, 125.69, 123.09, 121.50, 120.61, 117.40, 116.56, 110.64, 110.17, 108.96, 55.60, 55.10, 53.80, 52.98, 51.01, 49.25, 47.26, 46.05, 43.95, 26.69, 26.47.

HRMS: 576.3553 $MH^+$ (Theoretically=576.3558) Error=0.8 ppm.

Compound 64

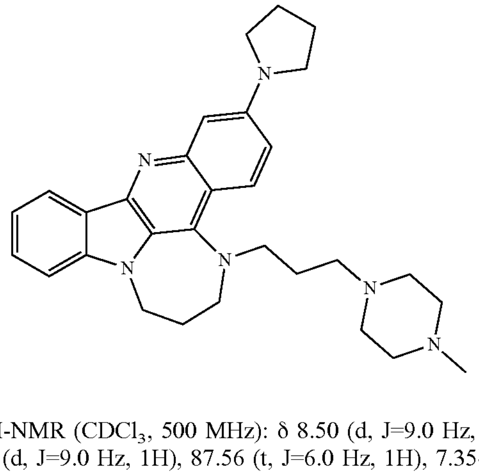

$^1$H-NMR ($CDCl_3$, 500 MHz): δ 8.50 (d, J=9.0 Hz, 1H), 8.06 (d, J=9.0 Hz, 1H), 87.56 (t, J=6.0 Hz, 1H), 7.35-7.19 (m, 2H, ArH), 7.02 (d, J=9.0 Hz, 1H), 4.16 (t, J=6.0 Hz, 2H), 3.75-3.61 (m, 2H), 3.58-3.45 (m, 4H), 3.36 (t, J=9.0 Hz, 2H), 2.65-2.25 (m, 11H), 2.30 (s, 3H), 2.19-1.95 (m, 7H).

$^{13}$C-NMR ($CDCl_3$): 148.46, 147.38, 145.52, 140.98, 129.18, 127.95, 125.19, 123.42, 122.37, 119.98, 115.53, 114.79, 110.05, 105.76, 56.10, 55.47, 53.60, 53.08, 50.42, 48.28, 47.18, 46.43, 30.12, 26.60, 26.27, 25.99

HRMS: 483.32355 $MH^+$ (Theoretically=483.32307) Error=−1.0 ppm

Compound 29

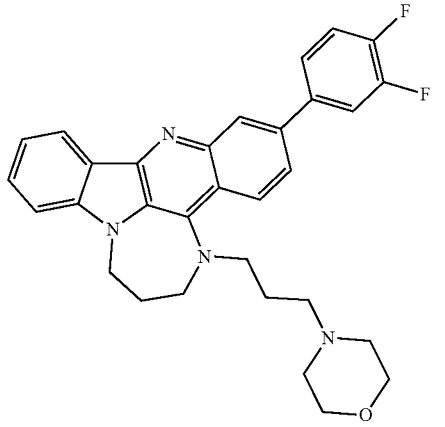

$^1$H-NMR ($CDCl_3$, 500 MHz): δ 8.54 (d, J=8.0 Hz, 1H, ArH), 8.45 (s, 1H, ArH), 8.31 (d, J=9.0 Hz, 1H, ArH), 7.70-7.60 (m, 3H, ArH), 7.59-7.52 (m, 1H, ArH), 7.45 (d, J=8.5 Hz, 1H, ArH), 7.36 (t, J=7.5 Hz, 1H, ArH), 7.32-7.28 (m, 1H, ArH), 4.24 (t, J=5.7 Hz, 2H), 3.75-3.63 (m, 6H), 3.44 (t, J=7.5 Hz, 2H), 2.50-2.35 (m, 8H) 2.10-2.0 (m, 2H).

$^{13}$C-NMR ($CDCl_3$): 152.77, 152.60, 152.14, 151.97, 149.49, 149.32, 148.85, 148.71, 146.54, 145.90, 139.48, 138.36, 138.30, 138.28, 138.23, 137.28, 129.99, 129.78, 127.38, 125.33, 123.60, 123.55, 123.52, 123.47, 123.34, 123.14, 122.71, 122.42, 120.62, 118.17, 117.94, 116.61, 116.38, 110.17, 67.35, 56.40, 54.15, 52.91, 50.58, 47.17, 26.26, 26.17.

HRMS Found=513.2453 ($MH^+$) (Theoretically=513.6008) Error=1.5 ppm

Compound 31

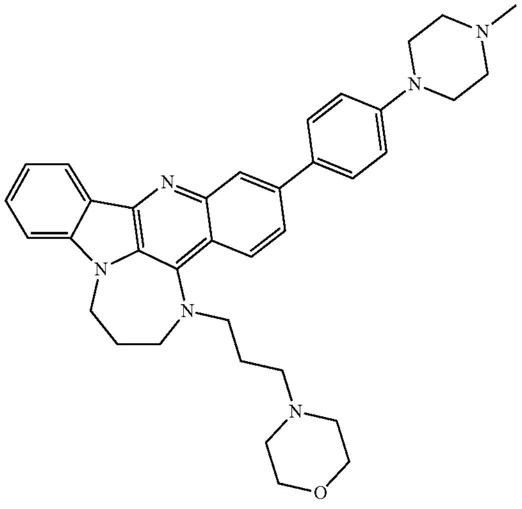

$^1$H-NMR ($CDCl_3$, 300 MHz): δ 8.55 (d, J=7.5 Hz, 1H, ArH), 8.48 (s, 1H, ArH), 8.26 (d, J=8.7 Hz, 1H, ArH), 7.88-7.70 (m, 3H, ArH), 7.62 (t, J=7.3 Hz, 1H, ArH), 7.44 (d, J=8.1 Hz, 1H, ArH), 7.33 (t, J=7.3 Hz, 1H, Ar·H), 7.08 (d, J=7.5 1H, ArH), 4.30-4.18 (m, 2H), 3.80-3.62 (m, 6H), 3.44 (t, J=6.6 Hz, 2H), 3.4-3.28 (m, 4H), 2.72-2.58 (m, 4H), 2.54-2.30 (m, 11H) 2.12-1.92 (m, 2H).

$^{13}$C-NMR ($CDCl_3$): 150.99, 148.19, 146.83, 145.83, 139.74, 139.26, 131.89, 129.75, 129.54, 128.32, 125.86, 124.80, 123.58, 123.39, 122.48, 121.99, 120.47, 116.50, 110.114, 67.35, 56.43, 55.48, 54.16, 52.87, 50.54, 49.16, 47.18, 46.55, 26.27, 26.17.

HRMS: Found=575.3490 ($MH^+$) (Theoretically=575.3493) Error=0.5 ppm

Compound 32

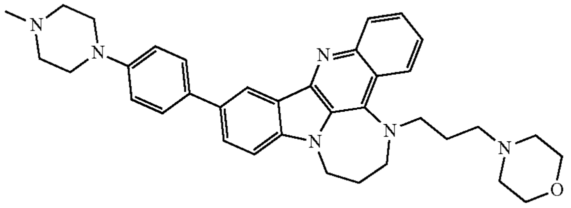

$^1$H-NMR ($CDCl_3$, 500 MHz): δ 8.73 (d, J=1.5 Hz, 1H, ArH), 8.29 (d, J=5.1 Hz, 1H, ArH), 8.27 (d, J=8.5 Hz, 1H, ArH), 7.85 (dd, J=1.5 & 8.5 Hz, 1H, Ar·H), 7.71 (d, J=8.5 Hz, 2H, Ar·H), 7.65 (t, J=7.5 Hz, 1H, ArH), 7.50 (t, J=7.5 Hz, 1H, Ar·H), 7.46 (d, J=8.5 Hz, 1H, ArH), 7.06 (d, J=9.0 Hz, 2H, ArH), 4.23 (t, J=5.7 Hz, 2H), 3.75-3.65 (m, 6H), 3.43 (t, J=7.7 Hz, 2H), 3.35-3.28 (m, 4H), 2.72-2.62 (m, 4H), 2.48-2.38 (m, 11H) 2.08-1.98 (m, 2H).

$^{13}$C-NMR ($CDCl_3$): 150.45, 148.11, 146.33, 144.91, 13974, 133.63, 132.85, 130.24, 129.70, 128.66, 128.16, 127.05, 124.40, 124.31, 123.94, 123.41, 119.85, 116.66, 110.37, 67.32, 56.39, 55.49, 54.13, 52.77, 50.52, 49.34, 47.27, 46.50, 26.29, 26.14.

HRMS: Found=575.3486 ($MH^+$) (Theoretically=575.3493) Error=1.2 ppm

Compound 39

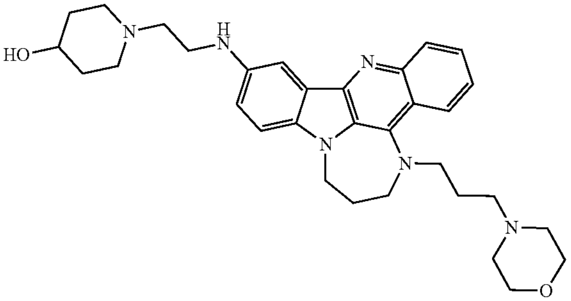

$^1$H-NMR ($CDCl_3$, 500 MHz): δ 8.35-8.22 (m, 2H, ArH), 7.74 (s, 1H, ArH), 7.63 (t, J=7.5 Hz, 1H, Ar·H), 7.48 (t, J=7.7 Hz, 1H, ArH), 7.34-7.26 (m, 1H, ArH, merged with $CDCl_3$ peak), 7.06 (d, J=8.5 Hz, 1H, Ar·H), 6.85-6.70 (brs, 1H, —NH), 4.13 (t, J=5.5 Hz, 2H), 3.85-3.62 (m, 7H), 3.42 (t, J=7.7 Hz, 2H), 3.33 (t, J=5.7 Hz, 2H), 2.92-2.77 (m, 2H), 2.72 (t, J=5.5 Hz, 2H), 2.55-2.33 (m, 9H), 2.32-2.18 (m, 2H), 2.12-1.88 (m, 4H), 1.72-1.60 (m, 2H).

$^{13}$C-NMR ($CDCl_3$): 148.21, 146.06, 143.61, 139.96, 139.61, 130.88, 129.56, 128.06, 126.76, 124.32, 124.11, 123.35, 118.84, 111.12, 104.23, 68.21, 67.33, 56.98, 56.43, 54.13, 52.64, 51.20, 50.51, 47.34, 42.14, 34.80, 26.45, 26.18.

HRMS: Found=543.3441 ($MH^+$) (Theoretically=543.7228) Error=0.2 ppm

Compound 37

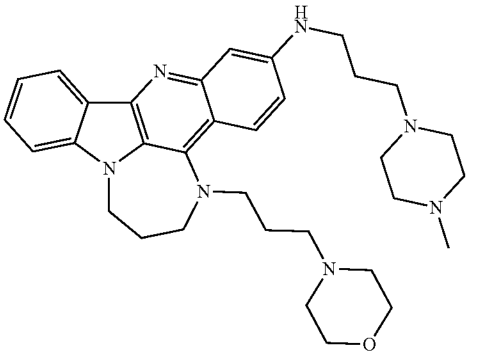

$^1$H-NMR ($CDCl_3$, 500 MHz): δ 8.51 (d, J=8.0 Hz, 1H, ArH), 8.03 (d, J=9.0 Hz, 1H, ArH), 7.58 (t, J=7.5 Hz, 1H, ArH), 7.41 (d, J=8.5 Hz, 1H, Ar·H), 7.33-7.25 (m, 1H, Ar·H, merged with $CDCl_3$ peak), 7.24 (d, J=1.5 Hz, 1H, ArH), 6.90 (dd, J=2.0 & 9.0 Hz, 1H, Ar·H), 5.35-5.05 (brs, 1H, —NH), 4.18 (t, J=5.7 Hz, 2H), 3.80-3.50 (m, 6H), 3.45-3.32 (m, 4H), 2.70-2.55 (m, 6H), 2.54-2.28 (m, 15H) 2.08-1.85 (m, 4H).

$^{13}$C-NMR ($CDCl_3$): 148.63, 148.14, 145.47, 141.05, 129.20, 128.24, 125.17, 123.36, 122.39, 120.12, 117.22, 116.41, 110.07, 104.76, 67.36, 57.88, 56.45, 55.78, 54.15, 53.67, 53.03, 50.54, 47.16, 46.48, 44.16, 26.34, 26.17, 25.79.

HRMS: Found=556.3747 ($MH^+$) (Theoretically=556.3747) Error=2.0 ppm

Compound 42

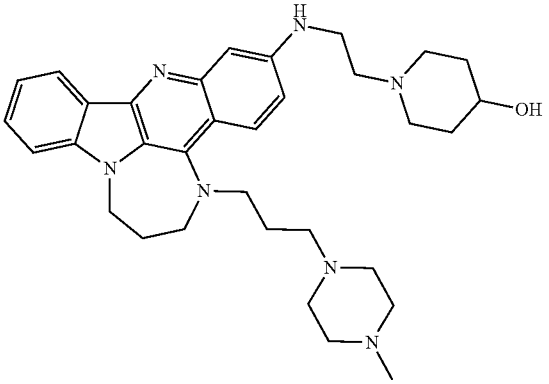

$^1$H-NMR ($CDCl_3$, 500 MHz): δ 8.50 (d, J=7.5 Hz, 1H, ArH), 8.03 (d, J=9.0 Hz, 1H, ArH), 7.57 (t, J=7.2 Hz, 1H, ArH), 7.41 (d, J=8.5 Hz, 1H, Ar·H), 7.29 (t, J=7.2 Hz, 1H, ArH), 7.25 (s, 1H, ArH), 6.97 (dd, J=2.0 & 9.0 Hz, 1H, Ar·H), 4.71-4.60 (brs, 1H, —NH), 4.18 (t, J=5.7 Hz, 2H), 3.82-3.70 (m, 1H), 3.69-3.58 (m, 2H), 3.45-3.25 (m, 4H), 2.95-2.79 (m, 2H), 2.78-2.67 (m, 3H), 2.65-2.30 (m, 11H), 2.31 (s, 3H), 2.29-2.13 (m, 3H), 2.10-2.85 (m, 4H), 1.72-1.55 (m, 2H).

$^{13}$C-NMR ($CDCl_3$): 148.77, 147.79, 147.63, 145.51, 140.82, 129.14, 128.43, 125.12, 123.54, 122.27, 120.05, 117.39, 116.74, 110.07, 105.45, 68.33, 56.80, 56.14, 55.49, 53.62, 53.06, 52.30, 50.38, 47.14, 46.44, 40.94, 34.99, 26.57, 26.22.

HRMS: Found=556.3755 ($MH^+$) (Theoretically=556.3758) Error=0.6 ppm

Compound 41

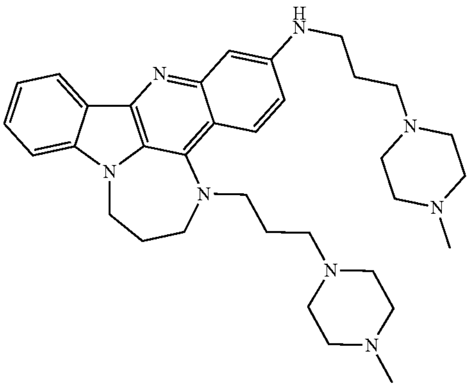

$^1$H-NMR ($CDCl_3$, 300 MHz): δ 9.02 (d, J=7.8 Hz, 1H, ArH), 7.74 (d, J=9.3 Hz, 1H, ArH), 7.69-7.52 (m, 2H, ArH), 7.37 (d, J=8.4 Hz, 1H, Ar·H), 7.32-7.21 (m, 1H, ArH, merged with $CDCl_3$ peak), 7.10 (d, J=7.8 Hz, 1H, Ar·H), 6.62-6.48 (brs, 1H, —NH), 4.40-4.21 (m, 2H), 3.91-3.80 (m, 2H), 3.73 (t, J=6.9 Hz, 2H), 3.45-3.30 (m, 2H), 3.28-3.19 (m, 4H), 3.18-2.88 (m, 4H), 2.87-2.72 (m, 6H), 2.71-2.61 (m, 3H), 2.60 (s, 6H), 2.52-2.40 (m, 3H), 2.39-2.28 (m, 2H), 2.10-1.85 (m, 4H).

$^{13}$C-NMR ($CDCl_3$): 151.49, 149.08, 143.79, 141.24, 134.87, 131.26, 126.94, 124.98, 123.66, 121.76, 116.69, 116.10, 111.69, 110.58, 94.95, 55.80, 55.35, 54.35, 53.97, 53.12, 52.24, 51.13, 50.84, 47.55, 44.58, 41.51, 27.31, 25.89, 24.90.

HRMS: Found=569.40758 ($MH^+$) (Theoretically=569.8065) Error=−2.5 ppm

Compound 48

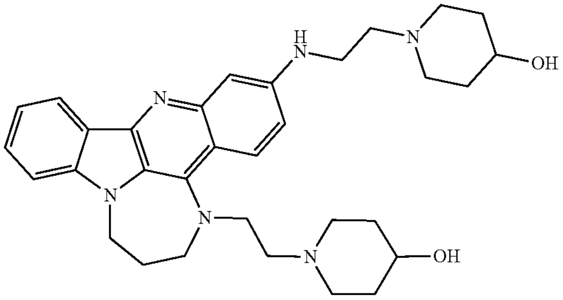

$^1$H-NMR ($CDCl_3$, 500 MHz): δ 8.52 (d, J=7.5 Hz, 1H, ArH), 8.12 (d, J=9.0 Hz, 1H, ArH), 7.58 (t, J=7.5 Hz, 1H, Ar·H), 7.42 (d, J=8.5 Hz, 1H, ArH), 7.29 (t, J=7.2 Hz, 1H, ArH, merged with $CDCl_3$ peak), 7.25 (s, 1H, ArH), 6.97 (d, J=9.0 Hz, 1H, Ar·H), 4.85-4.65 (brs, 1H, —NH), 4.20 (t, J=5.5 Hz, 2H), 3.85-3.62 (m, 4H), 3.49 (t, J=6.5 Hz, 2H), 3.43-3.30 (m, 2H), 2.95-2.65 (m, 8H), 2.50-2.36 (m, 3H), 2.28-2.12 (m, 5H), 2.05-1.78 (m, 4H), 1.75-1.48 (m, 4H).

$^{13}$C-NMR ($CDCl_3$): 148.49, 147.87, 145.36, 129.22, 128.18, 125.26, 123.21, 122.41, 120.09, 117.29, 116.45, 110.03, 105.03, 68.29, 68.11, 57.32, 56.77, 52.83, 52.07, 51.27, 51.05, 47.10, 41.51, 40.82, 34.86, 26.55.

HRMS: Found=543.3448 (MH+) (Theoretically=543.7228) Error=−1.1 ppm

Compound 30

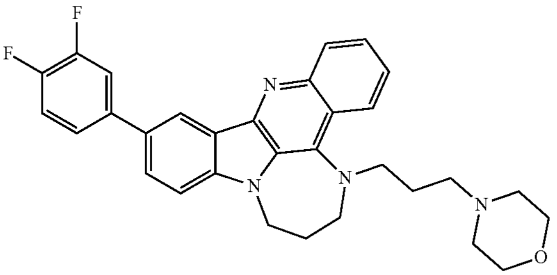

$^1$H-NMR ($CDCl_3$, 500 MHz): δ 8.70 (s, 1H, ArH), 8.29 (d, J=8.5 Hz, 1H, ArH), 8.27 (d, J=8.5 Hz, 1H, ArH), 7.79 (dd, J=2.0 &9.0 Hz, 1H, ArH), 7.70-7.64 (m, 1H, ArH), 7.62-7.44 (m, 4H, ArH), 7.30-7.22 (m, 1H, ArH+$CDCl_3$ peak), 4.26 (t, J=5.7 Hz, 2H), 3.79-3.64 (m, 6H), 3.45 (t, J=6.0 Hz, 2H), 2.52-2.38 (m, 8H) 2.10-2.0 (m, 2H).

$^{13}$C-NMR ($CDCl_3$): 152.69, 152.52, 151.71, 151.55, 149.41, 149.24, 148.43, 148.26, 147.67, 146.45, 145.38, 140.00, 138.89, 138.84, 138.76, 131.70, 130.07, 129.71, 128.70, 127.28, 124.47, 124.04, 123.45, 123.40, 123.35, 123.32, 123.27, 120.59, 118.00, 117.78, 116.45, 116.21, 110.57, 67.31, 56.36, 54.12, 52.87, 50.57, 47.34, 30.11, 26.30, 26.13.

HRMS: Found=513.2467 (MH+) (Theoretically=513.6008) Error=1.4 ppm

Compound 38

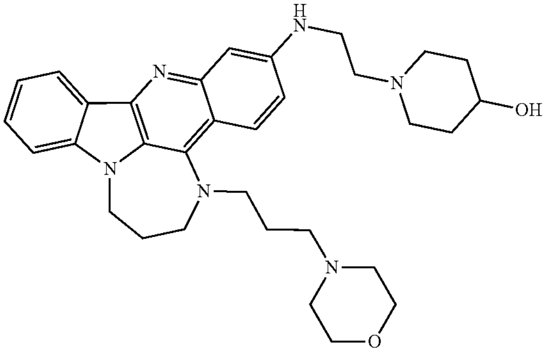

$^1$H-NMR ($CDCl_3$, 500 MHz): δ 8.70 (d, J=8.0 Hz, 1H, ArH), 7.93 (d, J=9.0 Hz, 1H, ArH), 7.58 (t, J=7.7 Hz, 1H, ArH), 7.48-7.35 (m, 2H, Ar·H), 7.33-7.25 (m, 1H, Ar·H, merged with $CDCl_3$ peak), 6.98 (d, J=9.0 Hz, 1H, Ar·H), 5.40-5.20 (brs, 1H, —NH), 4.23 (t, J=5.5 Hz, 2H), 3.90-3.60 (m, 7H), 3.53 (t, J=7.2 Hz, 2H), 3.48-3.35 (m, 2H), 3.0-2.88 (m, 2H), 2.87-2.75 (m, 2H), 2.55-2.28 (m, 10H) 2.10-1.85 (m, 4H), 1.80-1.65 (m, 2H).

$^{13}$C-NMR ($CDCl_3$): 148.85, 144.88, 129.96, 126.71, 125.80, 123.39, 120.74, 117.18, 114.98, 110.20, 67.28, 56.41, 56.19, 54.07, 51.19, 50.82, 47.28, 40.19, 34.00, 30.09, 26.78, 26.25.

HRMS; Found=543.3442 (MH+) (Theoretically=542.3432) Error=1.9 ppm

Compound 46

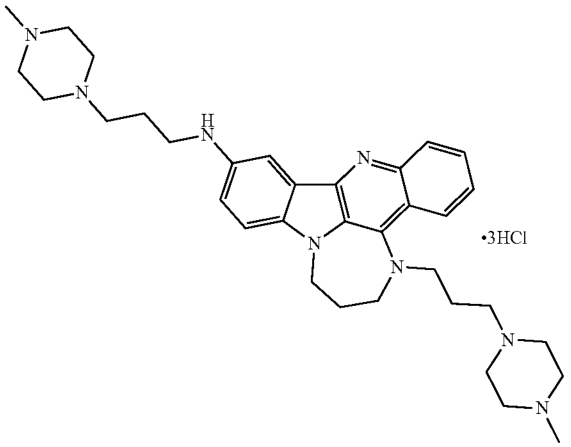

$^1$H-NMR ($D_2O$, 500 MHz): δ 8.0-7.87 (m, 2H, ArH), 7.76 (d, J=7.0, 1H, ArH), 7.63 (d, J=7.0 Hz, 1H, Ar·H), 7.57-7.48 (m, 1H, ArH), 7.47-7.30 (m, 2H, ArH), 4.28-4.15 (m, 2H), 3.90-3.72 (m, 4H), 3.68-3.10 (m, 20H), 3.26 (t, J=8.2 Hz, 2H), 2.94 (s, 3H), 2.88 (s, 3H), 2.45-2.35 (m, 2H), 2.20-2.06 (m, 4H).

$^{13}$C-NMR ($D_2O$): 149.59, 141.74, 136.57, 133.48, 132.34, 126.89, 124.50, 124.39, 124.19, 118.97, 117.84, 114.49, 113.39, 55.19, 54.45, 54.06, 52.71, 51.00, 50.85, 49.30, 49.11, 47.51, 46.44, 43.17, 26.81, 23.74, 22.16.

HRMS: Found=569.4080 (MH+) (Theoretically=569.4080) Error=−1.0 ppm

Compound 49

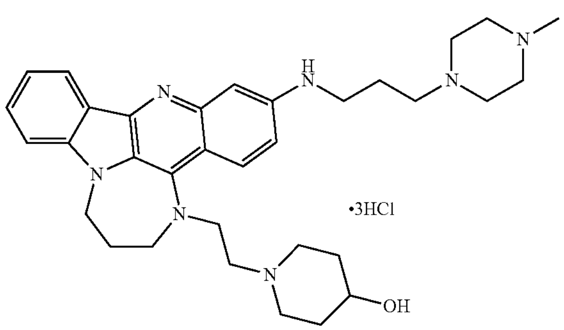

$^1$H-NMR ($D_2O$, 300 MHz): δ 7.82 (d, J=7.5 Hz, 1H, ArH), 7.44 (d, J=7.2, 1H, ArH), 7.35 (d, J=9.3 Hz, 1H, Ar·H), 7.26 (d, J=8.4 Hz, 1H, ArH), 7.19-7.02 (m, 1H, ArH), 6.70 (d, J=8.7 Hz, 1H, Ar·H), 6.17 (s, 1H, ArH), 4.02-3.92 (m, 2H), 3.88-3.72 (m, 3H), 3.70-3.42 (m, 11H), 3.40-3.30 (m, 4H), 3.24 (t, J=7.9 Hz, 2H), 3.15-3.00 (m, 4H), 2.91 (s, 3H), 2.35-2.18 (m, 2H), 2.08-1.95 (m, 2H), 1.88-1.40 (m, 4H)

$^{13}$C-NMR ($D_2O$): 151.05, 148.14, 143.17, 139.18, 132.98, 131.45, 126.35, 123.64, 121.32, 116.78, 113.70, 111.38, 110.77, 92.97, 62.06, 55.18, 53.69, 52.21, 51.21, 50.93, 49.31, 46.88, 43.22, 39.93, 31.20, 26.61, 23.37, 20.85.

HRMS: Found=556.3762 (MH+) (Theoretically=556.7646) Error=−0.8 ppm

Compound 40

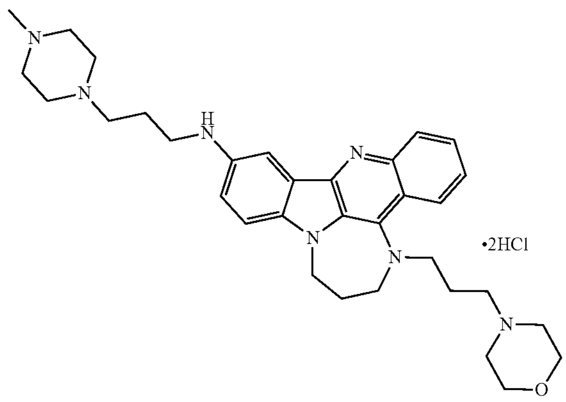

$^1$H-NMR ($D_2O$, 500 MHz): δ 7.81-7.72 (m, 1H, ArH), 7.71-7.62 (m, 2H, ArH), 7.61-7.53 (m, 1H, Ar·H), 7.44-7.28 (m, 3H, ArH), 4.12-3.93 (m, 4H), 3.80-3.45 (m, 14H), 3.41-3.28 (m, 6H), 3.10-2.97 (m, 2H), 2.96 (s, 3H), 2.91 (t, J=8.0 Hz, 3H), 2.38-2.25 (m, 2H), 2.22-2.06 (m, 4H).

$^{13}$C-NMR ($D_2O$): 148.93, 140.78, 135.99, 135.41, 133.02, 132.31, 126.40, 124.40, 123.76, 118.80, 117.33, 113.92, 113.19, 108.97, 64.07, 54.85, 54.64, 54.34, 52.46, 52.07, 50.88, 49.28, 47.41, 45.57, 43.21, 26.70, 23.16, 22.39.

HRMS: Found=556.3765 ($MH^+$) (Theoretically=556.7646) Error=−5.2 ppm

Compound 47

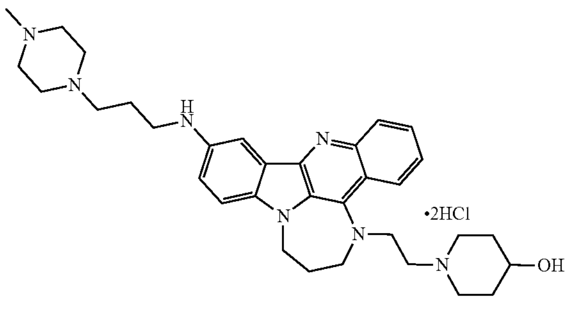

$^1$H-NMR ($D_2O$, 500 MHz): δ 7.95 (d, J=8.5 Hz, 1H, ArH), 7.88 (d, J=8.5 Hz, 1H, ArH), 7.76 (t, J=7.5 Hz, 1H, Ar·H), 7.64 (s, 1H, ArH), 7.52 (t, J=7.7 Hz, 1H, ArH), 7.47 (d, J=9.0 Hz, 1H, ArH), 7.35 (d, J=9.0 Hz, 1H, ArH), 4.25-4.15 (m, 2H), 4.12-3.98 (m, 3H), 3.88-3.75 (m, 2H), 3.60-3.25 (m, 15H), 3.14 (t, J=8.0 Hz, 4H), 2.90 (s, 3H), 2.45-2.35 (m, 2H), 2.15-2.00 (m, 2H), 1.92-1.50 (m, 3H).

$^{13}$C-NMR ($D_2O$): 148.36, 141.23, 137.72, 136.25, 134.51, 132.45, 126.02, 125.70, 125.11, 124.60, 119.44, 118.25, 114.37, 113.19, 54.85, 54.08, 52.88, 51.85, 51.67, 51.45, 49.42, 47.30, 44.86, 43.19, 26.84, 23.03.

HRMS: Found=556.3758 ($MH^+$) (Theoretically=556.7646) Error=−2.3 ppm

Compound 36

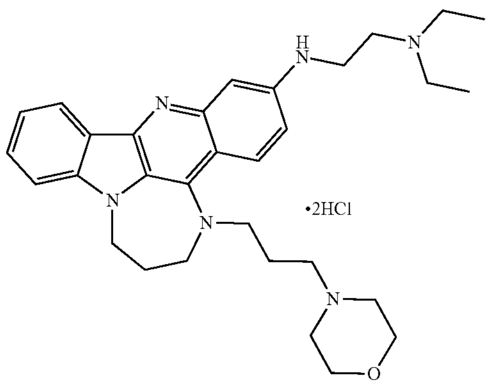

$^1$H-NMR ($D_2O$, 500 MHz): δ 7.69 (d, J=7.5 Hz, 1H, ArH), 7.33 (d, J=9.0 Hz, 1H, ArH), 7.24 (t, J=6.5 Hz, 1H, ArH), 7.10 (d, J=8.5 Hz, 1H, ArH), 6.90 (t, J=7.2 Hz, 1H, ArH), 6.66 (d, J=8.0 Hz, 1H, ArH), 6.62 (s, 1H, ArH), 4.05-3.75 (m, 6H), 3.61-3.50 (m, 2H), 3.49-3.15 (m, 14H), 2.94 (t, J=8.0 Hz, 2H), 2.25-2.06 (m, 4H), 1.26 (t, J=7.2 Hz, 6H).

$^{13}$C-NMR ($D_2O$): 150.03, 148.62, 142.53, 138.83, 132.24, 130.95, 127.13, 122.28, 121.13, 120.96, 115.73, 113.40, 111.05, 110.46, 93.49, 64.13, 54.42, 54.23, 52.12, 49.97, 48.33, 47.00, 37.67, 30.59, 26.52, 23.14, 8.64.

HRMS: Found=515.3493 ($MH^+$) (Theoretically=515.7127) Error=−0.2 ppm

Compound 34

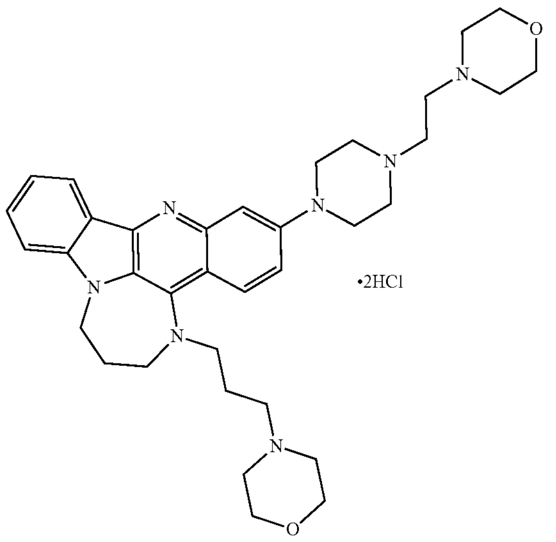

$^1$H-NMR ($D_2O$, 500 MHz): δ 7.67 (d, J=7.5 Hz, 1H, ArH), 7.46 (d, J=9.0 Hz, 1H, ArH), 7.38-7.26 (m, 1H, Ar·H), 7.11 (d, J=8.0 Hz, 1H, ArH), 6.98 (t, J=9.75, Hz, 2H, ArH), 6.45 (s, 1H, ArH), 4.10-3.91 (m, 6H), 3.90-3.80 (m, 2H), 3.79-3.65 (m, 6H), 3.64-3.35 (m, 18H), 3.12-3.00 (m, 2H), 2.94 (t, J=8.0 Hz, 2H), 2.25-2.08 (m, 4H).

$^{13}$C-NMR ($D_2O$): 150.83, 148.36, 142.78, 137.92, 132.73, 131.46, 127.43, 122.40, 121.23, 115.08, 113.26, 111.16, 98.80, 64.21, 64.10, 54.36, 52.95, 52.50, 52.11, 50.76, 50.20, 47.07, 44.82, 26.60, 23.15.

HRMS: Found=598.3861 ($MH^+$) (Theoretically=598.8013) Error=−1.7 ppm

Compound 43

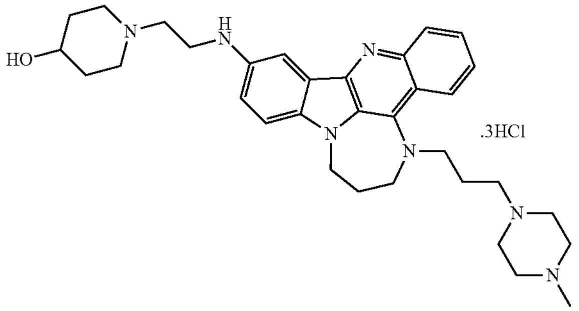

.3HCl $^1$H-NMR ($D_2O$, 300 MHz): δ 7.96 (d, J=8.4 Hz, 1H, ArH), 7.76 (d, J=8.7, 1H, ArH), 7.68 (t, J=7.5 Hz, 1H, Ar·H), 7.47-7.28 (m, 2H, ArH), 7.21 (s, 1H, ArH), 7.09 (d, J=9.3 Hz, 1H, ArH), 4.18-4.00 (m, 2H), 3.82-3.68 (m, 5H), 3.53-3.42 (m, 3H), 3.41-3.26 (m, 4H), 3.18-2.95 (m, 3H), 2.70-2.55 (m, 6H), 2.45-2.25 (m, 5H), 2.22-2.12 (m, 3H), 1.95-1.70 (m, 5H).

$^{13}$C-NMR ($D_2O$): 148.73, 141.73, 138.66, 135.86, 133.12, 131.56, 126.53, 123.92, 123.63, 122.49, 118.59, 117.37, 114.13, 112.43, 101.02, 54.93, 53.88, 52.45, 51.71, 51.36, 49.49, 49.16, 47.07, 43.23, 43.08, 31.14, 27.01, 24.37, 24.01.

Hrms: Found=556.3760 ($MH^+$) (Theoretically=556.3764) Error=−0.3 ppm

Compound 44

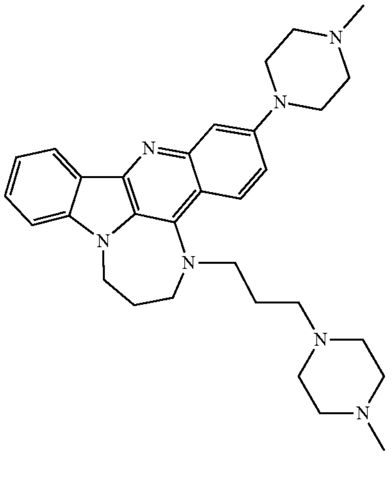

$^1$H-NMR ($CDCl_3$, 300 MHz): δ 8.47 (d, J=7.5 Hz, 1H, ArH), 8.08 (d, J=9.3, 1H, ArH), 7.65-7.46 (m, 2H, ArH), 7.37 (d, J=8.1 Hz, 1H, ArH), 7.33-7.20 (m, 2H, ArH), 4.28-4.08 (m, 2H), 3.72-3.54 (m, 2H), 3.52-3.37 (m, 4H), 3.33 (t, J=7.2 Hz, 2H), 2.78-2.58 (m, 4H), 2.57-2.29 (m, 15H), 2.28 (s, 3H), 2.10-1.88 (m, 2H).

$^{13}$C-NMR ($CDCl_3$): 150.39, 148.04, 147.90, 145.46, 140.19, 129.28, 128.67, 125.06, 123.42, 122.12, 120.08, 117.89, 117.79, 111.55, 110.04, 55.98, 55.49, 53.58, 52.92, 50.36, 49.70, 47.07, 46.58, 46.45, 26.52, 26.15.

HRMS: Found=512.3497 ($MH^+$) (Theoretically=512.7121) Error=−1.8 ppm

Compound 45

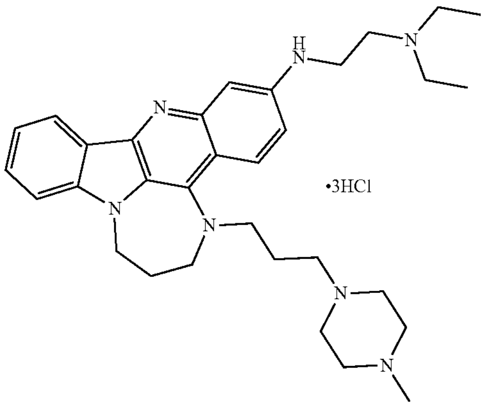

•3HCl $^1$H-NMR ($D_2O$, 300 MHz): δ 7.74 (d, J=8.1 Hz, 1H, ArH), 7.39 (d, J=9.3, 1H, ArH), 7.31 (t, J=7.8 Hz, 1H, ArH), 7.15 (d, J=8.4 Hz, 1H, ArH), 6.97 (t, J=7.5 Hz, 1H, ArH), 6.64 (d, J=Hz, 1H, ArH), 6.19 (s, 1H, ArH), 4.00-3.85 (m, 2H), 3.65-3.52 (m, 2H), 3.51-3.12 (m, 18H), 2.92-2.78 (m, 5H), 2.28-2.16 (m, 2H), 2.15-1.98 (m, 2H), 1.23 (t, J=7.2 Hz, 6H).

$^{13}$C-NMR ($CDCl_3$): 150.09, 148.87, 142.73, 139.00, 132.36, 131.06, 127.43, 122.48, 121.23, 121.10, 115.63, 113.63, 111.21, 110.56, 93.59, 54.60, 54.17, 51.95, 51.08, 50.01, 49.25, 48.34, 47.02, 43.17, 37.69, 26.75, 23.85, 8.63.

HRMS: Found=528.3803 ($MH^+$) (Theoretically=528.7545) Error=1.0 ppm

Compound 51

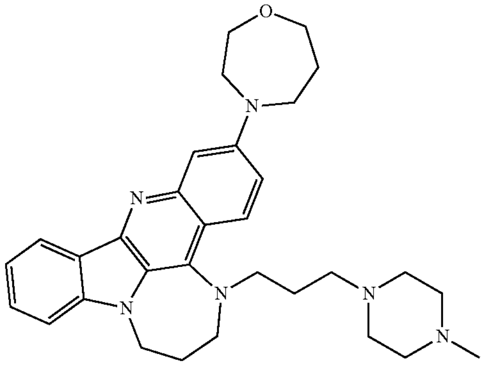

$^1$H NMR (400 MHz, Chloroform-d) δ 8.71 (s, 1H), 8.58 (d, J=7.9 Hz, 1H), 8.00 (d, J=9.4 Hz, 1H), 7.58 (ddd, J=8.4, 7.1, 1.2 Hz, 1H), 7.53 (d, J=3.3 Hz, 1H), 7.40 (d, J=8.3 Hz, 1H), 7.30 (d, J=7.3 Hz, 1H), 7.10 (dd, J=9.4, 2.6 Hz, 1H), 4.24-4.16 (m, 3H), 3.94 (dd, J=5.5, 3.9 Hz, 2H), 3.81 (q, J=5.4, 4.2 Hz, 5H), 3.75-3.65 (m, 4H), 3.49 (t, J=7.7 Hz, 2H), 2.62 (s, 0H), 2.49 (s, 6H), 2.39 (t, J=7.1 Hz, 3H), 2.35 (s, 3H), 2.20-2.10 (m, 2H), 2.03-1.93 (m, 2H).

HRMS: Found=513.33371 $MH^+$ (Theoretically=513.33) Error=−0.1 ppm

Compound 52

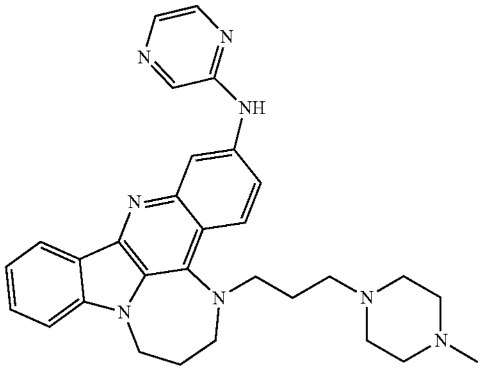

$^1$H NMR (400 MHz, Chloroform-d) δ 8.39 (d, J=2.1 Hz, 1H), 8.06 (s, 2H), 7.87 (s, 1H), 7.64 (d, J=9.0 Hz, 1H), 7.51 (s, 1H), 7.36 (d, J=8.2 Hz, 1H), 7.16 (s, 1H), 4.19 (s, 2H), 3.76-3.59 (m, 2H), 3.36 (t, J=7.6 Hz, 2H), 2.39 (t, J=7.2 Hz, 4H), 2.26 (s, 3H), 2.09-1.92 (m, 2H), 1.25 (s, 1H).

HRMS: 507.29801 $MH^+$ (Theoretically=507.3) Error=−0.2 ppm

Compound 53

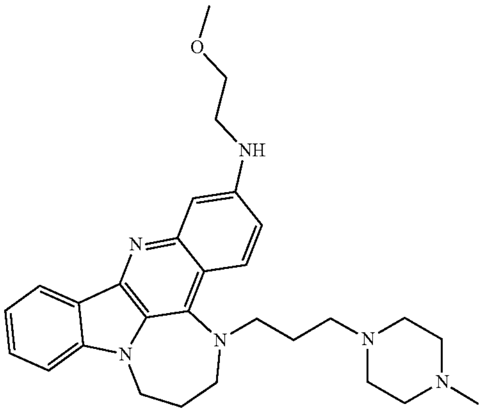

$^1$H NMR (400 MHz, Chloroform-d) δ 8.47 (dd, J=7.9, 1.2 Hz, 1H), 7.98 (d, J=9.1 Hz, 1H), 7.52 (ddd, J=8.3, 7.1, 1.3 Hz, 1H), 7.35 (d, J=8.3 Hz, 1H), 7.29-7.21 (m, 2H), 6.90 (dd, J=9.1, 2.4 Hz, 1H), 5.28 (s, 1H), 4.10 (t, J=5.9 Hz, 2H), 3.70 (dd, J=5.6, 4.6 Hz, 2H), 3.63-3.55 (m, 2H), 3.47 (t, J=4.7 Hz, 2H), 3.41 (s, 7H), 3.35-3.25 (m, 2H), 2.44 (s, 3H), 2.38-2.30 (m, 3H), 2.28 (s, 3H), 1.95 (dd, J=9.1, 6.1 Hz, 2H).

HRMS: 487.31804 $MH^+$ (Theoretically=487.32) Error=−0.1 ppm

Compound 54

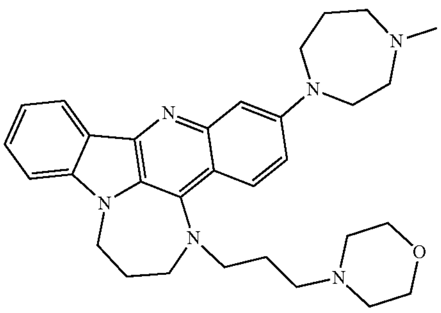

$^1$H NMR (400 MHz, $CDCl_3$) δ 8.49 (dd, J=7.9, 1.1 Hz, 1H), 8.02 (d, J=9.4 Hz, 1H), 7.55-7.49 (m, 1H), 7.34 (t, J=6.0 Hz, 2H), 7.27-7.22 (m, 1H), 7.09 (dd, J=9.4, 2.6 Hz, 1H), 4.10 (dd, J=6.7, 5.2 Hz, 2H), 3.78-3.73 (m, 2H), 3.70-3.66 (m, 6H), 3.63-3.58 (m, 2H), 3.38-3.33 (m, 2H), 2.83-2.78 (m, 2H), 2.62-2.57 (m, 2H), 2.42-2.37 (m, 7H), 2.35-2.29 (m, 4H), 2.14-2.06 (m, 2H), 2.00-1.91 (m, 2H).

$^{13}$C NMR (101 MHz, $CDCl_3$) δ 148.16, 148.07, 147.17, 145.09, 140.37, 128.82, 127.53, 124.92, 122.85, 121.92, 119.61, 115.16, 113.74, 109.66, 105.57, 66.96, 58.16, 57.04, 56.02, 53.73, 52.58, 50.13, 48.99, 48.44, 46.75, 46.71, 27.77, 25.93, 25.81.

HRMS: Found=513.3333 ($MH^+$) (Theoretically=512.3264) Error=−0.9 ppm

Compound 20

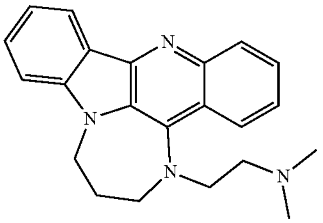

$^1$H NMR (400 MHz, $CDCl_3$) δ 8.54 (ddd, J=7.7, 1.2, 0.7 Hz, 1H), 8.31-8.26 (m, 2H), 7.68-7.57 (m, 2H), 7.51 (ddd, J=6.7, 4.4, 1.3 Hz, 1H), 7.41 (d, J=8.2 Hz, 1H), 7.35-7.30 (m, 1H), 4.23-4.17 (m, 2H), 3.71-3.67 (m, 2H), 3.51-3.45 (m, 2H), 2.79-2.73 (m, 2H), 2.41 (ddd, J=11.4, 5.7, 2.6 Hz, 2H), 2.28 (s, 6H).

$^{13}$C NMR (101 MHz, $CDCl_3$) δ 147.63, 145.99, 145.43, 139.04, 129.35, 129.28, 126.58, 123.94, 123.88, 123.03, 122.92, 121.99, 120.00, 109.68, 58.30, 52.55, 50.54, 46.64, 45.99, 25.88.

HRMS: Found=345.2072 ($MH^+$) (Theoretically=344.2001) Error=−0.7 ppm

Compound 55

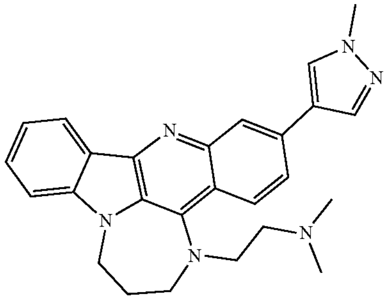

$^1$H NMR (400 MHz, DMSO-d6) δ 8.35 (s, 1H), 8.31-8.25 (m, 3H), 8.09 (s, 1H), 7.75 (dd, J=8.8, 1.9 Hz, 1H), 7.70-7.60 (m, 2H), 7.31 (t, J=7.3 Hz, 1H), 4.26 (t, J=5.8 Hz, 2H), 3.93 (s, 3H), 3.69-3.61 (m, 2H), 3.42 (t, J=6.9 Hz, 3H), 2.70 (t, J=6.9 Hz, 2H), 2.37 (dt, J=6.0, 2.4 Hz, 2H), 2.18 (s, 6H).

$^{13}$C NMR (101 MHz, DMSO) δ 147.33, 146.44, 145.44, 139.50, 136.92, 131.20, 129.79, 128.74, 128.62, 125.10, 123.72, 122.68, 122.55, 122.21, 121.47, 121.09, 120.21, 111.08, 58.27, 52.51, 50.70, 46.81, 46.05, 25.96

HRMS: Found=425.2467 ($MH^+$) (Theoretically=424.2375) Error=−1.3 ppm

Compound 56

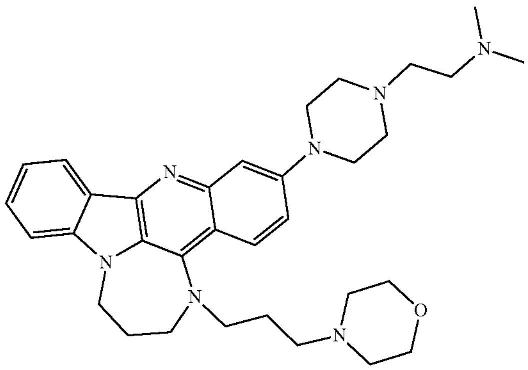

$^1$H NMR (400 MHz, Chloroform-d) δ 8.46 (d, J=7.7 Hz, 1H), 8.05 (d, J=9.4 Hz, 1H), 7.55-7.48 (m, 2H), 7.32 (d, J=8.2 Hz, 1H), 7.28-7.22 (m, 2H), 4.07 (t, J=5.8 Hz, 2H), 3.66 (t, J=4.6 Hz, 4H), 3.57 (dd, J=6.6, 3.7 Hz, 2H), 3.44-3.37 (m, 4H), 3.30 (dd, J=9.5, 5.6 Hz, 2H), 2.71 (t, J=4.9 Hz, 4H), 2.61-2.55 (m, 2H), 2.53-2.47 (m, 4H), 2.40-2.34 (m, 4H), 2.33-2.29 (m, 6H), 1.97-1.88 (m, 2H).

$^{13}$C NMR (101 MHz, $CDCl_3$) δ 150.05, 147.70, 147.54, 145.10, 139.74, 128.90, 128.32, 124.63, 123.06, 121.73, 119.71, 117.38, 117.35, 111.05, 109.66, 66.94, 57.01, 56.82, 55.98, 53.71, 53.69, 52.40, 50.03, 49.20, 46.69, 46.00, 25.81, 25.72.

HRMS: Found=556.3785 ($MH^+$) (Theoretically=555.3686) Error=−0.6 ppm

Compound 21

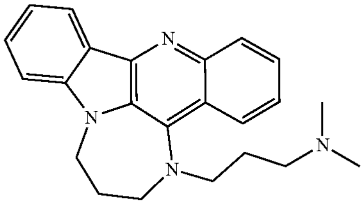

$^1$H NMR (400 MHz, $CDCl_3$) δ 8.54 (ddd, J=7.8, 1.3, 0.7 Hz, 1H), 8.29 (ddd, J=8.5, 1.3, 0.6 Hz, 1H), 8.23 (ddd, J=8.5, 1.5, 0.6 Hz, 1H), 7.67-7.59 (m, 2H), 7.51 (ddd, J=8.5, 6.7, 1.3 Hz, 1H), 7.44 (d, J=8.3 Hz, 1H), 7.33 (ddd, J=7.9, 7.2, 0.9 Hz, 1H), 4.25-4.19 (m, 2H), 3.74-3.68 (m, 2H), 3.40 (dd, J=8.7, 6.7 Hz, 2H), 2.46-2.40 (m, 4H), 2.33 (s, 6H), 2.08 (tt, J=9.9, 6.5 Hz, 2H).

$^{13}$C NMR (101 MHz, $CDCl_3$) δ 147.44, 145.82, 145.51, 139.25, 129.46, 129.34, 129.17, 126.68, 124.00, 123.88, 122.91, 122.08, 120.11, 109.77, 56.85, 52.41, 50.08, 46.73, 45.15, 26.53, 25.79.

HRMS: Found=359.2230 ($MH^+$) (Theoretically=358.2157) Error=−0.6 ppm

Compound 24

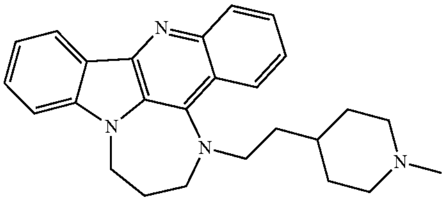

$^1$H NMR (400 MHz, $CDCl_3$) δ 8.50-8.46 (m, 1H), 8.25-8.21 (m, 1H), 8.10 (ddd, J=8.5, 1.4, 0.5 Hz, 1H), 7.62-7.57 (m, 1H), 7.52 (ddd, J=8.3, 5.2, 1.3 Hz, 1H), 7.43 (ddd, J=8.5, 6.7, 1.3 Hz, 1H), 7.31-7.24 (m, 2H), 4.08-4.02 (m, 2H), 3.56-3.50 (m, 2H), 3.24-3.16 (m, 2H), 2.87 (d, J=11.8 Hz, 2H), 2.31-2.27 (m, 3H), 2.27-2.20 (m, 2H), 1.94 (td, J=11.9, 2.5 Hz, 2H), 1.78-1.69 (m, 2H), 1.60 (d, J=12.7 Hz, 2H), 1.42 (ddd, J=25.3, 12.6, 3.8 Hz, 2H), 1.24-1.12 (m, 1H).

$^{13}$C NMR (101 MHz, $CDCl_3$) δ 147.46, 145.90, 145.29, 139.31, 129.36, 129.26, 128.90, 126.56, 123.96, 123.82, 122.85, 122.86, 121.86, 119.95, 109.690, 55.43, 52.13, 49.76, 46.69, 45.79, 35.12, 32.86, 31.76, 25.55.

HRMS: Found=399.2543 ($MH^+$) (Theoretically=399.2543) Error=0.1 ppm

Compound 57

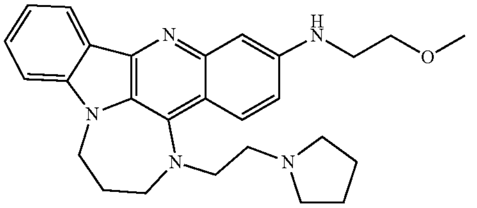

$^1$H NMR (400 MHz, $CDCl_3$) δ 8.76 (d, J=7.9 Hz, 1H), 7.87 (d, J=9.2 Hz, 1H), 7.46 (ddd, J=8.3, 5.9, 1.2 Hz, 2H), 7.28 (d, J=7.0 Hz, 1H), 7.21-7.15 (m, 1H), 6.85 (dd, J=9.2, 2.4 Hz, 1H), 4.78 (s, 1H), 4.22-4.16 (m, 2H), 3.78-3.64 (m, 6H), 3.44 (d, J=3.7 Hz, 2H), 3.41 (s, 3H), 3.03-2.95 (m, 2H), 2.59 (s, 4H), 2.42 (d, J=9.0 Hz, 2H), 1.79-1.71 (m, 4H).

$^{13}$C NMR (101 MHz, $CDCl_3$) δ 149.06, 144.95, 143.90, 129.89, 125.65, 125.29, 123.55, 120.40, 116.50, 114.27, 113.38, 109.84, 99.39, 70.52, 58.80, 54.53, 54.24, 54.12, 51.58, 46.77, 43.08, 26.69, 23.41

HRMS: Found=444.2757 ($MH^+$) (Theoretically=444.2757) Error=0.2 ppm

Compound 22

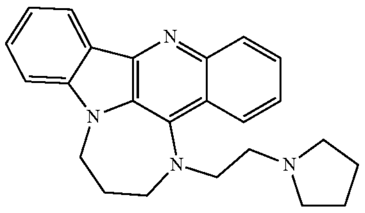

$^1$H NMR (400 MHz, $CDCl_3$) δ 8.50 (ddd, J=7.7, 1.2, 0.7 Hz, 1H), 8.27 (ddd, J=8.5, 1.3, 0.5 Hz, 1H), 8.21 (ddd, J=8.5, 1.4, 0.5 Hz, 1H), 7.63-7.58 (m, 1H), 7.54 (ddd, J=8.3, 7.1, 1.3 Hz, 1H), 7.46 (ddd, J=8.5, 6.7, 1.3 Hz, 1H), 7.34 (d, J=8.3 Hz, 1H), 7.29-7.26 (m, 1H), 4.15-4.08 (m, 2H), 3.67-3.60 (m, 2H), 3.58-3.51 (m, 2H), 2.99 (dd, J=8.5, 6.7 Hz, 2H), 2.62 (dd, J=8.8, 3.2 Hz, 4H), 2.37 (s, 2H), 1.82-1.74 (m, 4H).

$^{13}$C NMR (101 MHz, $CDCl_3$) δ 147.34, 145.70, 145.40, 138.78, 129.49, 129.17, 126.69, 124.02, 123.77, 122.72, 122.71, 121.97, 120.06, 109.75, 54.47, 54.30, 52.71, 50.71, 46.57, 26.04, 23.39.

HRMS: Found=371.2230 ($MH^+$) (Theoretically=370.2295) Error=0.2 ppm

Compound 58

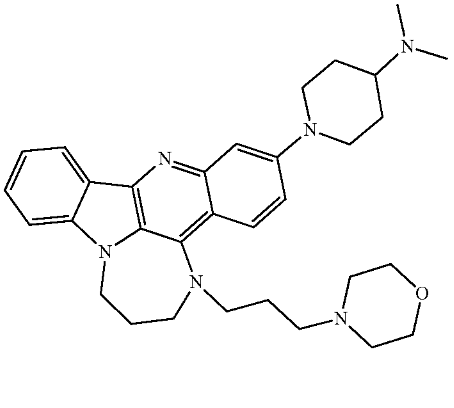

$^1$H NMR (400 MHz, $CDCl_3$) δ 8.48 (d, J=7.7 Hz, 1H), 8.07 (dd, J=9.3, 3.5 Hz, 1H), 7.55 (d, J=5.1 Hz, 2H), 7.38 (d, J=6.2 Hz, 1H), 7.28 (d, J=2.6 Hz, 2H), 4.14 (s, 2H), 3.98 (d, J=12.2 Hz, 2H), 3.69 (s, 5H), 3.63 (s, 2H), 3.37 (s, 2H), 2.86 (t, J=12.2 Hz, 2H), 2.40 (s, 4H), 2.35 (d, J=1.9 Hz, 9H), 2.01 (d, J=12.3 Hz, 4H), 1.73 (d, J=10.8 Hz, 2H).

$^{13}$C NMR (101 MHz, $CDCl_3$) δ 150.15, 147.78, 147.48, 145.13, 139.82, 128.92, 128.36, 124.59, 123.10, 121.79, 119.75, 118.03, 117.22, 111.23, 109.69, 66.97, 62.25, 56.03, 53.74, 52.48, 50.10, 49.29, 46.75, 41.77, 28.35, 25.90, 25.78.

HRMS Found=527.3492 ($MH^+$) (Theoretically=527.3495) Error=−0.3 ppm

Compound 23

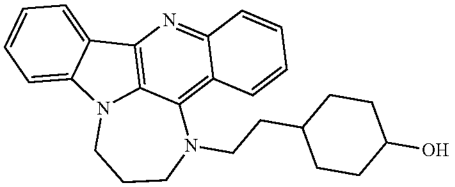

$^1$H NMR (400 MHz, $CDCl_3$) δ 8.55 (d, J=7.3 Hz, 1H), 8.29 (dd, J=8.5, 0.8 Hz, 1H), 8.21 (ddd, J=8.5, 1.4, 0.5 Hz, 1H), 7.67-7.59 (m, 2H), 7.50 (ddd, J=8.5, 6.7, 1.3 Hz, 1H), 7.43 (d, J=8.3 Hz, 1H), 7.33 (ddd, J=7.9, 7.2, 0.9 Hz, 1H), 4.25-4.19 (t, J=0.8 Hz, 2H), 3.99 (dt, J=5.3, 2.4 Hz, 1H), 3.71-3.65 (m, 2H), 3.38-3.31 (m, 2H), 2.45-2.36 (m, 2H), 1.89-1.81 (m, 2H), 1.73 (dd, J=8.9, 4.9 Hz, 2H), 1.60-1.46 (m, 6H), 1.40 (dd, J=14.8, 8.2 Hz, 1H).

$^{13}$C NMR (101 MHz, $CDCl_3$) δ 147.58, 145.98, 145.42, 139.61, 129.36, 129.29, 129.14, 126.60, 124.02, 123.85, 123.02, 122.08, 120.00, 109.67, 66.81, 52.58, 49.75, 46.81, 34.89, 34.42, 32.20, 27.20, 25.55.

HRMS: Found=400.2383 ($MH^+$) (Theoretically=400.2384) Error=−0.1 ppm

Compound 25

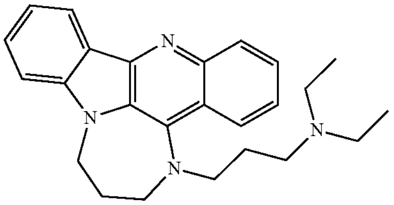

$^1$H NMR (400 MHz, $CDCl_3$) δ 8.52 (ddd, J=7.8, 1.2, 0.7 Hz, 1H), 8.28 (dd, J=8.5, 0.8 Hz, 1H), 8.13 (dd, J=8.5, 1.0 Hz, 1H), 7.62 (dtd, J=8.4, 7.0, 1.4 Hz, 2H), 7.52-7.46 (m, 1H), 7.43 (d, J=8.3 Hz, 1H), 7.35-7.30 (m, 1H), 4.23-4.16 (m, 2H), 3.75-3.69 (m, 2H), 3.42 (t, J=7.3 Hz, 2H), 2.88 (q, J=7.2 Hz, 4H), 2.73 (dd, J=9.7, 6.3 Hz, 2H), 2.44 (dd, J=13.5, 8.6 Hz, 2H), 2.28-2.19 (m, 2H), 1.19 (t, J=7.3 Hz, 6H).

$^{13}$C NMR (101 MHz, $CDCl_3$) δ 147.49, 145.81, 145.63, 138.65, 129.67, 129.26, 126.76, 124.11, 123.69, 122.79, 122.57, 122.05, 120.28, 109.96, 52.20, 50.61, 49.68, 46.78, 46.58, 26.42, 24.56, 9.28.

HRMS: Found=387.2542 ($MH^+$) (Theoretically=386.2470) Error=−0.7 ppm

Compound 14

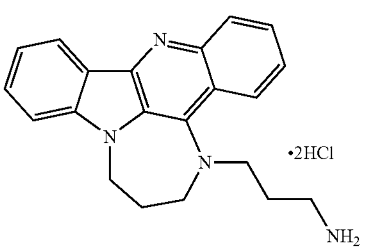

$^1$H NMR ($D_2O$, 300 MHz): δ 7.71 (d, J=8.4 Hz, 1H, ArH), 7.55 (t, J=7.5 Hz, 1H, ArH), 7.52-7.41 (m, 2H, ArH), 7.31 (t, J=7.5 Hz, 1H, ArH), 7.19 (t, J=7.6 Hz, 1H, ArH), 7.01 (d, J=8.7 Hz, 1H, ArH), 6.83 (t, J=7.5 Hz, 1H, ArH), 3.80 (t, J=5.4 Hz, 2H), 3.64-3.46 (m, 4H), 2.74 (t, J=7.6 Hz, 2H), 2.23-1.96 (m, 4H).

$^{13}$C NMR ($D_2O$): 148.47, 143.20, 135.75, 133.43, 132.19, 131.99, 126.44, 124.33, 122.67, 121.31, 121.23, 118.74, 117.45, 113.02, 111.05, 54.94, 52.16, 47.09, 37.08, 26.56.

HRMS: Found=331.1914 ($MH^+$) (Theoretically=331.1904) Error=0.9 ppm

Compound 7

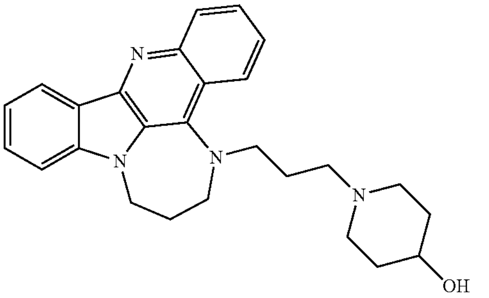

$^1$H NMR ($CDCl_3$, 500 MHz): δ 8.54 (d, J=7.5 Hz, 1H, ArH), 8.32-8.22 (m, 2H, ArH), 7.69-7.60 (m, 2H, ArH), 7.50 (t, J=7.5 Hz, 1H, ArH), 7.46 (d, J=8.0 Hz, 1H, ArH), 7.34 (t, J=7.25 Hz, 1H, ArH), 4.24 (t, J=5.5 Hz, 2H), 3.80-3.66 (m, 3H), 3.40 (t, J=7.5 Hz, 2H), 2.85-2.72 (m, 2H), 2.49-2.35 (m, 4H), 2.25-2.11 (m, 2H), 2.10-1.99 (m, 3H), 1.98-1.86 (m, 2H), 1.68-1.52 (m, 2H).

$^{13}$C NMR ($CDCl_3$): 148.05, 146.40, 145.92, 139.63, 129.82, 129.78, 129.69, 126.99, 124.34, 124.32, 123.46, 123.40, 122.46, 120.46, 110.12, 55.94, 52.84, 51.48, 50.40, 47.13, 34.71, 26.70, 26.15.

HRMS: Found=415.2493 ($MH^+$) (Theoretically=415.5505) Error=0.3 ppm

FRET

All synthesized ligands are examined with a DNA oligomer containing the G-quadruplex forming region of the c-Myc promoter (d[TGGGGAGGGTGGGGAGGGTGGGGAAGG]). The oligomer is tagged with a 5'-FAM fluorophore and a 3'-Black Hole Quencher molecule. 1 μM oligomer is linearized by heating at 95° C. for 5 minutes in a 50 mM Tris-Acetate buffer (pH 7.1) and slowly cooled back to room temperature, allowing formation of a G-quadruplex. Ligand is added to the oligomer probe at various concentrations spanning a 2-3 log range (high dose of 10 μM), allowed to incubate for 15 minutes in the dark and fluorescence is read on the BioTek Synergy HT spectrophotometer (Biotek, Winooski, VT). Drug autofluorescence is subtracted, data is normalized to oligomer only, and $ED_{35}$s are calculated from data fit by a sigmoidal top-to-bottom nonlinear regression. ED35s<10 μM are further analyzed by circular dichroism (CD).

Circular Dichroism

Non-labeled oligomers were prepared as described for FRET (Example VII). Ligands interacting with the c-Myc FRET oligomer are further examined for DNA secondary structure stabilization by CD (Sun et al., 2005). Briefly, the CD absorption spectra at 262 nm (parallel G-quadruplex) with increasing temperatures (4-95° C.) is examined in the absence and presence of 1 equivalence of ligand. $T_M$ is calculated by GraphPad Prizm using a top-to-bottom nonlinear fit, and $\Delta T_M$ are calculated for each ligands.

Cytotoxicity/Cellular Viability

To study the cytotoxicity of ligands, cells are seeded at 0.3-1.5×$10^4$ (colon) or 0.5-2.5×$10^5$ cells/well (lymphoma) in 96-well plates. Cells representing the colon include the oncogenic HCT116 and the non-transformed CCD-841-CoN cell lines, while the lymphoma cell lines include the oncogenic RAJI (with a chromosome 8:14 translocation maintaining the G-quadruplex forming region) and CA46 (with a chromosome 8:14 translocation disrupting the G-quadruplex forming region) cell lines. Both pairs of cell lines are used to determined a cytotoxicity ratio of CCD-841-CoN:HCT116 or CA46:RAJI. Cells are incubated with ligands at concentrations spanning a 5-6-log range in half-log increments for 24 or 96 h. At the prescribed time, plates are analyzed for growth inhibition and quantified with the MTS dye-based assay (Mossman, 1983). Experiments are performed with triplicate data sets. $IC_{50}$ concentrations are determined using nonlinear regression platforms in GraphPad Prizm software, and $IC_{50}$ over time is converted into an Area Under the Curve (AUC) value. AUCs of 2500 and less are selected as sufficiently cytotoxic for further analysis. Moreover, 96 h $IC_{50}$s are used to determine cell line ratios, and a ratio of >2 are chosen for further analysis.

Transcriptional and Translational Regulation

Downregulation of c-Myc mRNA and protein in HCT116, RAJI and CA46 cell lines, induced by lead ligands, is examined using quantitative real-time RT-PCR and Western blotting of cell lysates, as a function of both time (1, 4, and 24 h) and ligand concentration (0.5-, 1-, and 1.5-fold 24 h $IC_{50}$ concentrations). Briefly, mRNA is isolated using the Qiashredder and RNeasy Mini kits (Qiagen), cDNA is synthesized and quantitative real-time PCR is run. Fold changes in mRNA are normalized to the housekeeping gene GAPDH, and to vehicle controls (DMSO). Protein is isolated from cells lysed with RIPA buffer plus protease inhibitors (Roche), and concentrations are determined with the BCA Protein Assay (Pierce). 30 μg of protein are resolved on a 4-12% Bis-Tris gel, transferred to a PVDF membrane and analyzed for expression of c-Myc and Actin (antibodies from Cell Signaling).

Experimental Values

Experimental values for compounds tested according to one or more of the preceding examples are reported in the following table, including, $ED_{35}$ is the concentration of ligand that decreases the relative fluorescence of a DNA FRET probe (1 μM) by 35% (identified as the threshold to minimize false negatives). $ED_{35}$ values are reported in ranges: A: >10 μM; B: ≤10 μM.

As shown in Table II, ΔTm is the increase in melting temperature of a DNA duplex in the presence of 1 equivalent of ligand (DNA:Ligand=1:1). ΔTm values are reported in ranges: A: 0-10° C. B: >10° C.

TABLE II

| Cmpd No. | $ED_{35}$ (μM) | ΔTm (° C.) |
|---|---|---|
| 1 | A | A |
| 2 | A | A |
| 3 | B | A |
| 4 | B | A |
| 5 | A | A |
| 6 | A | A |
| 7 | B | A |
| 8 | B | B |
| 9 | B | B |
| 10 | B | A |
| 11 | B | B |
| 12 | B | A |
| 13 | B | A |
| 14 | B | A |
| 15 | B | |
| 16 | | |
| 17 | | |

Ligand Binding

Following the competition dialysis assay method of the Chaires group (Ragazzon et al., *Methods* 2007, 42, 173-182, which is hereby incorporated by reference in its entirety) using 2 μM of the referenced compound, the concentration of ligand bound to G-quadruplex structure for a variety of target genes were determined. Results are summarized in the following Table III.

TABLE III

| | Compound 3 (μM) | Compound 10 (μM) |
|---|---|---|
| Bcl-2 | 3.0 | 8.3 |
| MYC | 1.0 | 6.8 |
| HIF-1α | 4.0 | 3.3 |
| hTERT | 10.5 | 9.5 |
| PDGFA | 0.5 | 1.8 |
| PDGF-Rβ | 0.0 | 8.3 |
| Telomeric | 1.0 | 2.9 |
| VEGF | 3.0 | 2.5 |

References for formation of G-quadruplex (see, Dexheimer, T. S.; et al., J Am Chem Soc 2006, 128, 5404-15; Siddiqui-Jain, A.; Grand, C. L.; Bearss, D. J.; Hurley, L. H. Proceedings of the National Academy of Sciences, USA 2002, 99, 11593-11598; De Armond, R.; et al., Biochemistry 2005, 44, 16341-50; Palumbo, S. L.; et al., Journal of the American Chemical Society 2009, in press; Qin, Y.; et al., Nucleic Acids Research 2007, 35, 7698-713; Qin, Y.; et al., Nucleic Acids Research 2009, Submission; Hardin, C. C.; et al., Biochemistry 1991, 30, 4460-72; Sun, D.; et al., Nucleic Acids Res 2005, 33, 6070-80).

Example III

This example provides specific compounds of the present invention suppress AR protein expression in androgen-dependent (LNCaP) and CRPC tumor cells (C2-4) after a 24 h treatment at 10 μM (FIG. 1A) (Cell lysates from LNCaP and C4-2 cells treated with GSA compounds at a concentration of 10 μM for 24 hours were analyzed for expression of AR, NCL, and GAPDH by immunoblotting). GSA0932 suppress AR expression in 22RV1 and VCaP tumor cells, after 24 h of treatment reaching its maximal inhibitory activity at a concentration of 3 and 5 μM respectively (FIG. 1B) (Cell lysates from indicated prostate cancer cell lines treated with increasing concentrations GSA0932 for 24 hours were analyzed for AR, NCL, and GAPDH by immunoblotting). GSA0932 also inhibits the expression of the clinically relevant ARv7 splice variant in 22RV1 (FIG. 1B) and suppressed mRNA expression of the classical AR target gene, KLK3, also known as PSA (FIG. 1C) (Extracted RNA from indicated prostate cancer cell lines treated for 12 hours with DMSO or GSA0932 (10 OA (LNCaP and C4-2), 5 μM (VCaP), or 3 μM (22RV1) was analyzed for expression of KLK2 (AR target) by RT-qPCR. Values are means±s.e.m; p<0.05 (K); n=3). GSA0932 also significantly decreased AR mRNA in LNCaP and C4-2 cells after 12 and 24 hours of treatment at 10 μM (FIG. 1D) (Extracted RNA from LCaP or C4-2 cells treated for 12 or 24 hours with DMSO, 10 μM GSA0932, or 10 μM GSA1502 was analyzed for AR expression by RT-qPCR. Values are means±s.e.m; p<0.05 (*); n=3). GSA1502 does not affect AR mRNA and protein expression (FIGS. 1A and D), and was used as negative control Quindoline-derived compound.

Example IV

This example demonstrates that a specific compound of the present invention requires nucleolin binding at the G4-element in the AR promoter for its ability to suppress AR mRNA expression. To measure the dependency of GSA0932-mediated AR suppression on the AR G4-element, we generated a stable LNCaP cell lines expressing a dual reporter in which *Gaussia* luciferase is driven by either a wild type or a mutant AR promoter lacking the G4 element, and secreted alkaline phosphatase (SEAP) is driven by a constitutive promoter. GSA0932, but not GSA1502, significantly decreases luciferase activity of a wild type reporter (FIG. 1E) (Relative luciferase in LNCaP cells stably expressing the AR G4 (Wild) or deleted G4 (ΔG4) reporter, treated with DMSO, 10 μM GSA0932, or 10 μM GSA1502 for 12 hours). However, GSA0932 had no effect on the G4-deleted AR reporter (FIG. 1E). GSA0932, but not GSA1502, increases the amount of NCL bound to the G4-element of the AR promoter in both LNCaP and C4-2 cells (FIG. 1F) (ChIP of NCL on AR G4 in the absence or presence of 10 μM GSA0932. Negative (IgG) control. Plotted as fold enrichment relative to IgG). Knocking down NCL expression alleviated the GSA0932 inhibitory activity against AR mRNA expression compared with control cells (FIG. 1G) (LNCaP cells were transfected with scrambled (Scr) or NCL siRNAs and 7211 post-transfection, cells were treated with DMSO, 10 μM GSA0932, or 10 Oil GSA1502 for 12 hours. Extracted RNA was analyzed for AR expression by RT-qPCR).

Example V

This example demonstrates that a specific compound of the present invention, GSA0932, has stronger cytotoxic activity against AR-positive tumor cells than non-AR expressing cells (FIG. 1H) (Indicated prostate cancer cell lines, or non-malignant prostate cells (RPWE), treated with different concentrations of GSA0932 for 48 h and cell viability measured by MTT). Table V provides the $IC_{50}$ values for GSA0932.

TABLE V

| IC$_{50}$ of GSA0932 | |
|---|---|
| Cell Line | IC50 (μM) |
| RWPE | 5.4 ± 0.05 |
| PC3 | 4.3 ± 0.16 |
| LNCaP | 1.4 ± 0.26 |
| VCaP | 2.8 ± 0.03 |
| C4-2 | 2.0 ± 0.04 |
| 22Rv1 | 0.9 ± 0.11 |

GSA0932

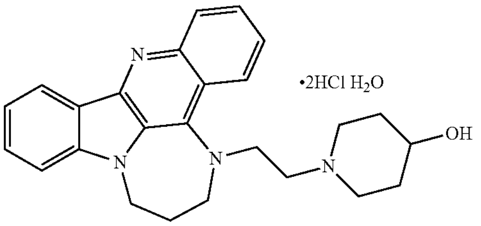

•2HCl $H_2O$

Chemical Formula: C25H28N4O 2HCl H2O$C_{25}H_{28}N_4O$
Molecular Weight: 409.8241400.53

GSA1502

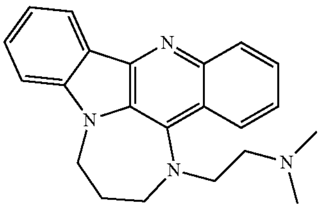

Chemical Formula: $C_{22}H_{24}N_4$
Molecular Weight: 344.4620

GSA1504

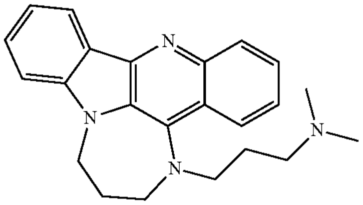

Chemical Formula: $C_{23}H_{26}N_4$
Molecular Weight: 358.4890

GSA1508

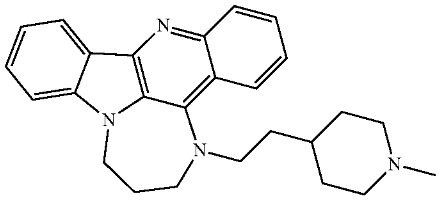

Chemical Formula: $C_{26}H_{30}N_4$
Molecular Weight: 398.55

-continued

GSA1512

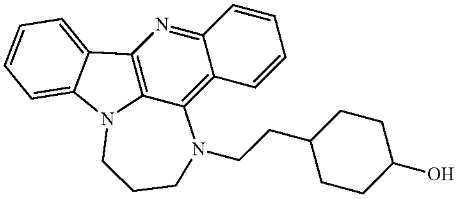

Chemical Formula: $C_{26}H_{29}N_3O$
Molecular Weight: 399.54

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound described by Formula I:

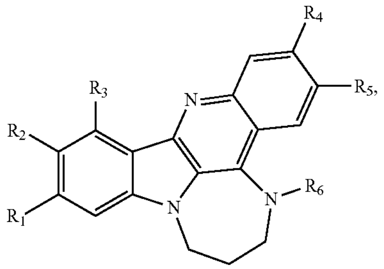

including pharmaceutically acceptable salts, solvates, and/or prodrugs thereof;

wherein $R_1$ is hydrogen or methyl;

wherein $R_2$ is selected from hydrogen,

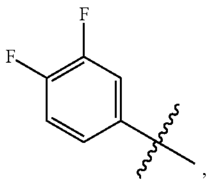

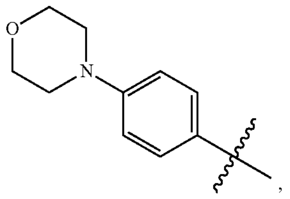

-continued
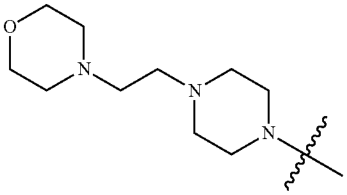
,
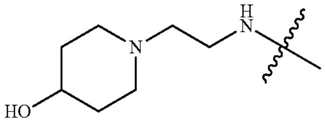
, and
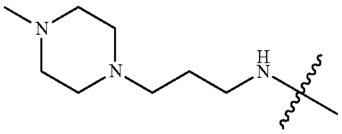
;
wherein $R_3$ is hydrogen or methyl;
wherein $R_4$ is selected from hydrogen,
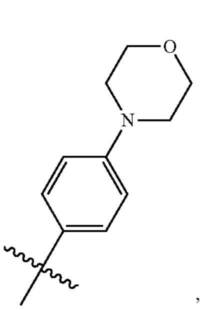
,
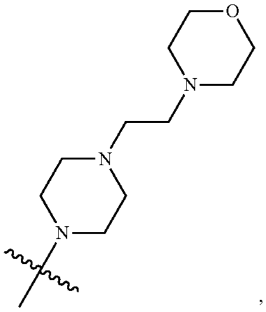
,
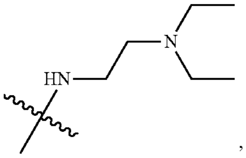
,
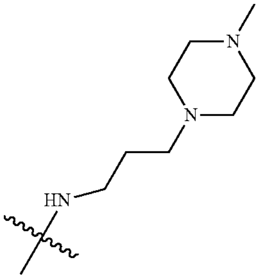
,
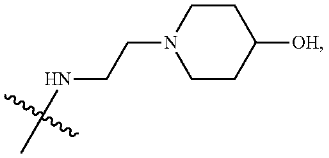
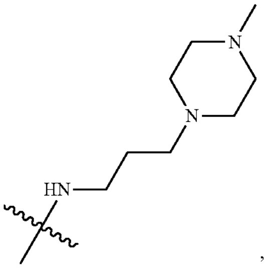
,
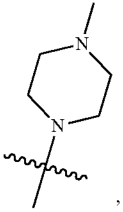
,
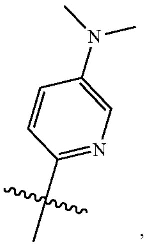
,
-continued
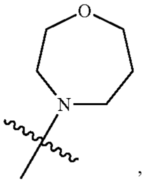
,
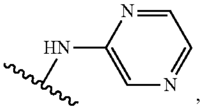
,
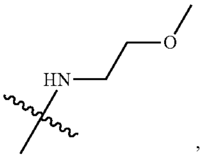
,
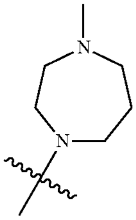
,
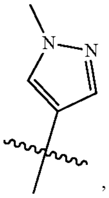
,
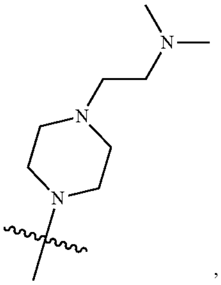
,
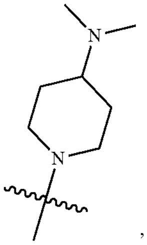
,
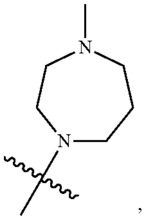
,
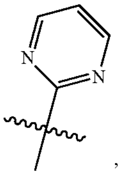
,
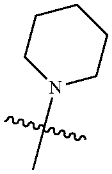
, and
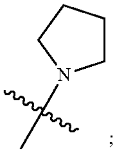
;
wherein $R_5$ is selected from Hydrogen, Chlorine, Bromine,
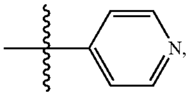
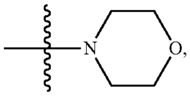
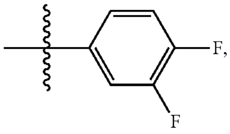
and
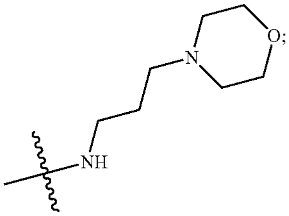
wherein $R_6$ is selected from
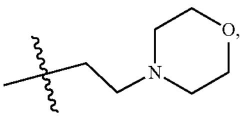
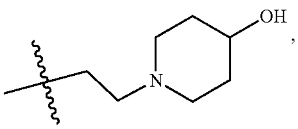
, -continued
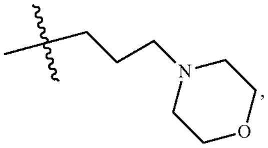
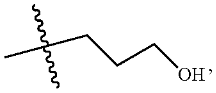
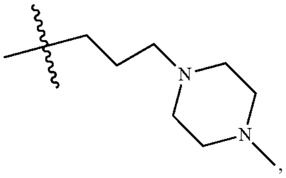
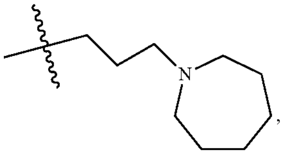
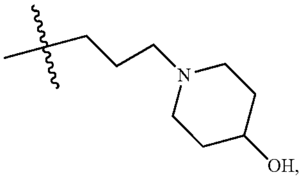
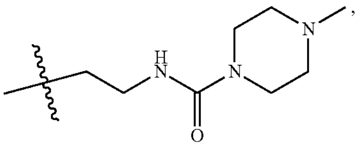
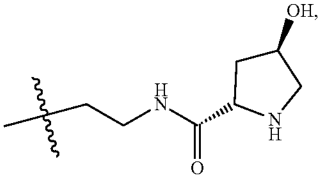
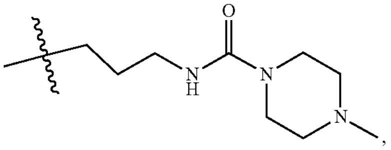
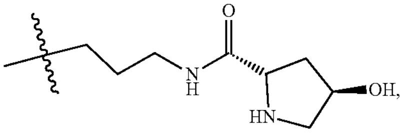
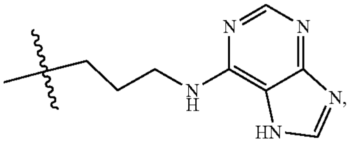
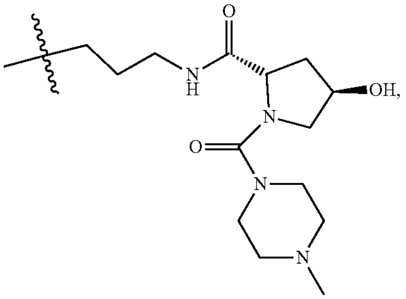
-continued
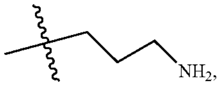
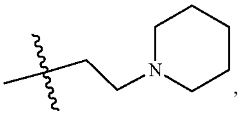
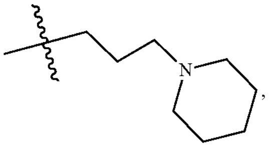
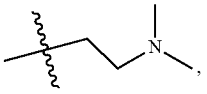
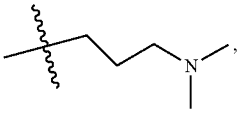
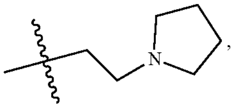
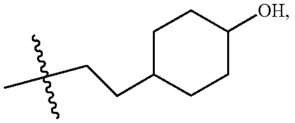
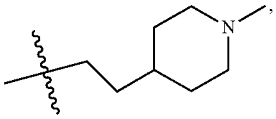
and
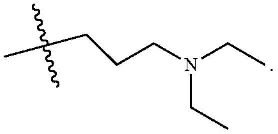
2. The compound of claim 1, wherein the compound is selected from:
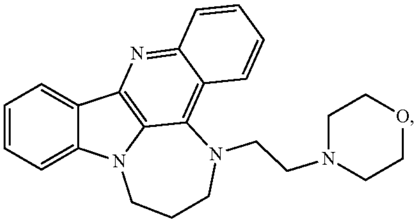
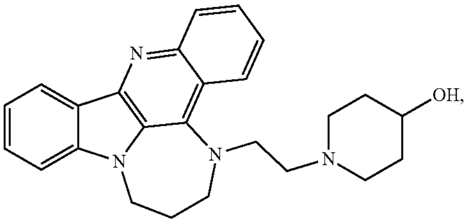
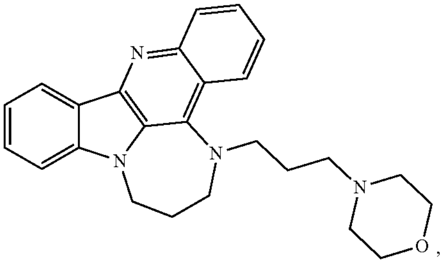

-continued
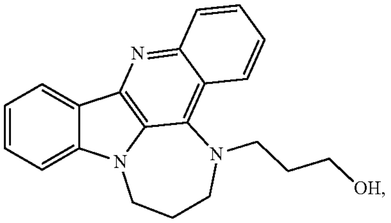
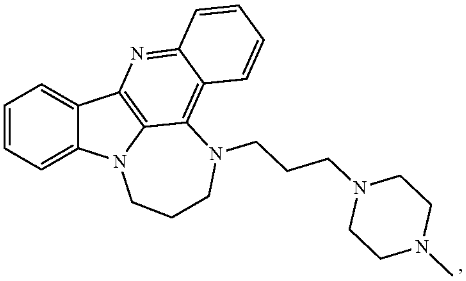
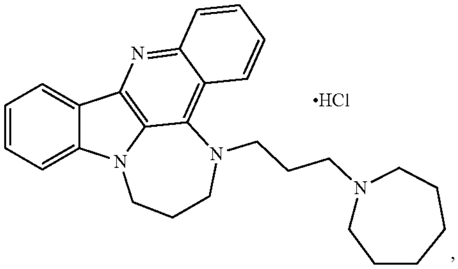
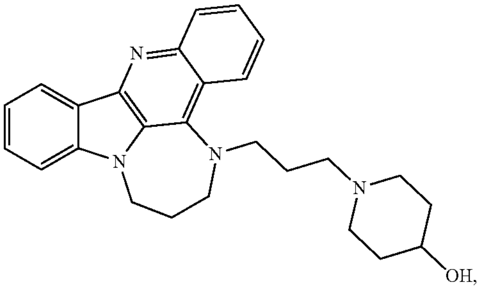
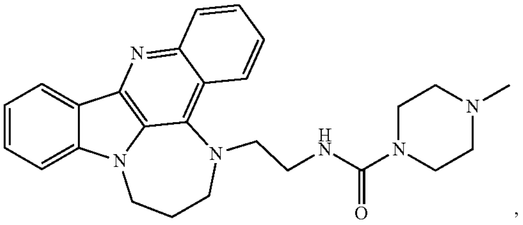
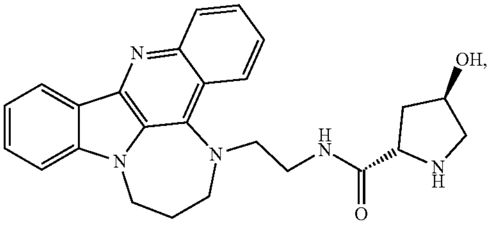
-continued
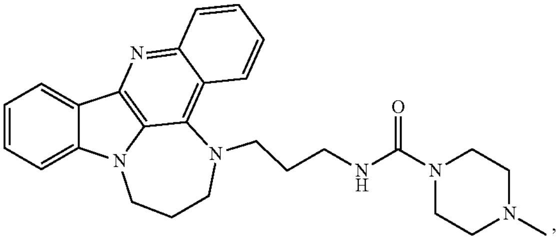
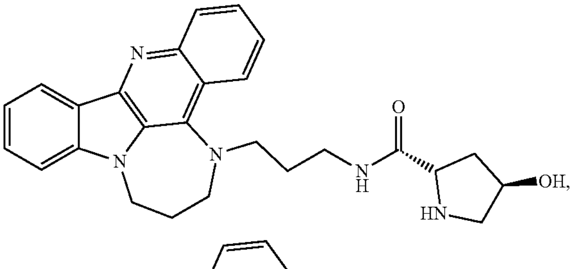
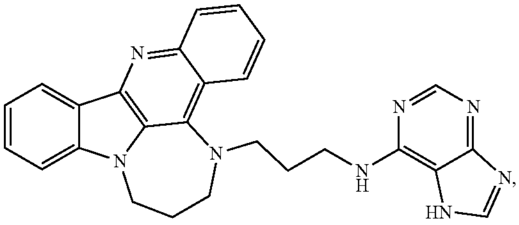
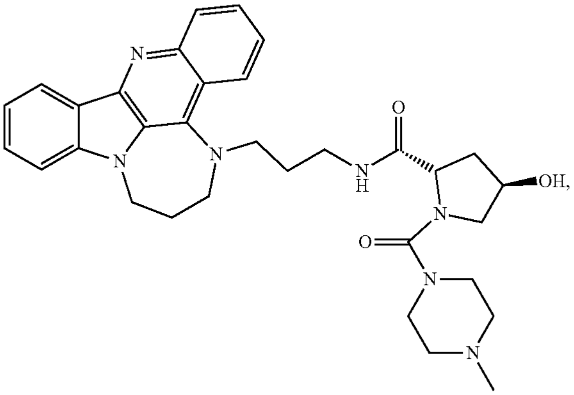
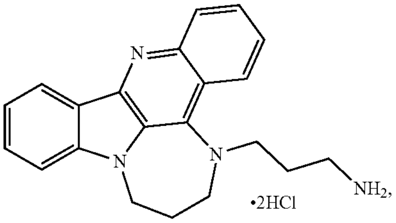
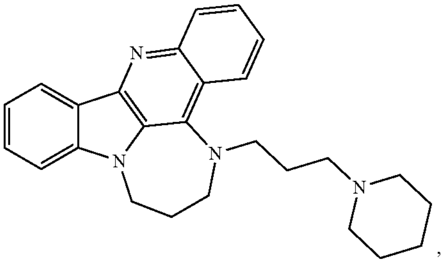

-continued
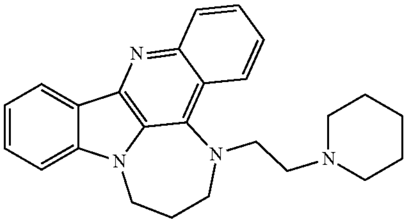
,
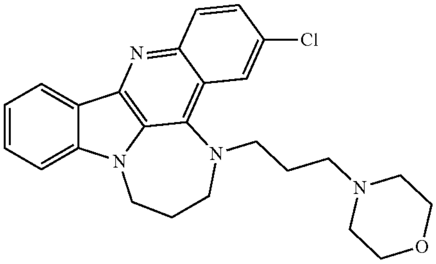
,
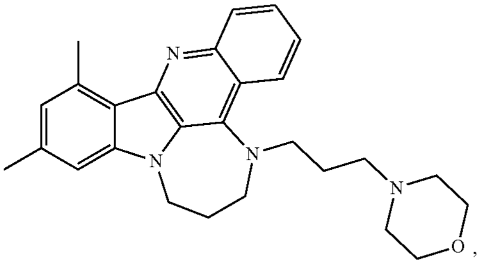
,
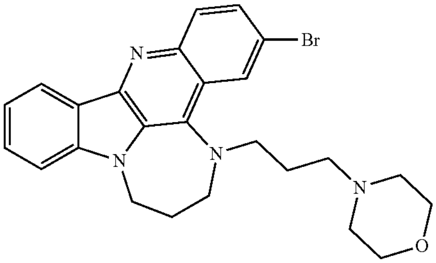
,
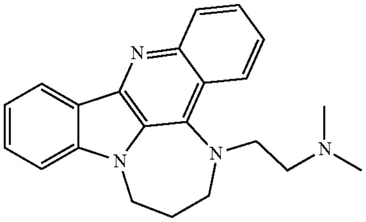
,
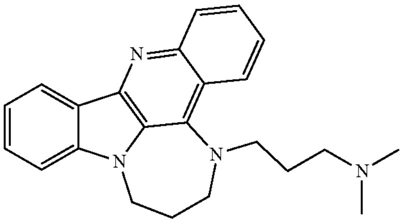
,
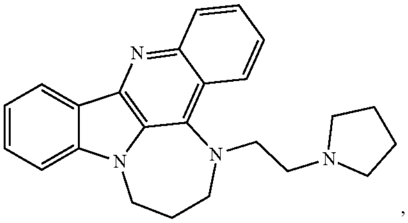
,
-continued
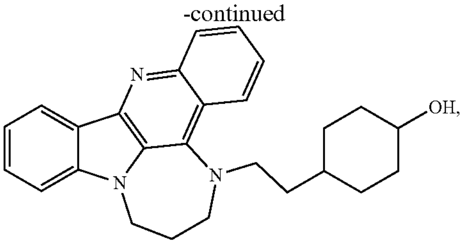
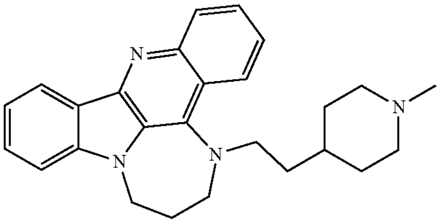
,
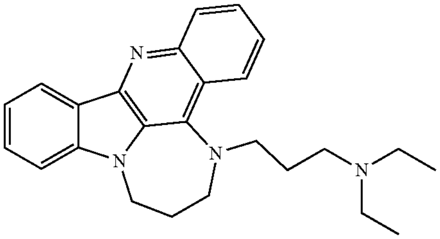
,
2HCl•$H_2O$
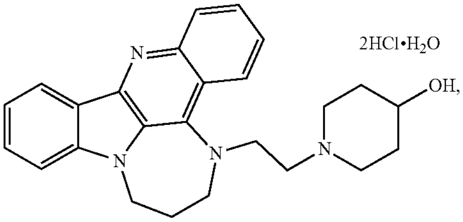
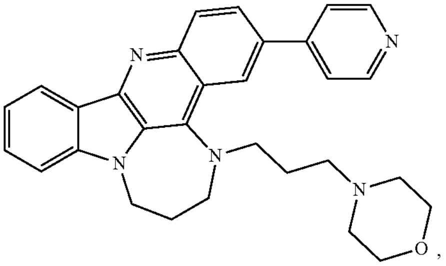
,
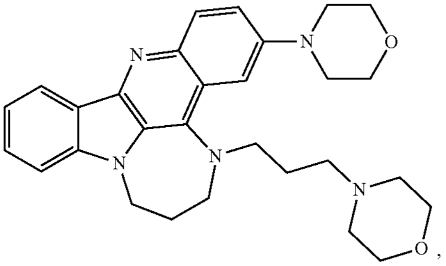
,
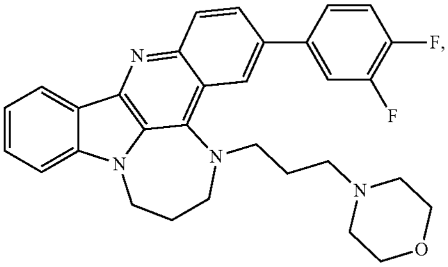

-continued
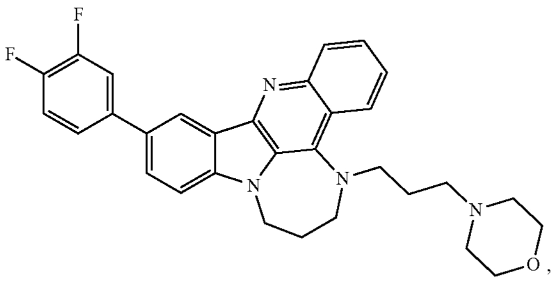
,
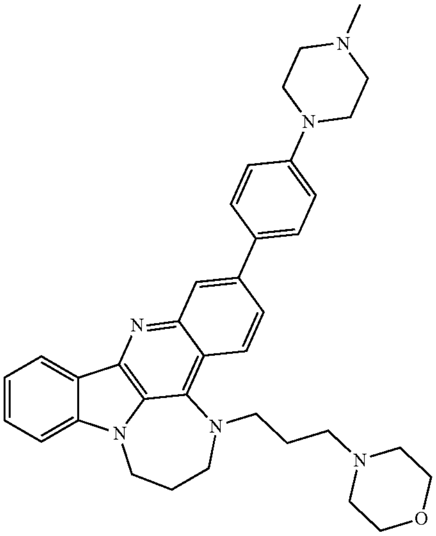
,
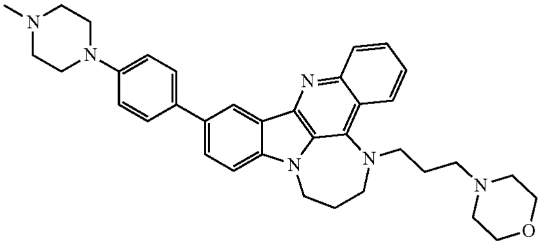
,
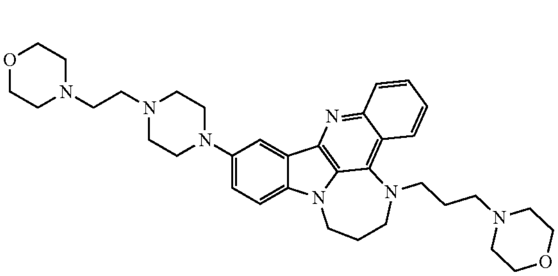
,
-continued
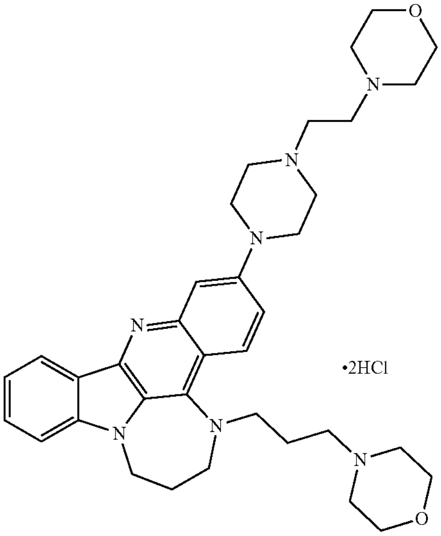
•2HCl
,
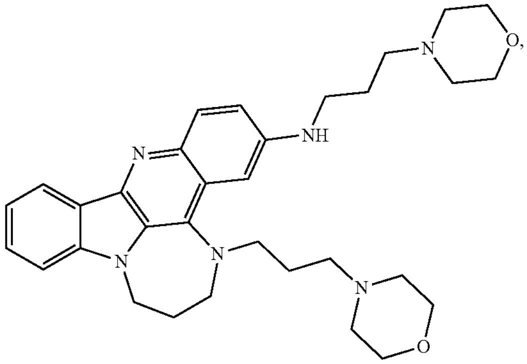
,
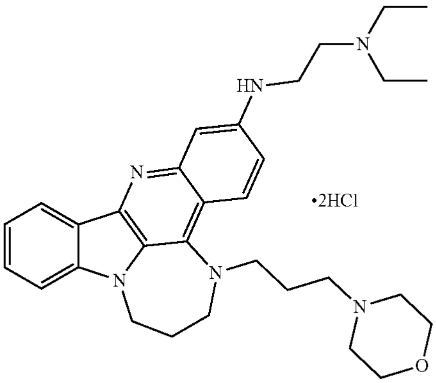
•2HCl
, -continued
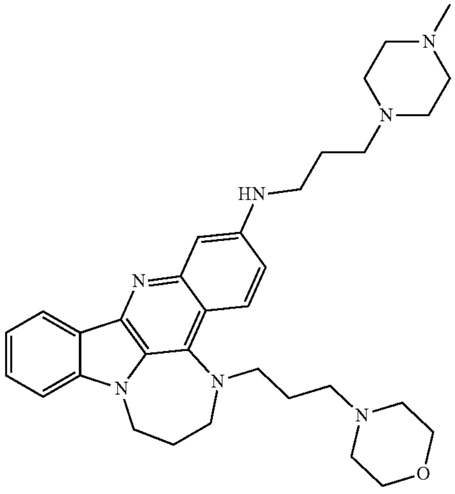
,
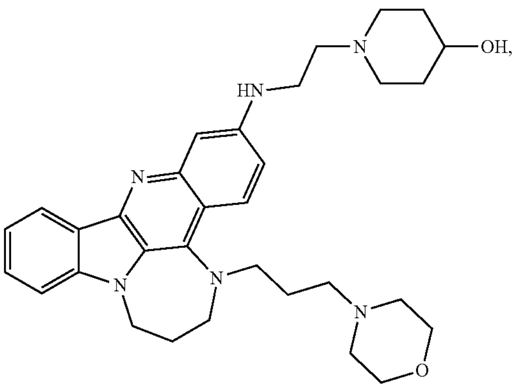
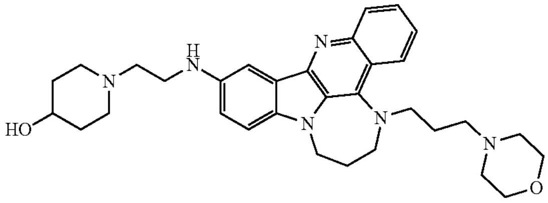
,
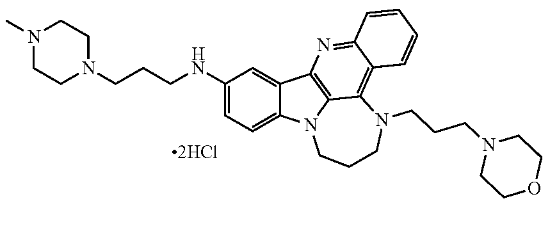
,
-continued
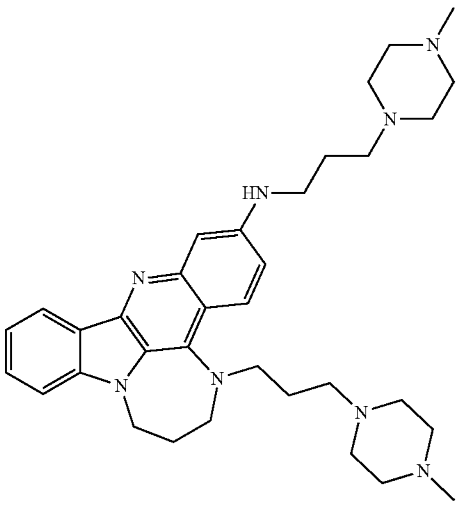
,
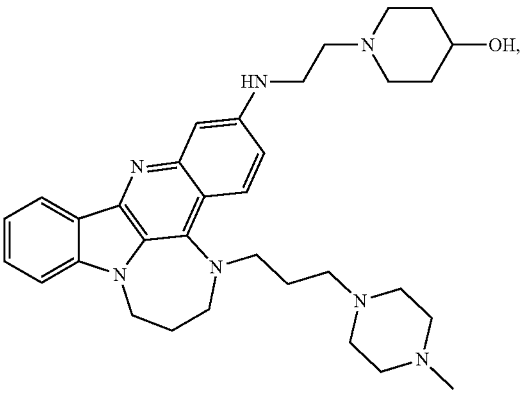
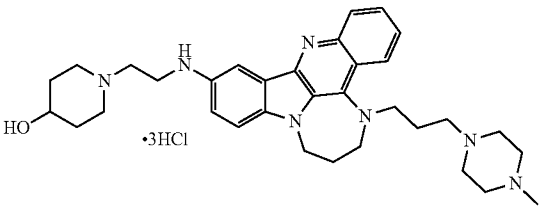
,
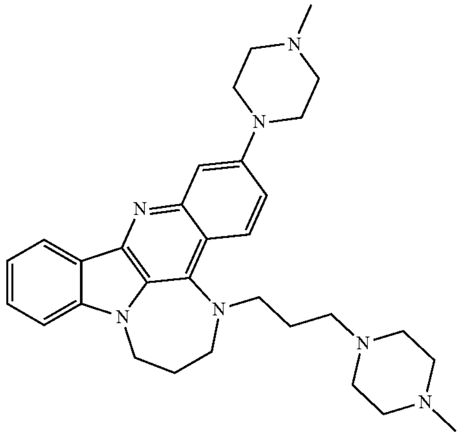
, -continued
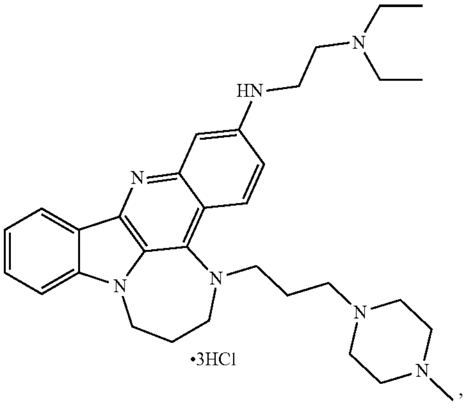
•3HCl,
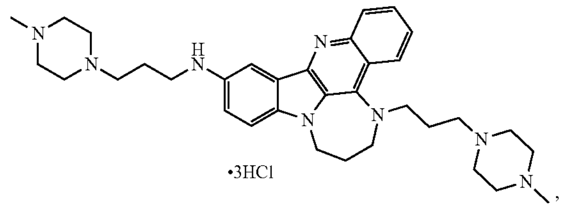
•3HCl,
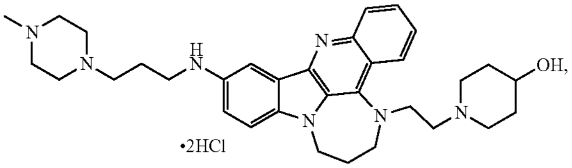
•2HCl
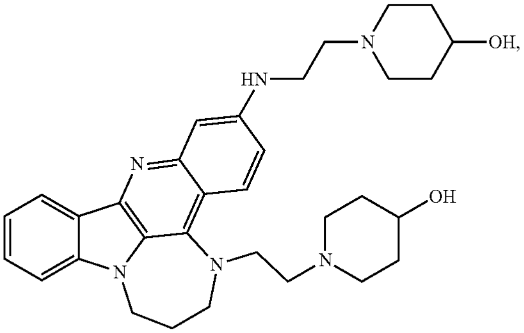
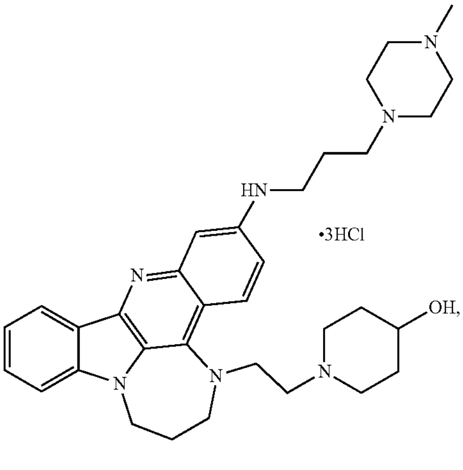
•3HCl
-continued
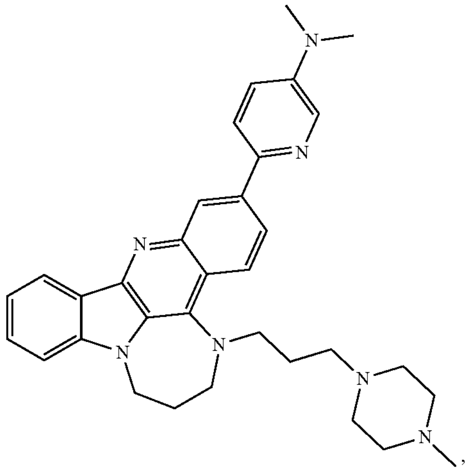
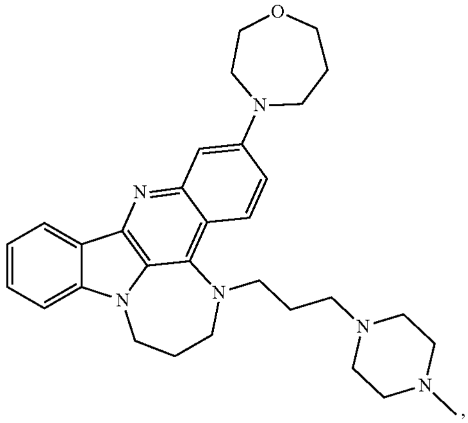
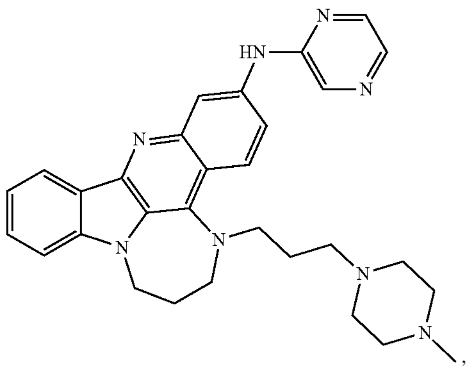

-continued
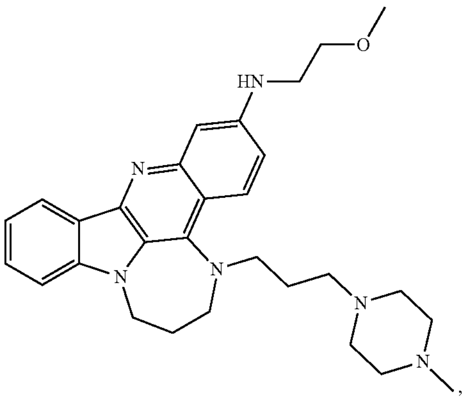
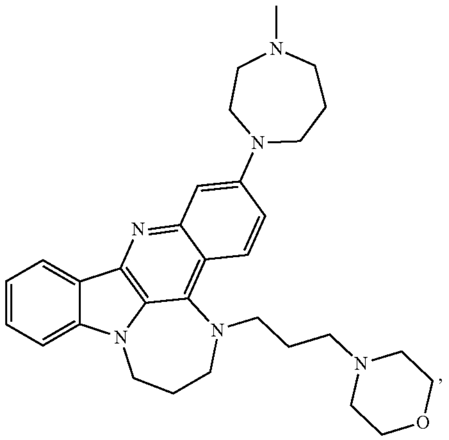
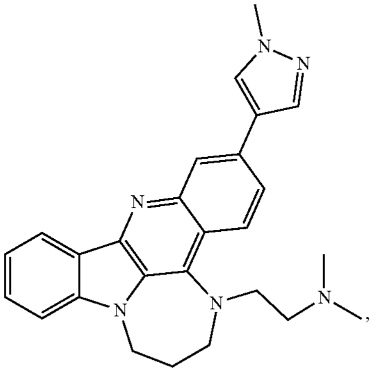
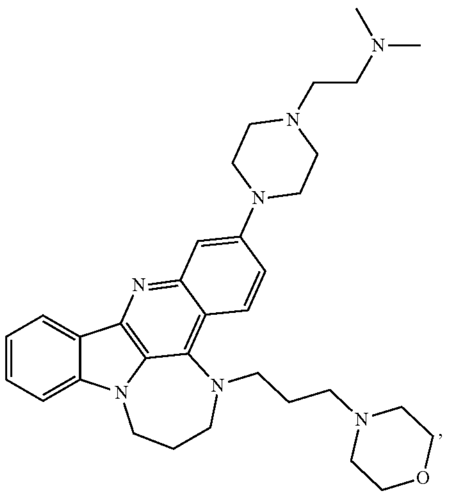
-continued
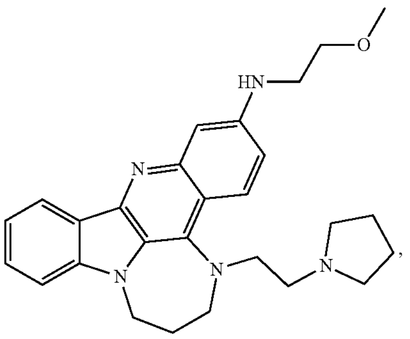
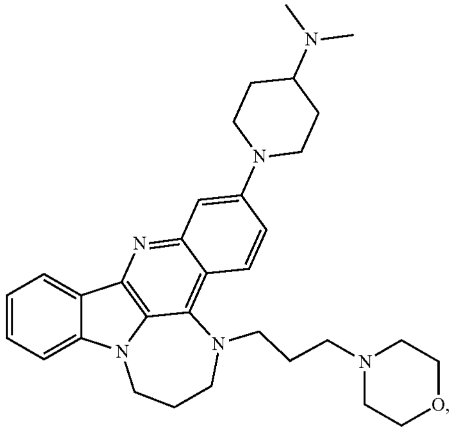
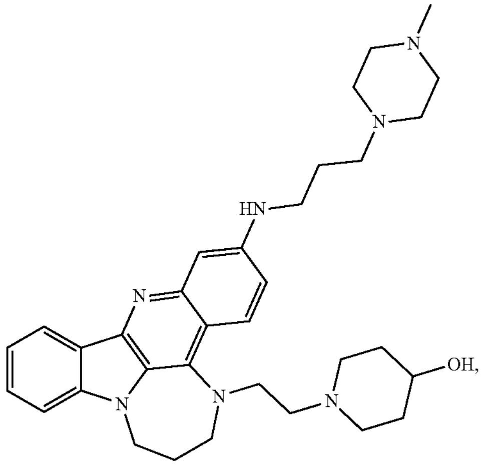

-continued

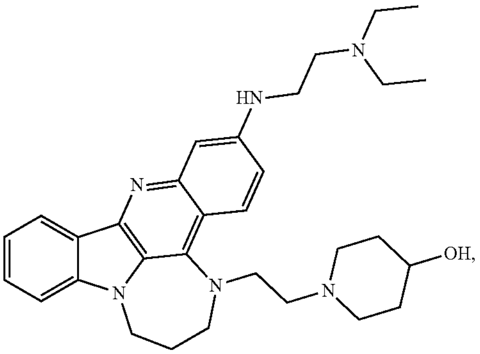

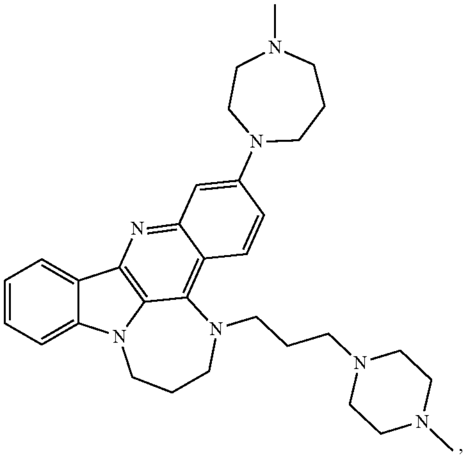

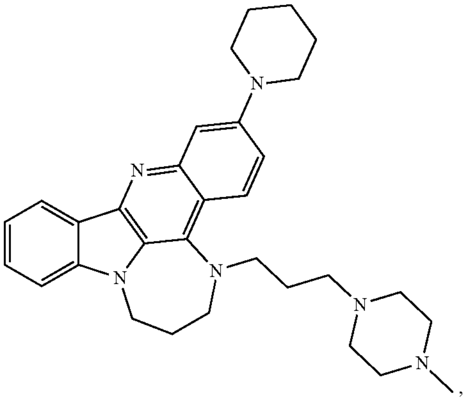

-continued

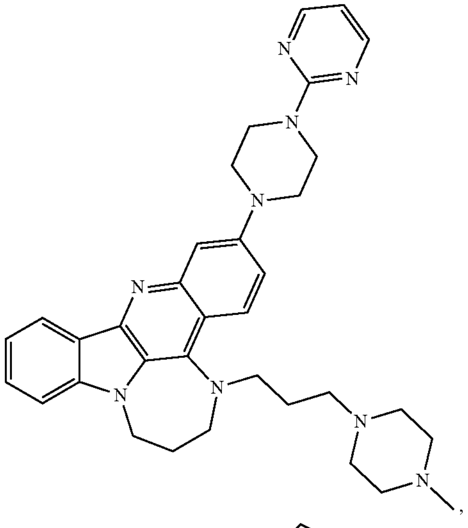

and

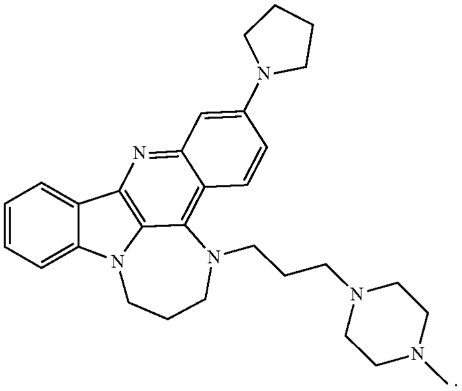

3. A pharmaceutical composition comprising a compound of claim 1.

4. A method of treating a cancer selected from prostate cancer and colon cancer, comprising administering to a patient a therapeutically effective amount of the pharmaceutical composition of claim 3.

5. The method of claim 4, wherein administration of the pharmaceutical composition results in stabilization of G-quadruplex (G4) formation.

6. The method of claim 4, wherein the patient is a human patient.

7. The method of claim 4, further comprising administering to said patient one or more anticancer agents, wherein said anticancer agent one or more of a chemotherapeutic agent, and radiation therapy, and/or administering to said patient one or more anticancer agents.

8. A kit comprising a compound of claim 1 and instructions for administering said compound to a patient having a disease or condition characterized by unstable G-quadruplex activity.

* * * * *